(12) United States Patent
Salituro et al.

(10) Patent No.: US 11,149,056 B2
(45) Date of Patent: Oct. 19, 2021

(54) C7 SUBSTITUTED OXYSTEROLS AND METHODS OF USE THEREOF

(71) Applicant: Sage Therapeutics, Inc., Cambridge, MA (US)

(72) Inventors: Francesco G. Salituro, Marlborough, MA (US); Albert Jean Robichaud, Boston, MA (US); Gabriel Martinez Botella, Wayland, MA (US); Andrew Griffin, L'lle Bizard (CA); Boyd L. Harrison, Princeton Junction, NJ (US); Daniel La, Chestnut Hill, MA (US)

(73) Assignee: SAGE THERAPEUTICS, INC., Cambridge, MA (US)

( * ) Notice: Subject to any disclaimer, the term of this patent is extended or adjusted under 35 U.S.C. 154(b) by 0 days.

(21) Appl. No.: 16/338,315

(22) PCT Filed: Sep. 30, 2017

(86) PCT No.: PCT/US2017/054657
§ 371 (c)(1),
(2) Date: Mar. 29, 2019

(87) PCT Pub. No.: WO2018/064649
PCT Pub. Date: Apr. 5, 2018

(65) Prior Publication Data
US 2020/0024300 A1 Jan. 23, 2020

Related U.S. Application Data

(60) Provisional application No. 62/402,789, filed on Sep. 30, 2016, provisional application No. 62/402,797, filed on Sep. 30, 2016.

(51) Int. Cl.
*C07J 31/00* (2006.01)
*C07J 9/00* (2006.01)

(52) U.S. Cl.
CPC ............. *C07J 31/006* (2013.01); *C07J 9/005* (2013.01)

(58) Field of Classification Search
CPC ................................ C07J 31/006; C07J 9/005
USPC ....................................................... 514/236.2
See application file for complete search history.

(56) References Cited

U.S. PATENT DOCUMENTS

| | | |
|---|---|---|
| 2,594,323 A | 4/1952 | Levin et al. |
| 2,673,206 A | 3/1954 | Ryer |
| 3,079,385 A | 2/1963 | Bertin et al. |
| 3,206,459 A | 9/1965 | Cross |
| 4,071,625 A | 1/1978 | Grunwell et al. |
| 4,174,345 A | 11/1979 | Kaiser |
| 4,183,852 A | 1/1980 | Kaiser |
| 4,868,165 A | 9/1989 | Ikekawa |
| 5,232,917 A | 8/1993 | Bolger et al. |
| 5,376,645 A | 12/1994 | Stella et al. |
| 5,595,996 A * | 1/1997 | Graham ................. A61K 31/58 514/284 |
| 5,888,996 A | 3/1999 | Farb |
| 5,925,630 A | 7/1999 | Upasani et al. |
| 6,407,086 B2 | 6/2002 | Faarup et al. |
| 6,645,953 B2 | 11/2003 | Gronvald et al. |
| 6,884,796 B2 | 4/2005 | Faarup et al. |
| 8,034,798 B2 | 10/2011 | Baulieu et al. |
| 8,247,436 B2 | 8/2012 | Baettig et al. |
| 8,604,011 B2 | 12/2013 | Mellon |
| 8,673,843 B2 | 3/2014 | Moskal et al. |
| 8,829,213 B2 | 9/2014 | Peng et al. |

(Continued)

FOREIGN PATENT DOCUMENTS

| | | |
|---|---|---|
| CN | 1257077 | 6/2000 |
| CN | 1254716 | 5/2008 |

(Continued)

OTHER PUBLICATIONS

Deng et al., Fluoro analogs of bioactive oxy-sterols: Synthesis of an EBI2 agonist with enhanced metabolic stability, 2016, Bioorganic & Medicinal Chemistry Letters, 26, 4888-4891 (Year: 2016).*

Björkhem et al., "Oxysterols in the circulation of patients with the Smith-Lemli-Opitz syndrome: abnormal levels of 24S- and 27-hydroxycholesterol", Journal of Lipid Research, vol. 42, 2001, pp. 366-371.

Bukelis et al., "Smith-Lemli-Opitz Syndrome and Autism Spectrum Disorder", American Journal of Psychiatry, 2007, vol. 164, pp. 1655-1661.

Cancer [online], [retrieved on Jul. 6, 2007]. Retrieved from the internet, URL http://www.nlm.nih.gov/medlineplus/cancer.html>.

Cecil Textbook of Medicine, 20th edition (1996), vol. 2, pp. 1992-1996.

(Continued)

*Primary Examiner* — Kristin A Vajda
(74) *Attorney, Agent, or Firm* — Haley Guiliano LLP; Karen Mangasarian

(57) ABSTRACT

Compounds are provided according to Formula (A): and pharmaceutically acceptable salts thereof, and pharmaceutical compositions thereof; wherein $R^{1A}$, $R^{1b}$, n, $R^{2A}$, $R^{2b}$, $R^3$, and $R^4$ are as defined herein. Compounds of the present invention are contemplated useful for the prevention and treatment of a variety of conditions.

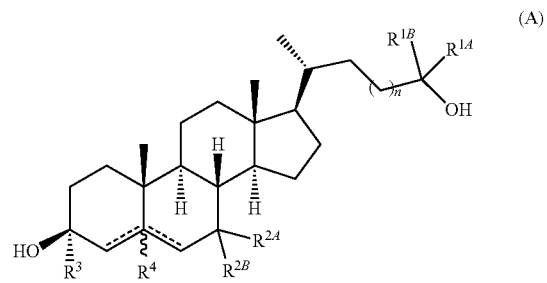

(A)

11 Claims, No Drawings

(56) References Cited

U.S. PATENT DOCUMENTS

| | | |
|---|---|---|
| 10,201,550 B2 | 2/2019 | Salituro et al. |
| 10,227,375 B2 | 3/2019 | Martinez Botella et al. |
| 10,259,840 B2 | 4/2019 | Harrison et al. |
| 10,696,712 B2 | 6/2020 | Salituro et al. |
| 10,723,758 B2 | 7/2020 | Harrison et al. |
| 2004/0048838 A1 | 3/2004 | Gronvald et al. |
| 2005/0101573 A1 | 5/2005 | Faarup et al. |
| 2006/0199790 A1 | 9/2006 | Baulieu et al. |
| 2008/0193423 A1 | 8/2008 | Brunton et al. |
| 2008/0269183 A1 | 10/2008 | Mellon et al. |
| 2008/0319026 A1 | 12/2008 | Gant et al. |
| 2010/0034781 A1 | 2/2010 | Parhami et al. |
| 2010/0087411 A1 | 4/2010 | Barraclough et al. |
| 2011/0160223 A1 | 6/2011 | Dingledine et al. |
| 2011/0190249 A1 | 8/2011 | Rees et al. |
| 2012/0035156 A1 | 2/2012 | Alberati et al. |
| 2012/0040916 A1 | 2/2012 | Moon et al. |
| 2012/0041016 A1 | 2/2012 | Frincke |
| 2012/0115169 A1 | 5/2012 | Mullenix et al. |
| 2013/0210792 A1 | 8/2013 | Song et al. |
| 2014/0045943 A1 | 2/2014 | Khan et al. |
| 2014/0148412 A1 | 5/2014 | Hogenkamp |
| 2014/0235600 A1 | 8/2014 | Covey et al. |
| 2014/0335050 A1 | 11/2014 | Haggerty et al. |
| 2015/0158903 A1 | 6/2015 | Upasani et al. |
| 2015/0291654 A1 | 10/2015 | Upasani et al. |
| 2015/0376225 A1 | 12/2015 | Dugar et al. |
| 2016/0022701 A1 | 1/2016 | Reddy et al. |
| 2016/0031930 A1 | 2/2016 | Martinez Botella et al. |
| 2017/0247405 A1 | 8/2017 | Harrison et al. |
| 2017/0304321 A1 | 10/2017 | Quirk et al. |
| 2017/0305960 A1 | 10/2017 | Botella et al. |
| 2018/0194797 A1 | 7/2018 | Salituro et al. |
| 2018/0200267 A1 | 7/2018 | Salituro et al. |
| 2018/0201643 A1 | 7/2018 | Salituro et al. |
| 2018/0237470 A1 | 8/2018 | Botella et al. |
| 2018/0362573 A1 | 12/2018 | Upasani et al. |
| 2018/0371009 A1 | 12/2018 | Pellicciari et al. |
| 2019/0125764 A1 | 5/2019 | Salituro et al. |
| 2019/0127414 A1 | 5/2019 | Botella et al. |
| 2019/0135854 A1 | 5/2019 | Harrison et al. |
| 2019/0160078 A1 | 5/2019 | Masuoka et al. |
| 2019/0248829 A1 | 8/2019 | Salituro et al. |
| 2019/0330259 A1 | 10/2019 | Robichaud et al. |
| 2019/0359646 A1 | 11/2019 | Botella et al. |
| 2020/0002371 A1 | 1/2020 | Salituro et al. |
| 2020/0123195 A1 | 4/2020 | Salituro et al. |
| 2021/0040138 A1 | 2/2021 | Harrison et al. |
| 2021/0101925 A1 | 4/2021 | Salituro et al. |
| 2021/0145848 A1 | 5/2021 | Salituro et al. |
| 2021/0147468 A1 | 5/2021 | Salituro et al. |
| 2021/0147470 A1 | 5/2021 | Upasani et al. |

FOREIGN PATENT DOCUMENTS

| | | | |
|---|---|---|---|
| FR | 2850023 A1 | 7/2004 | |
| GB | 1564806 | 4/1980 | |
| JP | 50140435 | 11/1975 | |
| JP | 53082766 | 7/1978 | |
| JP | 54163565 | 12/1979 | |
| JP | 57035597 | 2/1982 | |
| JP | 61254599 | 11/1986 | |
| JP | 62187485 | 8/1987 | |
| JP | 8268917 A | 10/1996 | |
| JP | 09328498 | 12/1997 | |
| JP | 2005508368 A | 3/2005 | |
| RU | 2194712 C2 | 12/2002 | |
| WO | WO1980002562 | 11/1980 | |
| WO | 9427608 A1 | 12/1994 | |
| WO | 1995002409 A2 | 1/1995 | |
| WO | 1995021617 A1 | 8/1995 | |
| WO | 9612705 A1 | 5/1996 | |
| WO | WO1996012705 | 5/1996 | |
| WO | WO1996040043 | 12/1996 | |
| WO | 9700884 A1 | 1/1997 | |
| WO | WO1997042215 | 11/1997 | |
| WO | 199905849 | 11/1999 | |
| WO | 2000068246 A1 | 11/2000 | |
| WO | 2001049703 A2 | 7/2001 | |
| WO | 0211708 A2 | 2/2002 | |
| WO | 02053577 A2 | 7/2002 | |
| WO | 2002079221 A2 | 10/2002 | |
| WO | 2003039480 A2 | 5/2003 | |
| WO | 03049685 A2 | 6/2003 | |
| WO | 2003082893 A2 | 10/2003 | |
| WO | 2004055201 A2 | 7/2004 | |
| WO | WO2005079810 | 9/2005 | |
| WO | WO-2005079810 A1 * | 9/2005 | ............ A61K 31/57 |
| WO | 2009001097 A2 | 12/2008 | |
| WO | 2009059961 A2 | 5/2009 | |
| WO | 2009090063 A1 | 7/2009 | |
| WO | 2010075282 A1 | 7/2010 | |
| WO | 2010088414 A2 | 8/2010 | |
| WO | 2011014661 A2 | 2/2011 | |
| WO | 2011028794 A2 | 3/2011 | |
| WO | 2011067501 A1 | 6/2011 | |
| WO | 2012064501 A1 | 5/2012 | |
| WO | 2012142039 A1 | 10/2012 | |
| WO | 2013019711 A2 | 2/2013 | |
| WO | 2013036835 A1 | 3/2013 | |
| WO | WO2013036835 | 3/2013 | |
| WO | 2013056181 A1 | 4/2013 | |
| WO | 2013163455 A2 | 10/2013 | |
| WO | 2014028942 A2 | 2/2014 | |
| WO | 2014115167 A2 | 7/2014 | |
| WO | 2014120786 A1 | 8/2014 | |
| WO | 2014160441 A1 | 10/2014 | |
| WO | 2014160480 A1 | 10/2014 | |
| WO | 2015195967 A1 | 12/2015 | |
| WO | 2016007762 A1 | 1/2016 | |
| WO | 2016057713 A1 | 4/2016 | |
| WO | 2017007832 A1 | 1/2017 | |
| WO | 2017007836 A1 | 1/2017 | |
| WO | 2017007840 A1 | 1/2017 | |
| WO | 2017037465 A1 | 3/2017 | |
| WO | 2018170336 A1 | 9/2018 | |

OTHER PUBLICATIONS

Cecil Textbook of Medicine, 20th edition (1996), vol. 2, pp. 2050-2057.

Citraro et al., "Effects of some neurosteroids injected into some brain areas of WAG/Rij rats, an animal model of generalized absence epilepsy", Neuropharmacology, (2006), vol. 50, No. 8, pp. 1059-1071.

Collingridge, "The NMDA receptor as a target for cognitive enhancement", Neuropharmacology. (2013), pp. 13-26, abstract.

Connick et al., "Program No. 613 1/B86", 2009 Neuroscience Meeting Planner. Chicago, IL: Society for Neuroscience, (2009).

Cook et al., "24-hydroxycholesterol sulfation by human cytosolic sulfotransferases: Formation of monosulfates and disulfates, molecular modeling, sulfatase sensitivity, and inhibition of liver x receptor activation", Drug Metabolism and Disposition, vol. 37, No. 10, (2009), pp. 2069-2078.

Corman et al., "Structure-Activity Relationships for Side Chain Oxysterol Agonists of the Hedgehog Signaling Pathway", ACS Medicinal Chemistry Letters, Aug. 28, 2012, 3, 828-833.

Cross et al., "Steroids CCLXXIN 1. Biologically-Active Labile Ethers IV2. The Synthesis of 22-Oxa-25-Azacholesterol and Related Compounds", Steroids, Elsevier Science Publishers, vol. 5, No. 5, pp. 585-598, (1965).

Database Chemical Abstracts Service, Xiangdong et al. "Highly stereoselective synthesis of 24R,25- and 24S, 25-dihydroxysteroid", Database acession No. 2001:174431, (2000).

Dayal et al., "Stereospecific synthesis of 3b-hydroxylated bile alcohols", Journal of Lipid Research, vol. 25, No. 6, (1984), pp. 646-650.

Extended European Search Report for Application No. 15809462.3 dated Nov. 29, 2017.

Extended European Search Report for Application No. 16821920.2 dated Jan. 31, 2019.

(56) References Cited

OTHER PUBLICATIONS

Extended European Search Report for Application No. 16821924.4 dated Jan. 31, 2019.
Extended European Search Report for Application No. 16821926.9 dated Jan. 31, 2019.
Extended European Search Report for European Application No. 14775126.7, dated 2017.
Extended European Search Report for European Application No. 15849514.3 dated May 23, 2018.
Extended European Search Report for PCTUS2014/026784 dated Aug. 17, 2016.
FDA mulls drug to slow late-stage Alzheimer's [online], [retrieved on Sep. 23, 2003]. Retrieved from the Internet, URL; http://www.cnn.com/2003/HEALTH/conditions/09/24/alzheimers.drug.ap/indexhtml>.
Festa et al., "Exploitation of Cholane Scaffold for the Discovery of Potent and Selective Farnesoid X Receptor (FXR) and G-Protein Coupled Bile Acid Receptor 1 (GP-BAR1) Ligands", Journal of Medicinal Chemistry, vol. 57, No. 20, (2014), pp. 8477-8495.
Foster et al., "Effect of steroids on 13-adrenoceptor-mediated relaxation of pig bronchus", Br. J. Pharmac. vol. 78, 1983, pp. 441-445.
Golub et al., "Molecular classification of cancer: Class discovery and class prediction by gene expression monitoring", Science (1999), vol. 286, pp. 531-537.
Gunatilaka et al., "Bioactive Ergost-5-ENE-3b, 7a-DIOL Derivatives from Pseudobersama Mossambicensis", Journal of Natural Products, vol. 55, No. 11, (1992), pp. 1648-1654.
Hoffmeister et al., "Zur Chemie des Ecdysons, III: Vergleichende spektrometrische Untersuchungen an a.b-ungesättigten Steroidketonen", Chemische Berichte, (1965), vol. 98, pp. 2361-2375.
Iida et al., "An improved method for the capillary gas chromatographic derivatization of polyhydroxylated steroids having tert-hydroxyl groups", Analytical Sciences, 2003. vol. 19, pp. 1317-1321.
International Search Report and Written Opinion for corresponding International Application No. PCT/US14/26633 dated Jul. 14, 2014.
International Search Report and Written Opinion for corresponding International Application No. PCT/US15/36510 dated Sep. 15, 2015.
International Search Report and Written Opinion for corresponding International Application No. PCT/US17/25535 dated Jul. 3, 2017.
International Search Report and Written Opinion for corresponding International Application No. PCT/US17/31374 dated Jul. 17, 2017.
International Search Report and Written Opinion for corresponding International Application No. PCT/US2012/054261 dated Nov. 28, 2012.
International Search Report and Written Opinion for corresponding International Application No. PCT/US2014/026784 dated Jul. 8, 2014.
International Search Report and Written Opinion for corresponding International Application No. PCT/US2015/054551 dated Jan. 8, 2016.
International Search Report and Written Opinion for corresponding International Application No. PCT/US2016/041160 dated Oct. 28, 2016.
International Search Report and Written Opinion for corresponding International Application No. PCT/US2016/041168 dated Sep. 15, 2016.
International Search Report and Written Opinion for corresponding International Application No. PCT/US2016/041175 dated Sep. 16, 2016.
International Search Report and Written Opinion for corresponding International Application No. PCT/US2017/041199 dated Aug. 29, 2017.
International Search Report and Written Opinion for corresponding International Application No. PCT/US2017/054657 dated Nov. 21, 2017.
International Search Report and Written Opinion for corresponding International Application No. PCT/US2017/057276 dated Nov. 12, 2017.
International Search Report and Written Opinion for corresponding International Application No. PCT/US2017/057277 dated Feb. 20, 2018.
Karaki et al., "Structure-activity relationship studies of Niemann-Pick type C1-like 1 (NPC1L1) ligands identified by screening assay monitoring pharmacological chaperone effect", Bioorganic & Medicinal Chemistry, vol. 21, Issue 17, (2013), pp. 5297-5309.
Khripach et al., "Synthesis of (24S)-Hydroxy- and (24S)-24,25-Epoxycholesterol Analogues, Potential Agonists of Nuclear LXR Receptors", Russian Journal of Bioorganic Chemistry, Kluwer Academic Publishers—Plenum Publishers, NE, vol. 32, No. 6, pp. 586-594, (2006).
Knoppert et al., "Position Paper: Paediatric Age Categories to be Used in Differentiating Between Listing on a Model Essential Medicines List for Children", 2007, pp. 1-5.
Kurosawa et al., "Synthesis of 19-Hydroxylated Bile Acids and Identification of 3a,7a,12a,19-Tetrahydroxy-5b-cholan-24oic Acid in Human Neonatal Urine" 1995, Chem. Pharm. Bull, vol. 43, No. 9, pp. 1551-1557.
Lakhan et al., "Frontiers in Psychiatry, NMDA receptor activity in neuropsychiatric disorders", 2013, pp. 1-7.
Lala et al., "Role of nitric oxide in tumor progression: Lessons from experimental tumors", Cancer and Metastasis Reviews, (1998), 17 (1), pp. 91-106.
Leoni et al., "Oxysterols as biomarkers in neurodegenerative diseases", Chemistry and Physics of Lipids, vol. 164 (2011), pp. 515-524.
Lettré, et al., "Mehrwertige Alkohole aus Sterinen und Sterinderivaten, VI Steroide mit Strukturmerkmalen des Ecdysons und der Elatericine", Justus Liebigs Annalen der Chemie, (1972), vol. 758, pp. 89-110. English Abstract.
Li et al., "Synthesis of 7a-hydroxy derivatives of regulatory oxysterols", Steroids, vol. 65, No. 9, (2000), pp. 529-535.
Linsenbardt et al., "Different oxysterols have opposing actionss at N-methyl-d-aspartate receptors", Neuropharmacology., vol. 85 (2014), pp. 232-242.
Luu et al., "Oxysterols: Old Tale, New Twists", Annual Reviews. Pharmacol. Toxicol. (2016), vol. 56, pp. 447-467.
Mateos et al., "Activity-regulated cytoskeleton-associated protein in rodent brain is down regulated by high fat diet in vivo and by 27-hydroxycholesterol in vitro", Brain Pathology. vol. 19, No. 1, (2009), pp. 69-80.
Mouriño et al., "Studies on vitamin D (calciferol) and its analogs. 15.24-Nor-1a.,25-dihydroxyvitamin D3 and 24-nor-25-hydroxy-5,6-trans-vitamin D3", J. Med. Chem., (1978), vol. 21, No. 10, pp. 1025-1029.
Nagano et al., "Chemistry and Biochemistry of Chinese Drugs. Part II. Hydroxylated Sterols, Cytotoxic Towards Cancerous Cells: Synthesis and Testing", Journal of Chemical Research, vol. 9, pp. 218 (1977).
Olkkonen et al., "Oxysterols and Their Cellular Effectors", Biomolecules, vol. 2 (2012), pp. 76-103.
Park-Chung et al., "Distinct sites for inverse modulation of N-methyl-D-aspartate receptors by sulfated steroids", Molecular Pharmacology, vol. 52, No. 6, (1997), pp. 1113-1123.
Partial International Search Report and Provisional Opinion for corresponding Internation Application No. PCT/US2017/057277 dated Dec. 20, 2017.
Partial Supplementary European Search Report for European Application No. 14775126.7 dated Sep. 14, 2016.
Paul et al., "The Major Brain Cholesterol Metabolite 24 (S)-Hydroxycholesterol Is a Potent Allosteric Modulator of N-Methyl-D-Aspartate Receptors", Journal of Neuroscience, vol. 33, No. 44, pp. 17290-17300, (2013).
Pubchem, 25-Hydroxycholesterol, CID 65094, pp. 1-6, 2005.
Pubchem, CID 132021, pp. 1-15, 2005.
Pubchem, CID 54083335, pp. 1-3, 2011.
Pubchem, CID 54160779, pp. 1-3, 2011.
Pubchem, CID 58455549, pp. 1-4, 2012.
Pubchem, CID 66966798, pp. 1-3, 2012.
Pubchem, CID 70604305, pp. 1-3, 2012.
Pubchem, CID 71508953, pp. 1-13, 2013.

(56) References Cited

OTHER PUBLICATIONS

Reddy, "Pharmacology of endogenous neuroactive steroids, Crit Rev Neurobiol", 2003;15(3-4) pp. 197-234.
Schmidt et al., "Inhibitory effect of oxygenated cholestan-3b-ol derivatives on the growth of *Mycobacterium tuberculosis*", Bioorganic & Medicinal Chemistry Letters, vol. 23, No. 22, (2013), pp. 6111-6113.
Sepe et al., "Total Synthesis and Pharmacological Characterization of Solomonsterol A, a Potent Marine Pregnane-X-Receptor Agonist Endowed with Anti-Inflammatory Activity", Journal of Medicinal Chemistry, vol. 54, (2011), pp. 4590-4599.
Stamp et al., "Plasma Levels and Therapeutic Effect of 25-Hydroxycholecalciferol in Epileptic Patients taking Anticonvulsant Drugs", British Medical Journal, vol. 4, 1972, pp. 9-12.
Stastna et al., "Synthesis of C3, C5, and C7 pregnane derivatives and their effect on NMDA receptor responses in cultured rat hippocampal neurons", Steroids, Elsevier Science Publishers, vol. 74, No. 2, (2008), pp. 256-263.
Steinrauf et al., "Synthesis and Evaluation of Sulfur-Containing Steroids Against Methylmercuric Chloride Toxicity", Journal of Pharmaceutical Sciences, vol. 67, No. 12, pp. 1739-1743, (1978).
Svoboda et al. (Am J Med Genet C Semin Med Genet (2012), pp. 285-294) (Year: 2012).
Takano et al., "Simple Synthesis of 3b, 24-Dihydroxychol-5-EN-7-ONE by Oxidative Cleavage of the Side Chain of Cholesterol", Chemistry Letters, vol. 14, No. 8, (1985), pp. 1265-1266.
Tierney et al., "Abnormalities of Cholesterol Metabolism in Autism Spectrum Disorders", Am J Med Genet B Neuropsychiatr Genet. vol. 141B, No. 6, (2006), pp. 666-668.
Tomek et al., "NMDA Receptor Modulators in the Treatment of Drug Addiction", Pharmaceuticals (Basel), 2013, vol. 6, No. 2, pp. 251-258.
Vincent Chen et al., "The chemical biology of clinicall tolerated NMDA receptor antagonists", Journal of Neurochemistry, (2006), pp. 1611-1626.
Wolozin et al., "The Cellular Biochemistry of Cholesterol and Statins: Insights into the Pathophysiology and Therapy of Alzheimer's Disease" vol. 10, No. 2, 2004, pp. 127-146.
Wong et al., An efficient and convenient transformation of a-haloketones to a-hydroxyketones using cesium formate. Journal of Organometallic Chemistry 2006, 694, 3452-3455.
Xilouri et al., "Neuroprotective effects of steroid analogues on P19-N neurons", Neurochemistry International, (2007), vol. 50, No. 4, pp. 660-670.
Yan et al., "Characterization of a synthetic steroid 24-keto-cholest-5-en-3b, 19-diol as a neuroprotectant", CNS Neuroscience & Therapeutics, vol. 21, No. 6, (2015), pp. 486-495.
Yang et al., "New cytotoxic oxygenated sterols from marine bryozoan Bugula neritina", Natural Product Research, vol. 25, No. 16, (2011), pp. 1505-1511.
Yoon-Seok et al., "Neuroprotective Effects of Ginsenoside Rg3 against 24-0H-cholesterol-induced Cytotoxicity in Cortical Neurons", Journal of Ginseng Research, vol. 34, No. 3, pp. 246-253, (2010).
Zuliani et al., "Plasma 24S-hydroxycholesterol levels in elderly subjects with late onset Alzheimer's disease or vascular dementia: a case-control study" BMC Neurology, vol. 11, No. 121, pp. 1-8, (2011).
Elbarbry et al., "Cyclosporine-induced changes in drug metabolizing enzymes in hyperlipemic rabbit kidneys could explain its toxicity," Synthetic Communications, 40(11):772-781 (2010).
Meljon et al., "Analysis by liquid chromatography-mass spectrometry of sterols and oxysterols in brain of the newborn Dhcr7(Δ3-5/T93M) mouse: a model of Smith-Lemli-Opitz syndrome," Biochemical Pharmacology, 86:43-55 (2013).
Registry (STN) [online] CAS Registration No. 1392266-35-1; 13392266-34-0; 1271523-00-2; 185138-08-3; 185138-00-5; 1851387-82-0; 66450-87-1 (2012).
Berge et al., "Pharmaceutical salts," Journal of Pharmaceutical Sciences, 66(1): 1-19 (1977).

Cais et al., "Temperature dependence of NR1/NR2B NMDA receptor channels," Neuroscience, 151(2):428-438 (2008).
Costa et al., "A novel family of negative and positive allosteric modulators of NMDA receptors," Journal of Pharmacology and Experimental Therapeutics, 335(3):614-21 (2010).
Dale et al., "Nuclear magnetic resonance enantiomer regents. Configurational correlations via nuclear magnetic resonance chemical shifts of diastereomeric mandelate, 0-methylmandelate, and .alpha.-methoxy-.alpha.-trifluoromethylphenylacetate (M'IPA) esters," Journal of the American Chemical Society, 95(2):512-519 (1973).
Fukuto et al., "Determination of the Mechanism of Demethylenation of (methylenedioxy)phenyl compounds by cytochrome P450 using deuterium isotope effects," Journal of Medicinal Chemistry, 34(9):2871-2876 (1991).
Gee et al., "GABA-dependent modulation of the Cl- ionophore by steroids in rat brain," European Journal of Pharmacology, 136(3):419-423 (1987).
Groden et al., "Determination of Fura-2 dissociation constants following adjustment of the apparent Ca-EGTA association constant for temperature and ionic strength," Cell Calcium, 12:(4)279-287 (1991).
GRYNKIEWICZ et at., "A new generation of Ca2+ indicators with greatly improved fluorescence properties," Journal of Biological Chemistry, 260(6):3440-3345 (1985).
Guthrie et al., "Morphological and biochemical differences expressed in separate dissociated cell cultures of dorsal and ventral halves of the mouse spinal cord," Brain Research, 420(2):313-323 (1987).
Hoeve et al., "The design of resolving agents. Chiral cyclic phosphoric acids," Journal of Organic Chemistry, 50(23):4508-4514 (1985).
Hogg et al., "An automated system for intracellular and intranuclear injection," Journal of Neuroscience, Methods, 169(l):65-75 (2008).
Hollmann et al., "Zinc potentiates agonist-induced currents at certain splice variants of the NMDA receptor," Neuron, 10(5):943-954 (1993).
Horak et al., "Molecular mechanism of pregnenolone sulfate action at NR1/NR2B receptors," Journal of Neuroscience, 24(46): 10318-10325 (2004).
Huttunen et al., "Prodrugs-from serendipity to rational design," Pharmacological Reviews, 63(3):750-771 (2011).
Irwin et al., "Steroid potentiation and inhibition of N-methyl-D-aspartate receptor-mediated intracellular Ca++ responses: structure-activity studies," Journal of Pharmacology and Experimental Therapeutics, 271(2):677-682 (1994).
Jurman et al., "Visual identification of individual transfected cells for electrophysiology using antibody-coated beads," Biotechniques, 17(5):876-881 (1994).
Lutjohann et al., "Cholesterol homeostasis in human brain: evidence for an agedependent flux of 24S-hydroxycholesterol from the brain into the circulation," PNAS, 93(18):9799-804 (1996).
Madau et al., Program No. 613.2/B87. 2009 Neuroscience Meeting Planner. Chicago, IL: Society for Neuroscience (2009) (3 pages).
Monyer et al., "Heteromeric NMDA receptors: molecular and functional distinction of subtypes," Science, 256(5060):1217-1221 (1992).
Nagasaka et al., "Oxysterol changes along with cholesterol and vitamin D changes in adult phenylketonuric patients diagnosed by newborn mass-screening," Clinica Chimica Acta, 416:54-59 (2013).
Petrovic et al., "Pregnenolone sulfate modulation of N-methyl-D-aspartate receptors is phosphorylation dependent," Neuroscience, 160:616-628 (2009).
Pritchett et al., "Transient expression shows ligand gating and allosteric potentiation of GABAA receptor subunits," Science, 242(4883): 1306-1308 (1988).
Segal, "Pat hippocampal Neurons in Culture: Responses to Electrical and Chemical Stimuli," Journal of Neurophysiology, 50(6): 1249-1264 (1983).
Takahashi et al., "Stereochemistry of reduction of the C-24,25 double bond in the conversion of desmosterol into cholesterol," Tetrahedron Letters, 44(2):341-344 (2003).
Verdoorn et al., "Functional properties of recombinant rat GABAA receptors depend upon subunit composition," Neuron, 4(6):919-928 (1990).

(56) References Cited

OTHER PUBLICATIONS

Vyklicky et al., "Calcium-mediated modulation of N-methyl-D-aspartate (NMDA) responses in cultured rat hippocampal neurones," Journal of Physiology, 470:575-600 (1993).

Wieland et al., "Comparative behavioral characterization of the neuroactive steroids 3 alpha-OH,5 alpha-pregnan-20-one and 3 alpha-OH,5 beta-pregnan-20-one in rodents," Psychopharmacology 118(1):65-71 (1995).

Wilen et al., "Strategies in Optical Resolutions," Tetrahedron 33:2725-2736 (1977).

Zhou et al., "Properties of HERG channels stably expressed in HEK 293 cells studied at physiological temperature," Biophysical Journal, 74(1):230-241 (1998).

* cited by examiner

C7 SUBSTITUTED OXYSTEROLS AND METHODS OF USE THEREOF

RELATED APPLICATIONS

The present application is a U.S. National Phase Application under 35 U.S.C. § 371 of International Application PCT/US2017/054657, filed Sep. 30, 2017, which claims priority to and the benefit of U.S. Provisional Application No. 62/402,789 filed Sep. 30, 2016 and U.S. Provisional Application No. 62/402,797 filed Sep. 30, 2016, each of which are incorporated herein by reference in their entirety.

BACKGROUND OF THE INVENTION

NMDA receptors are heteromeric complexes comprised of NR1, NR2, and/or NR3 subunits and possess distinct recognition sites for exogenous and endogenous ligands. These recognition sites include binding sites for glycine, and glutamate agonists and modulators. NMDA receptors are expressed in the peripheral tissues and the CNS, where they are involved in excitatory synaptic transmission. Activating these receptors contributes to synaptic plasticity in some circumstances and excitotoxicity in others. These receptors are ligand-gated ion channels that admit $Ca^{2+}$ after binding of the glutamate and glycine, and are fundamental to excitatory neurotransmission and normal CNS function. Positive modulators may be useful as therapeutic agents with potential clinical uses as cognitive enhancers and in the treatment of psychiatric disorders in which glutamatergic transmission is reduced or defective (see, e.g., Horak et al., J. of Neuroscience, 2004, 24(46), 10318-10325). In contrast, negative modulators may be useful as therapeutic agents with potential clinical uses in the treatment of psychiatric disorders in which glutamatergic transmission is pathologically increased (e.g., treatment resistant depression).

Oxy sterols are cholesterol analogs that are modulators of NMDA receptor function. There is a need for new oxysterols that modulate the NMDA receptor for the prevention and treatment of conditions associated with NMDA expression and function. Compounds, compositions, and methods described herein are directed toward this end.

SUMMARY OF THE INVENTION

Provided herein are substituted oxysterols useful for preventing and/or treating a broad range of disorders, including, but not limited to, NMDA-mediated disorders. Further provided are pharmaceutical compositions comprising the compounds of the present invention, and methods of their use and treatment.

In one aspect, provided herein are compounds according to Formula (A):

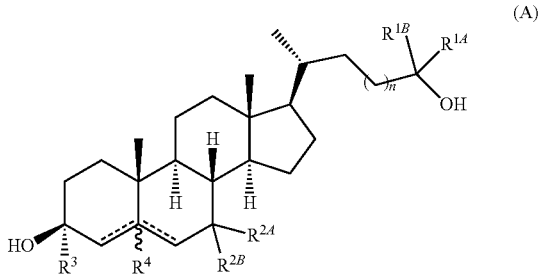

or a pharmaceutically acceptable salt thereof, wherein:

each of $R^{1A}$ and $R^{1B}$ is independently hydrogen, substituted or unsubstituted alkyl, carbocyclyl, heterocyclyl, aryl, or heteroaryl, or $R^{1A}$ and $R^{1B}$, together with the carbon atom to which they are attached form a 3-8 membered ring;

n is 1 or 2;

each of $R^{2A}$ and $R^{2B}$ is independently hydrogen, halo, $-OR^C$, alkyl, alkenyl, alkynyl, aryl, or heteroaryl, wherein $R^C$ is hydrogen or alkyl, or $R^{2A}$ and $R^{2B}$, together with the carbon atom to which they are attached form an oxo group, wherein $R^{2A}$ and $R^{2B}$ are not both simultaneously hydrogen;

$R^3$ is hydrogen, alkyl, alkenyl, alkynyl, or $-OR^4$, wherein $R^4$ is alkyl;

$R^4$ is absent or hydrogen; and

═ represents a single or double bond, wherein when one of ═ is a double bond, the other ═ is a single bond; when both of ═ are single bonds, then $R^4$ is hydrogen; and when one of the ═ is a double bond, $R^4$ is absent.

In some embodiments, n is 1. In other embodiments, n is 2.

In some embodiments, when $R^{1A}$, $R^3$, and $R^4$ are hydrogen and $R^{1B}$ is unsubstituted isopropyl, then $R^{2A}$ and $R^{2B}$, together with the carbon atom to which they are attached do not form an oxo group; and when $R^4$ is absent, $R^3$ is hydrogen, and $R^{1A}$ and $R^{1B}$ are $-CH_3$, then $R^{2A}$ is not $-CH_3$ and $R^{2B}$ is not $-OH$. In further embodiments, n is 1.

In some embodiments, when $R^4$ is absent, $R^{2A}$ is $-OH$, $R^{2B}$ is hydrogen or $-CF_3$, and $R^{1A}$ and $R^{1B}$ are $-CH_3$, then $R^3$ is not hydrogen; and when $R^{1A}$ and $R^{1B}$ are $-CH_3$ and $R^3$ is hydrogen, then $R^{2A}$ and $R^{2B}$, together with the carbon atom to which they are attached do not form an oxo group. In further embodiments, n is 2.

In some embodiments, wherein the compound of Formula (A) is a compound of Formula (A-I):

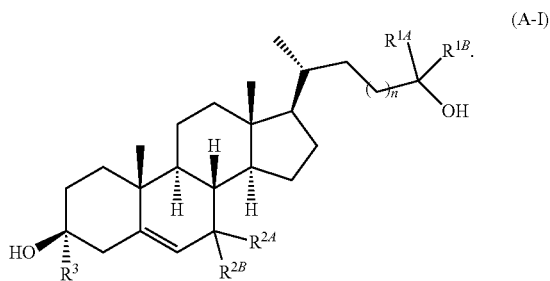

In some embodiments, the compound of Formula (A) is a compound of Formula (A-II):

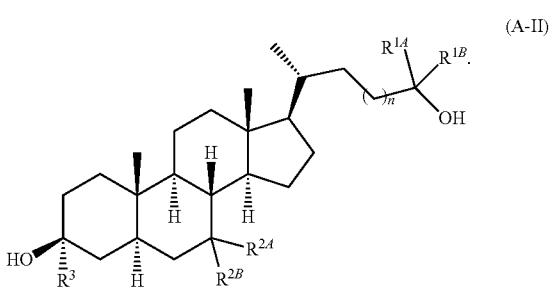

In some embodiments, the compound of Formula (A) is a compound of Formula (A-III):

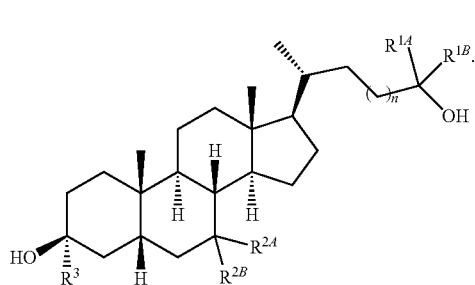

In some embodiments, the compound of Formula (A) is a compound of Formula (A-IV), (A-V), (A-VI):

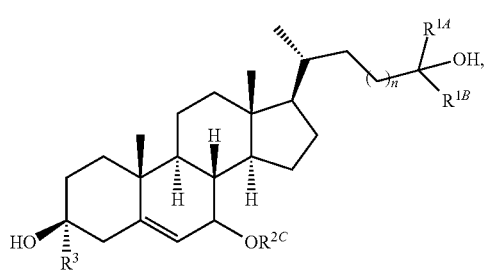

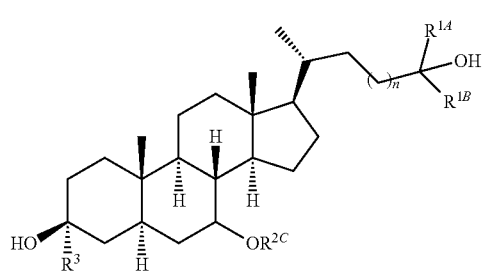

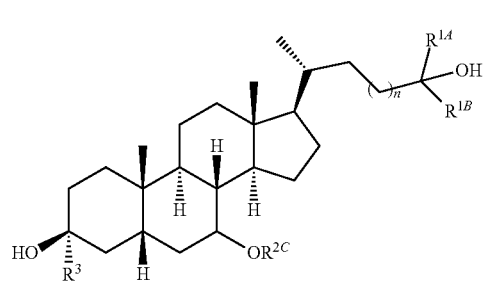

wherein $R^{2C}$ is hydrogen or alkyl and $R^3$ is alkyl, alkenyl, alkynyl, or —$OR^A$, wherein $R^A$ is alkyl.

In some embodiments, the compound of Formula (A) is a compound of Formula (A-VII), (A-VIII), or (A-IX):

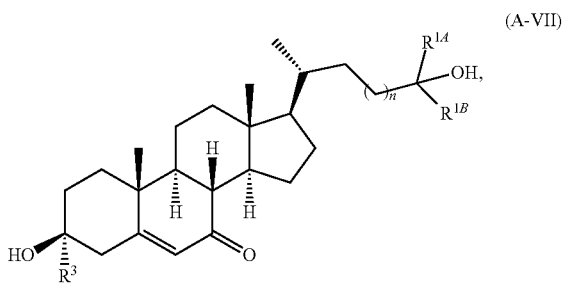

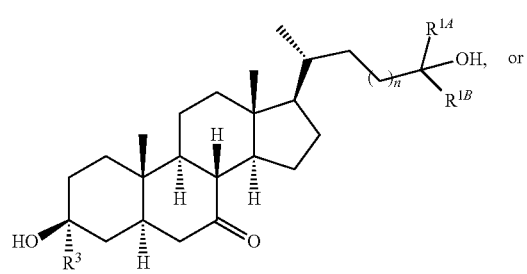

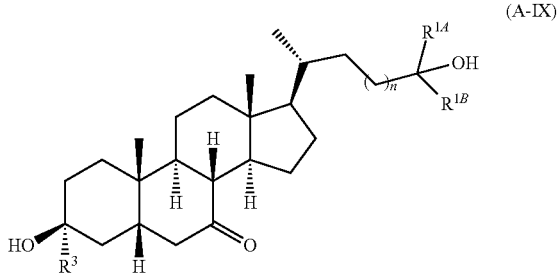

wherein $R^3$ is alkyl, alkenyl, alkynyl, or —$OR^A$, wherein $R^A$ is alkyl.

In some embodiments, the compound of Formula (A) is a compound of Formula (A-XII):

(A-X)

wherein $R^3$ is alkyl, alkenyl, alkynyl, or —$OR^A$, wherein $R^A$ is alkyl.

In some embodiments, the compound of Formula (A) is a compound of Formula (A-XII)

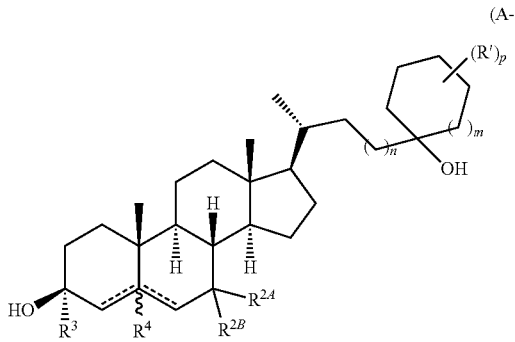

(A-XII)

where R' is alkyl or —OR$^A$, wherein R$^A$ is hydrogen or alkyl; p is 0, 1, 2, 3, 4, 5, or 6; and m is 0, 1, 2, or 3.

In some embodiments, R$^4$ is absent, one of R$^{2A}$ and R$^{2B}$ is —OH, and R$^3$ is not hydrogen.

In some embodiments, each of R$^{1A}$ and R$^{1B}$ is independently unsubstituted or substituted alkyl (e.g., haloalkyl, alkoxyalkyl, —CH$_3$, —CH$_2$CH$_3$, —CH(CH$_3$)$_2$, —CF$_3$ or —CH$_2$OCH$_3$).

In other embodiments, each of R$^{1A}$ and R$^{1B}$ is independently substituted alkyl (e.g., haloalkyl). In some embodiments, R$^{1A}$ and R$^{1B}$ is alkyl (e.g., unsubstituted or substituted alkyl (e.g., —CH$_3$)). In some embodiments, R$^{1A}$ and R$^{1B}$ are —CH$_3$.

In some aspects, R$^{1A}$ is —CF$_3$ or —CH$_2$OCH$_3$.

In other aspects, R$^{1A}$ is hydrogen and R$^{1B}$ is alkyl, carbocyclyl, heterocyclyl, aryl, or heteroaryl.

In some embodiments, R$^{1A}$ and R$^{1B}$, together with the carbon atom to which they are attached form a 3-8 membered ring.

In some aspects, R$^{1A}$ is substituted alkyl or unsubstituted C$_2$-C$_6$ alkyl and R$^{1B}$ is substituted or unsubstituted C$_1$-C$_6$ alkyl.

In some embodiments, each of R$^{2A}$ and R$^{2B}$ is independently alkyl (e.g., substituted or unsubstituted alkyl). In some aspects, each of R$^{2A}$ and R$^{2B}$ is independently —F.

In other embodiments, R$^{2A}$ and R$^{2B}$ are —CH$_3$ and R$^3$ is alkyl, alkenyl, alkynyl, or —OR$^A$, wherein R$^A$ is alkyl. In some other embodiments, each of R$^{2A}$ and R$^{2B}$ is independently hydrogen and R$^3$ is alkyl (e.g., substituted or unsubstituted alkyl).

In some embodiments, wherein R$^3$ is alkyl (e.g., substituted or unsubstituted alkyl), alkenyl, alkynyl, or —OR$^A$, wherein R$^A$ is alkyl. In other embodiments, R$^3$ is alkyl (e.g, substituted or unsubstituted alkyl).

In one aspect, provided herein are compounds according to Formula (B):

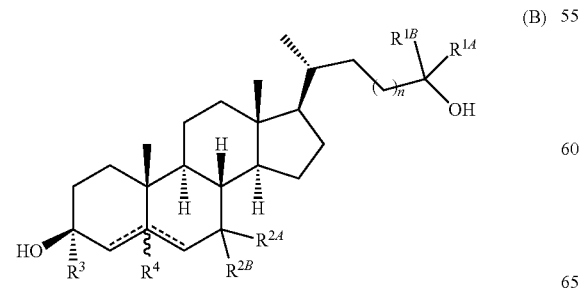

(B)

or a pharmaceutically acceptable salt thereof, wherein:

each of R$^{1A}$ and R$^{1B}$ is independently hydrogen, substituted or unsubstituted alkyl, carbocyclyl, heterocyclyl, aryl, or heteroaryl, or R$^{1A}$ and R$^{1B}$, together with the carbon atom to which they are attached form a 3-8 membered ring;

n is 1 or 2;

each of R$^{2A}$ and R$^{2B}$ is independently hydrogen, halo, —OR$^C$, alkyl, alkenyl, alkynyl, aryl, or heteroaryl, wherein R$^C$ is hydrogen or alkyl, or R$^{2A}$ and R$^{2B}$, together with the carbon atom to which they are attached form an oxo group, wherein R$^{2A}$ and R$^{2B}$ are not both simultaneously hydrogen;

R$^3$ is alkyl, alkenyl, alkynyl, or —OR$^A$, wherein R$^A$ is alkyl;

R$^4$ is absent or hydrogen; and

═══ represents a single or double bond, wherein when one of ═══ is a double bond, the other ═══ is a single bond; when both of ═══ are single bonds, then R$^4$ is hydrogen; and when one of the ═══ is a double bond, R$^4$ is absent.

In some embodiments, n is 1. In other embodiments, n is 2.

In some embodiments, wherein the compound of Formula (B) is a compound of Formula (B-I):

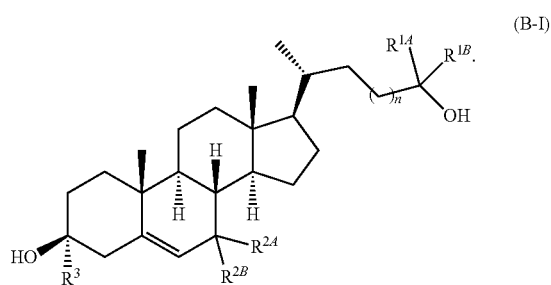

(B-I)

In some embodiments, the compound of Formula (B) is a compound of Formula (B-II):

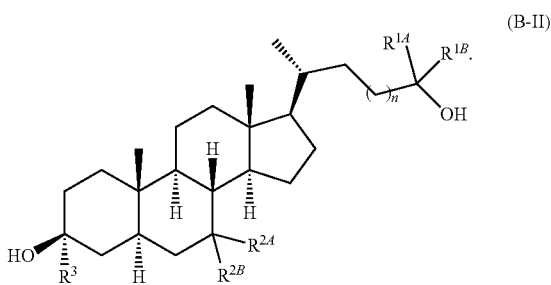

(B-II)

In some embodiments, the compound of Formula (B) is a compound of Formula (B-III):

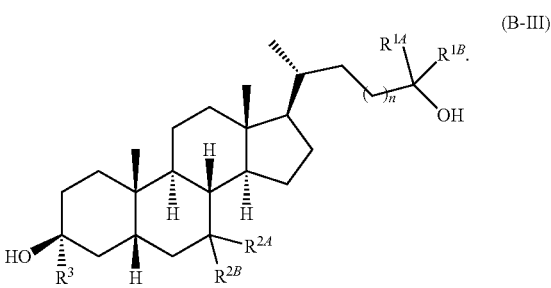

(B-III)

In some embodiments, the compound of Formula (B) is a compound of Formula (B-IV), (B-V), or (B-VI):

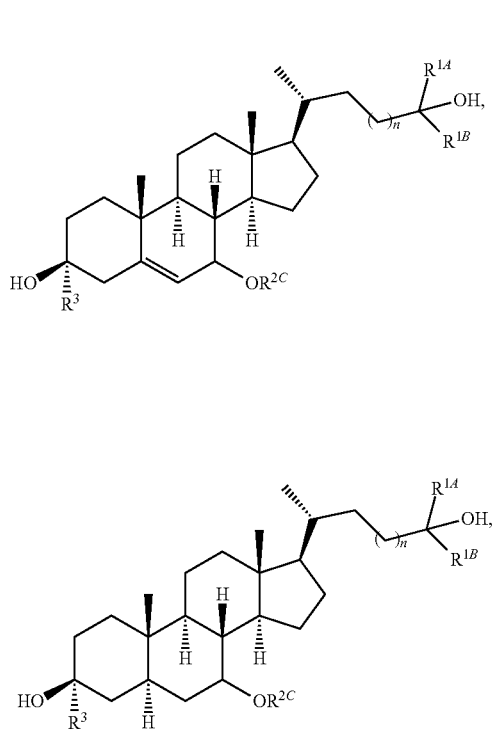

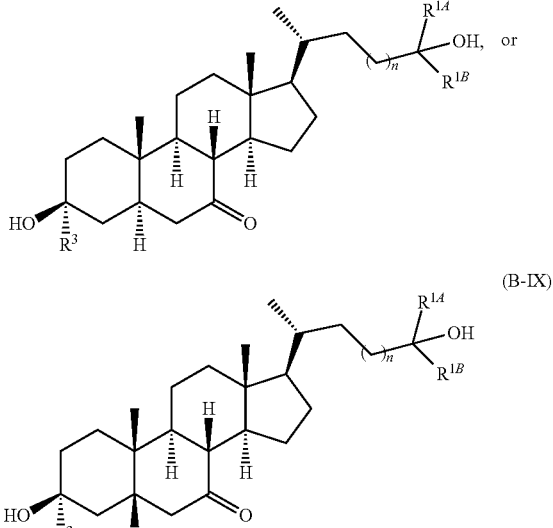

wherein $R^{2C}$ is hydrogen or alkyl and $R^3$ is alkyl, alkenyl, alkynyl, or —$OR^A$, wherein $R^A$ is alkyl.

In some embodiments, the compound of Formula (B) is a compound of Formula (B-VII), (B-VIII), or (B-IX):

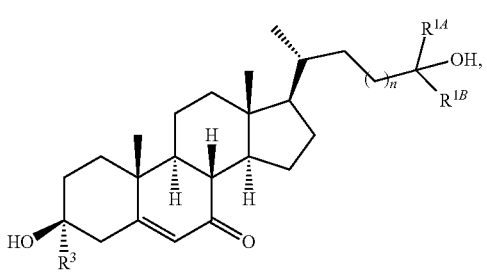

wherein $R^3$ is alkyl, alkenyl, alkynyl, or —$OR^A$, wherein $R^A$ is alkyl.

In some embodiments, the compound of Formula (B) is a compound of Formula (B-X):

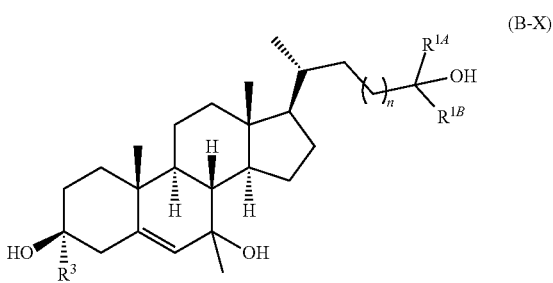

wherein $R^3$ is alkyl, alkenyl, alkynyl, or —$OR^A$, wherein $R^A$ is alkyl.

In some embodiments, the compound of Formula (B) is a compound of Formula (B-XII)

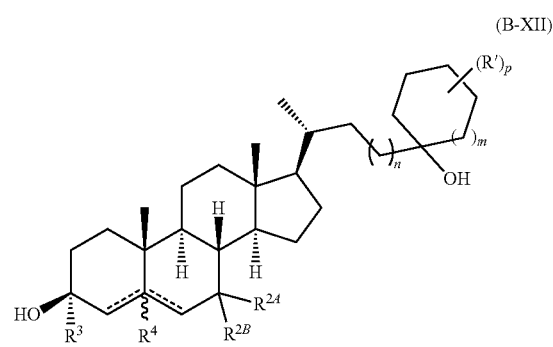

where R' is alkyl or —$OR^A$, wherein $R^A$ is hydrogen or alkyl; p is 0, 1, 2, 3, 4, 5, or 6; and m is 0, 1, 2, or 3.

In some embodiments, each of $R^{1A}$ and $R^{1B}$ is independently unsubstituted or substituted alkyl (e.g., haloalkyl, alkoxyalkyl, —CH$_3$, —CH$_2$CH$_3$, —CH(CH$_3$)$_2$, —CF$_3$ or —CH$_2$OCH$_3$).

In other embodiments, each of $R^{1A}$ and $R^{1B}$ is independently substituted alkyl (e.g., haloalkyl). In some embodiments, $R^{1A}$ and $R^{1B}$ is alkyl (e.g, unsubstituted or substituted alkyl (e.g., —CH$_3$)). In some embodiments, $R^{1A}$ and $R^{1B}$ are —CH$_3$.

In some aspects, $R^{1A}$ is —CF$_3$ or —CH$_2$OCH$_3$.

In other aspects, $R^{1A}$ is hydrogen and $R^{1B}$ is alkyl, carbocyclyl, heterocyclyl, aryl, or heteroaryl.

In some embodiments, $R^{1A}$ and $R^{1B}$, together with the carbon atom to which they are attached form a 3-8 membered ring.

In some aspects, $R^{1A}$ is substituted alkyl or unsubstituted C$_2$-C$_6$ alkyl and $R^{1B}$ is substituted or unsubstituted C$_1$-C$_6$ alkyl.

In some embodiments, each of $R^{2A}$ and $R^{2B}$ is independently alkyl (e.g, substituted or unsubstituted alkyl). In some aspects, each of $R^{2A}$ and $R^{2B}$ is independently —F.

In other embodiments, $R^{2A}$ and $R^{2B}$ are —CH$_3$ and $R^3$ is alkyl, alkenyl, alkynyl, or —OR$^4$, wherein $R^4$ is alkyl. In some other embodiments, each of $R^{2A}$ and $R^{2B}$ is independently hydrogen and $R^3$ is alkyl (e.g., substituted or unsubstituted alkyl).

In some embodiments, wherein $R^3$ is alkyl (e.g, substituted or unsubstituted alkyl), alkenyl, alkynyl, or —OR$^4$, wherein $R^4$ is alkyl. In other embodiments, $R^3$ is alkyl (e.g, substituted or unsubstituted alkyl).

In one aspect, provided herein are compounds according to Formula (I).

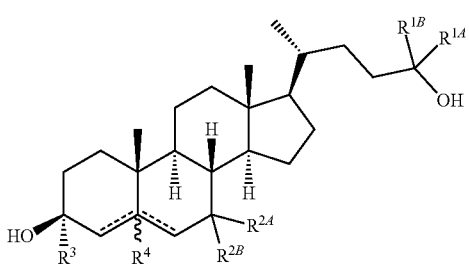

(I)

or a pharmaceutically acceptable salt thereof, wherein:
each of $R^{1A}$ and $R^{1B}$ is independently hydrogen, substituted or unsubstituted alkyl, carbocyclyl, heterocyclyl, aryl, or heteroaryl, or $R^{1A}$ and $R^{1B}$, together with the carbon atom to which they are attached form a 3-8 membered ring;
each of $R^{2A}$ and $R^{2B}$ is independently hydrogen, halo, —OR$^C$, alkyl, alkenyl, alkynyl, aryl, or heteroaryl, wherein $R^C$ is hydrogen or alkyl, or $R^{2A}$ and $R^{2B}$, together with the carbon atom to which they are attached form an oxo group, wherein $R^{2A}$ and $R^{2B}$ are not both simultaneously hydrogen;
$R^3$ is hydrogen, alkyl, alkenyl, alkynyl, or —OR$^4$, wherein $R^4$ is alkyl;
$R^4$ is absent or hydrogen; and
═══ represents a single or double bond, wherein when one of ═══ is a double bond, the other ═══ is a single bond; when both of ═══ are single bonds, then $R^4$ is hydrogen; and when one of the ═══ is a double bond, $R^4$ is absent;
wherein when $R^{1A}$, $R^3$, and $R^4$ are hydrogen and $R^{1B}$ is unsubstituted isopropyl, then $R^{2A}$ and $R^{2B}$, together with the carbon atom to which they are attached do not form an oxo group; and
when $R^4$ is absent, $R^3$ is hydrogen, and $R^{1A}$ and $R^{1B}$ are —CH$_3$, then $R^{2A}$ is not —CH$_3$ and $R^{2B}$ is not —OH.

In some embodiments, $R^{1A}$, $R^3$, and $R^4$ are hydrogen, $R^{1B}$ is unsubstituted isopropyl, and $R^{2A}$ and $R^{2B}$, together with the carbon atom to which they are attached do not form an oxo group.

In some embodiments, $R^4$ is absent, $R^3$ is hydrogen, $R^{1A}$ and $R^{1B}$ are —CH$_3$, $R^{2A}$ is not —CH$_3$, and $R^{2B}$ is not —OH.

In some embodiments, wherein the compound of Formula (I) is a compound of Formula (I-A):

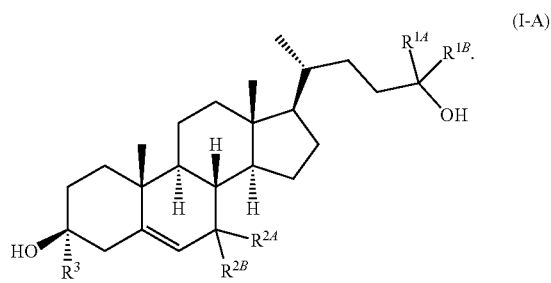

(I-A)

In some embodiments, the compound of Formula (I) is a compound of Formula (I-B):

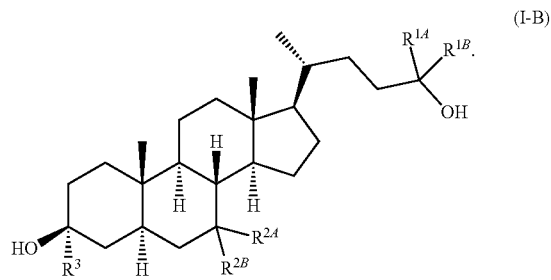

(I-B)

In some embodiments, the compound of Formula (I) is a compound of Formula (I-C):

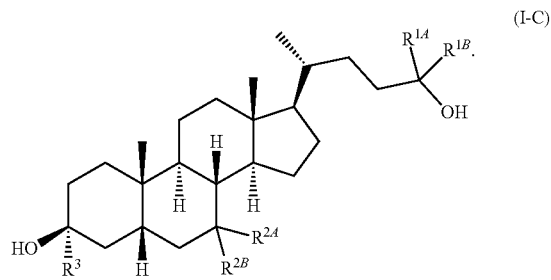

(I-C)

In some embodiments, the compound of Formula (I) is a compound of Formula (I-E), (I-F), or (I-G):

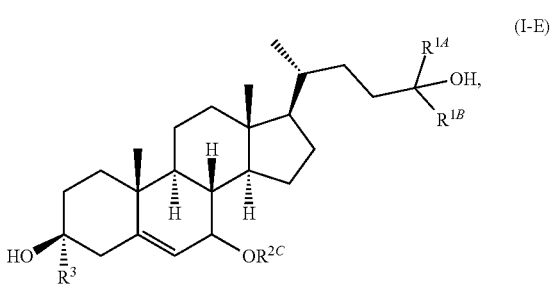

(I-E)

-continued

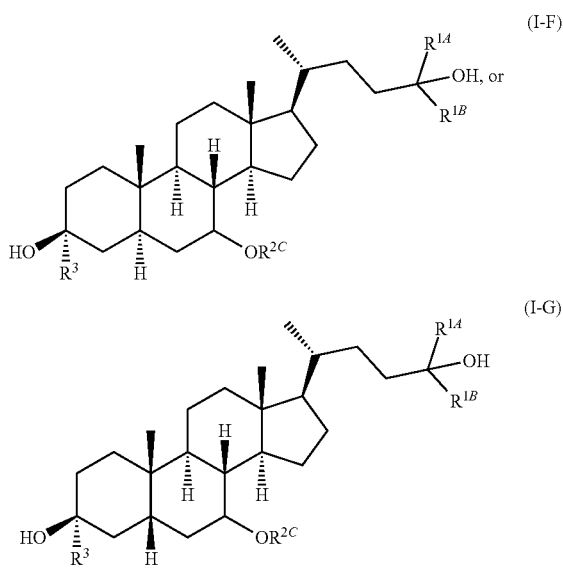

(I-F)

(I-G)

wherein $R^{2C}$ is hydrogen or alkyl and $R^3$ is alkyl, alkenyl, alkynyl, or —$OR^A$, wherein $R^A$ is alkyl.

In some embodiments, the compound of Formula (I) is a compound of Formula (I-H), (I-I), or (I-J):

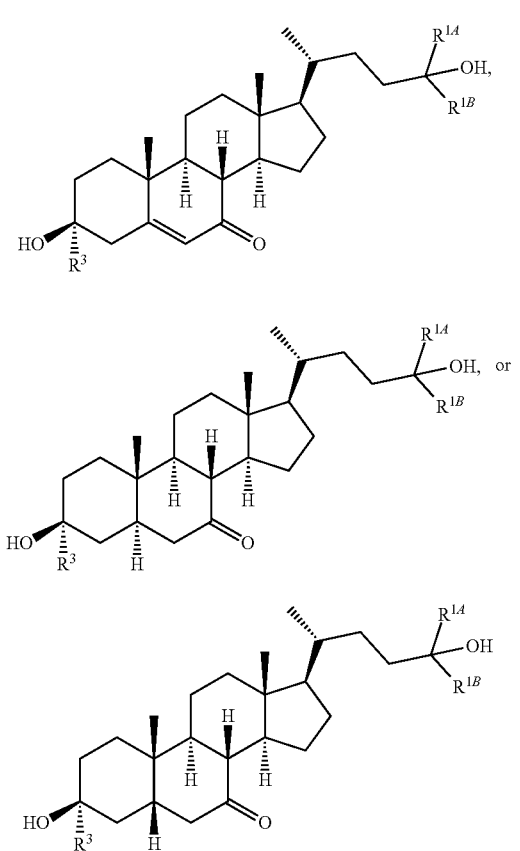

(I-H)

(I-I)

(I-J)

wherein $R^3$ is alkyl, alkenyl, alkynyl, or —$OR^A$, wherein $R^A$ is alkyl.

In some embodiments, the compound of Formula (I) is a compound of Formula (I-K):

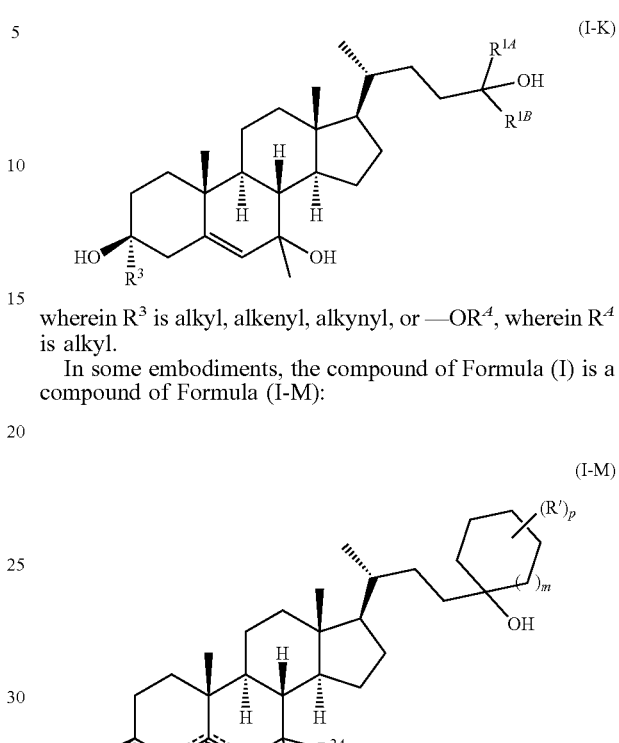

(I-K)

wherein $R^3$ is alkyl, alkenyl, alkynyl, or —$OR^A$, wherein $R^A$ is alkyl.

In some embodiments, the compound of Formula (I) is a compound of Formula (I-M):

(I-M)

where R' is alkyl or —$OR^A$, wherein $R^A$ is hydrogen or alkyl; p is 0, 1, 2, 3, 4, 5, or 6; and m is 0, 1, 2, or 3.

In some embodiments, each of $R^{1A}$ and $R^{1B}$ is independently unsubstituted or substituted alkyl (e.g., haloalkyl, alkoxyalkyl, —$CH_3$, —$CH_2CH_3$, —$CH(CH_3)_2$, —$CF_3$, or —$CH_2OCH_3$).

In some embodiments, each of $R^{1A}$ and $R^{1B}$ is independently substituted alkyl (e.g., haloalkyl).

In some embodiments, $R^{1A}$ is —$CF_3$ or —$CH_2OCH_3$.

In some embodiments, $R^{1A}$ and $R^{1B}$ is alkyl (e.g, unsubstituted or substituted alkyl (e.g, —$CH_3$)).

In some embodiments, $R^{1A}$ and $R^{1B}$ are —$CH_3$.

In some embodiments, $R^{1A}$ and $R^{1B}$, together with the carbon atom to which they are attached form a 3-8 membered ring.

In some embodiments, $R^{1A}$ is hydrogen and $R^{1B}$ is alkyl, carbocyclyl, heterocyclyl, aryl, or heteroaryl.

In some embodiments, $R^{1A}$ is substituted alkyl or unsubstituted $C_2$-$C_6$ alkyl and $R^{1B}$ is substituted or unsubstituted $C_1$-$C_6$ alkyl.

In some embodiments, each of $R^{2A}$ and $R^{2B}$ is independently alkyl (e.g., substituted or unsubstituted alkyl).

In some embodiments, each of $R^{2A}$ and $R^{2B}$ is independently —F.

In some embodiments, $R^{2A}$ and $R^{2B}$ are —$CH_3$ and $R^3$ is alkyl, alkenyl, alkynyl, or —$OR^A$, wherein $R^A$ is alkyl.

In some embodiments, $R^{2A}$ and $R^{2B}$ are —F.

In some embodiments, $R^3$ is alkyl (e.g., substituted or unsubstituted alkyl), alkenyl, alkynyl, or —$OR^A$, wherein $R^A$ is alkyl.

In some embodiments, $R^3$ is alkyl (e.g., substituted or unsubstituted alkyl).

In some embodiments, each of $R^{2A}$ and $R^{2B}$ is independently hydrogen and R is alkyl (e.g., substituted or unsubstituted alkyl).

In one aspect, provided herein are compounds according to Formula (II):

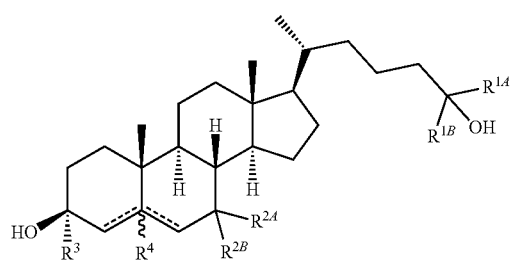

(II)

or a pharmaceutically acceptable salt thereof, wherein:

each of $R^{1A}$ and $R^{1B}$ is independently hydrogen, substituted or unsubstituted alkyl, carbocyclyl, heterocyclyl, aryl, or heteroaryl, or $R^{1A}$ and $R^{1B}$, together with the carbon atom to which they are attached form a 3-8 membered ring;

each of $R^{2A}$ and $R^{2B}$ is independently hydrogen, halo, —$OR^C$, alkyl, alkenyl, alkynyl, aryl, or heteroaryl, wherein $R^C$ is hydrogen or alkyl, or $R^{2A}$ and $R^{2B}$, together with the carbon atom to which they are attached form an oxo group, wherein $R^{2A}$ and $R^{2B}$ are not both simultaneously hydrogen;

$R^3$ is hydrogen, alkyl, alkenyl, alkynyl, or —$OR^A$, wherein $R^A$ is alkyl;

$R^4$ is absent or hydrogen; and

═══ represents a single or double bond, wherein when one of ═══ is a double bond, the other ═══ is a single bond; when both of ═══ are single bonds, then $R^4$ is hydrogen; and when one of the ═══ is a double bond, $R^4$ is absent;

provided that when $R^4$ is absent, $R^{2A}$ is —OH, $R^{2B}$ is hydrogen or —$CF_3$, and $R^{1A}$ and $R^{1B}$ are —$CH_3$, then $R^3$ is not hydrogen; and when $R^{1A}$ and $R^{1B}$ are —$CH_3$ and $R^3$ is hydrogen, then $R^{2A}$ and $R^{2B}$, together with the carbon atom to which they are attached do not form an oxo group.

In some embodiments, $R^4$ is absent, one of $R^{2A}$ and $R^{2B}$ is —OH, and $R^3$ is not hydrogen.

In some embodiments, the compound of Formula (II) is a compound of Formula (II-A):

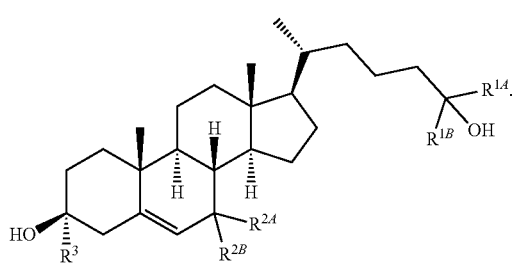

(II-A)

In some embodiments, the compound of Formula (II) is a compound of Formula (II-B):

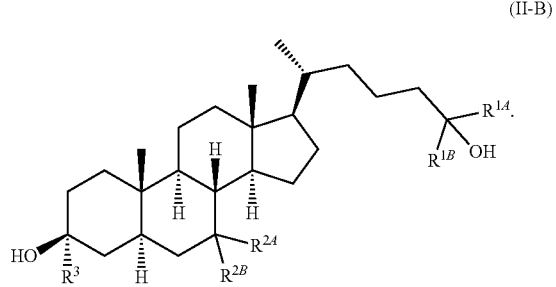

(II-B)

In some embodiments, the compound of Formula (II) is a compound of Formula (II-C):

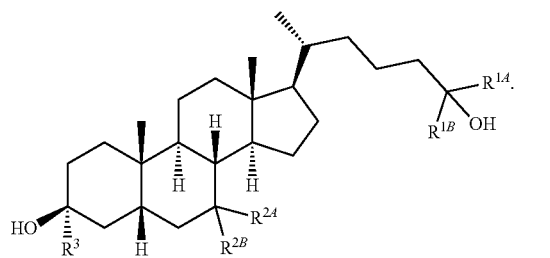

(II-C)

In some embodiments, the compound of Formula (II) is a compound of Formula (II-D):

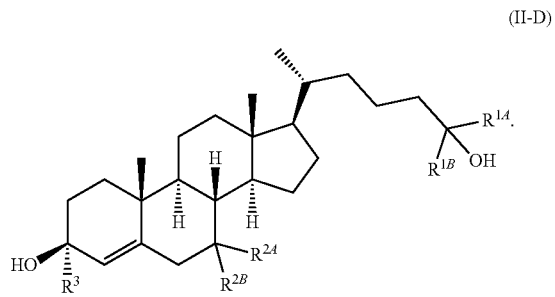

(II-D)

In some embodiments, the compound of Formula (II) is a compound of Formula (II-E), (II-F), or (II-G):

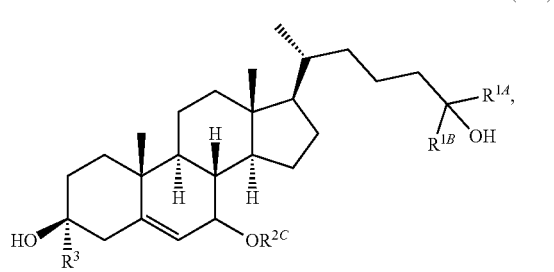

(II-E)

15

-continued (II-F)

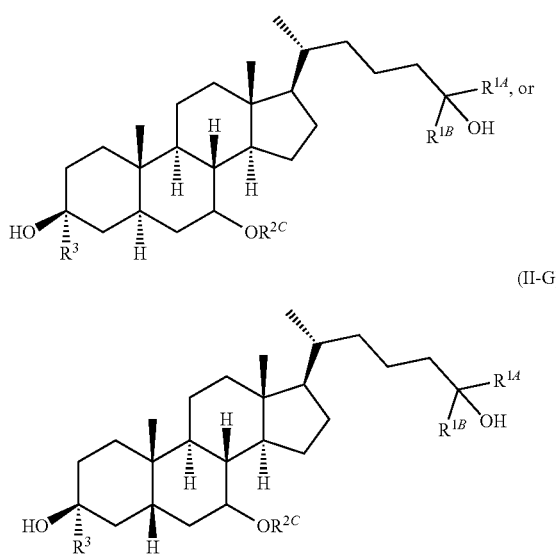

(II-G)

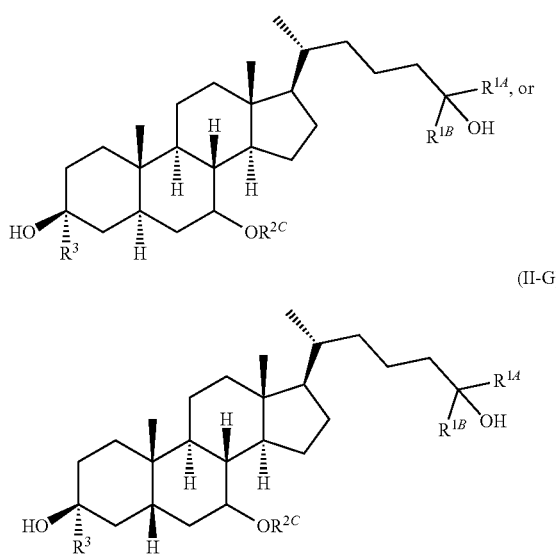

wherein $R^{2C}$ is hydrogen or alkyl (e.g., substituted or unsubstituted alkyl) and $R^3$ is alkyl (e.g., substituted or unsubstituted alkyl).

In some embodiments, the compound of Formula (II) is a compound of Formula (II-H), (II-I), or (II-J):

(II-H)

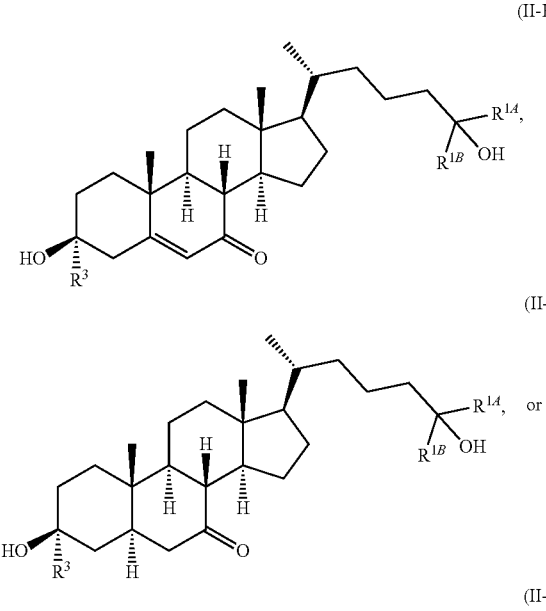

(II-I)

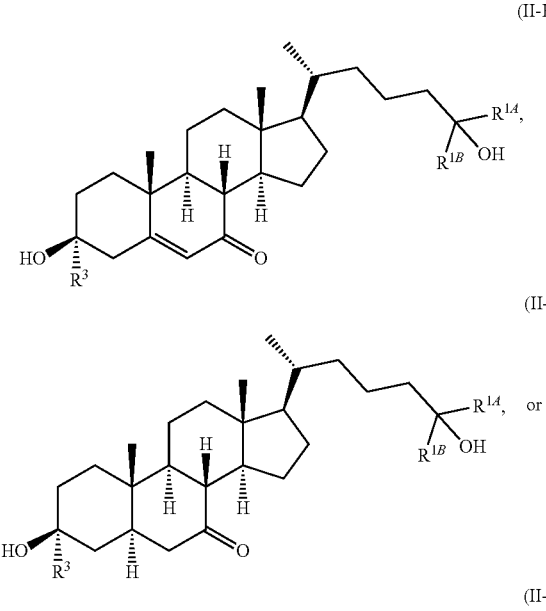

(II-J)

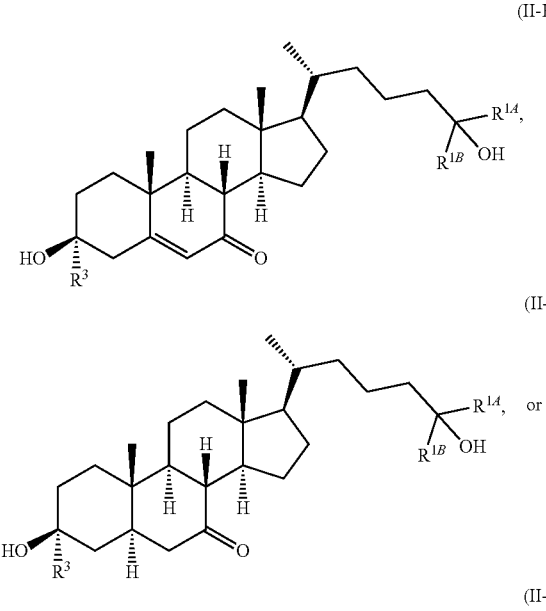

wherein $R^3$ is alkyl, alkenyl, alkynyl, or —$OR^A$, wherein $R^A$ is alkyl.

16

In some embodiments, the compound of Formula (II) is a compound of Formula (II-K):

(II-K)

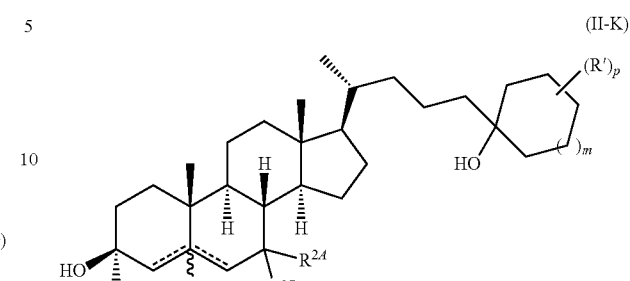

where R' is alkyl or —$OR^A$, wherein $R^A$ is hydrogen or alkyl; p is 0, 1, 2, 3, 4, 5, or 6; and m is 0, 1, 2, or 3.

In some embodiments, each of $R^{1A}$ and $R^{1B}$ is independently unsubstituted or substituted alkyl (e.g., haloalkyl, alkoxyalkyl, —$CH_3$, —$CH_2CH_3$, —$CH(CH_3)_2$, —$CF_3$ or —$CH_2OCH_3$).

In some embodiments, each of $R^{1A}$ and $R^{1B}$ is independently substituted alkyl (e.g., haloalkyl).

In some embodiments, $R^{1A}$ is —$CF_3$ or —$CH_2OCH_3$.

In some embodiments, $R^{1A}$ and $R^{1B}$ is alkyl (e.g., unsubstituted or substituted alkyl (e.g., —$CH_3$)).

In some embodiments, $R^{1A}$ and $R^{1B}$ are —$CH_3$.

In some embodiments, $R^{1A}$ and $R^{1B}$, together with the carbon atom to which they are attached form a ring.

In some embodiments, $R^{1A}$ is hydrogen and $R^{1B}$ is alkyl, carbocyclyl, heterocyclyl, aryl, or heteroaryl.

In some embodiments, each of $R^{2A}$ and $R^{2B}$ is independently alkyl (e.g., substituted or unsubstituted alkyl).

In some embodiments, $R^3$ is alkyl (e.g., substituted or unsubstituted alkyl).

In some embodiments, each of $R^{2A}$ and $R^{2B}$ is independently hydrogen and $R^3$ is alkyl (e.g., substituted or unsubstituted alkyl).

In some embodiments, each of $R^{2A}$ and $R^{2B}$ is independently —F.

In some embodiments, $R^{2A}$ and $R^{2B}$ are —$CH_3$ and $R^3$ is alkyl, alkenyl, alkynyl, or —$OR^A$, wherein $R^A$ is alkyl.

In some embodiments, $R^{2A}$ and $R^{2B}$ are —F.

In some embodiments, $R^{1A}$ is substituted alkyl or unsubstituted $C_2$-$C_6$ alkyl and $R^{1B}$ is substituted or unsubstituted $C_1$-$C_6$ alkyl.

In some aspects, the compound is a compound of Formula (III):

(III)

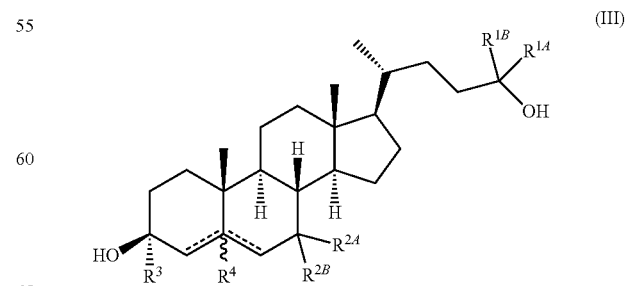

or a pharmaceutically acceptable salt thereof, wherein:

each of $R^{1A}$ and $R^{1B}$ is substituted or unsubstituted alkyl;

each of $R^{2A}$ and $R^{2B}$ is independently hydrogen, —$OR^C$, or alkyl, wherein $R^C$ is hydrogen or alkyl, or $R^{2A}$ and $R^{2B}$, together with the carbon atom to which they are attached form an oxo group, wherein $R^{2A}$ and $R^{2B}$ are not both simultaneously hydrogen;

$R^3$ is alkyl;

$R^4$ is absent or hydrogen; and $=\!=\!=$ represents a single or double bond, wherein when one of $=\!=\!=$ is a double bond, the other $=\!=\!=$ is a single bond; when both of $=\!=\!=$ are single bonds, then $R^4$ is hydrogen; and when one of the $=\!=\!=$ is a double bond, $R^4$ is absent.

In some embodiments, $R^{1A}$ and $R^{1B}$ are each —$CH_3$.

In some embodiments, $R^{2A}$ and $R^{2B}$ together with the carbon atom to which they are attached form an oxo group.

In some embodiments, $R^3$ is —$CH_2CH_3$.

In some embodiments, $R^{2A}$ is —OH and $R^{2B}$ is H.

In some embodiments, $R^{2A}$ is —$CH_3$ and $R^{2B}$ is H.

In some embodiments, $R^{2A}$ is —OH and $R^{2B}$ is —$CH_3$.

In some embodiments, $R^{1A}$ is —$CF_3$.

In an aspect, provided herein is a pharmaceutical composition comprising a compound described herein, or pharmaceutically acceptable salt thereof, and a pharmaceutically acceptable carrier.

In an aspect, provided herein is a method of inducing sedation or anesthesia comprising administering to a subject an effective amount of a compound described herein, or pharmaceutically acceptable salt thereof, or pharmaceutical composition thereof.

In an aspect, provided herein is a method for treating or preventing a disorder described herein, comprising administering to a subject in need thereof an effective amount of a compound described herein, or pharmaceutically acceptable salt thereof, or pharmaceutical composition thereof.

In some embodiments, the disorder is an autoimmune disorder.

In some embodiments, the disorder is rheumatoid arthritis, juvenile idiopathic arthritis, ankylosing spondylitis, psoriatic arthritis, Crohn's disease, ulcerative colitis, and plaque psoriasis.

In some embodiments, the disorder is a metabolic disorder.

In some embodiments, the disorder is a gastrointestinal (GI) disorder e.g., constipation, irritable bowel syndrome (IBS), inflammatory bowel disease (IBD) (e.g., ulcerative colitis, Crohn's disease), structural disorders affecting the GI, anal disorders (e.g., hemorrhoids, internal hemorrhoids, external hemorrhoids, anal fissures, perianal abscesses, anal fistula), colon polyps, cancer, or colitis.

In some embodiments, the disorder is inflammatory bowel disease.

In some embodiments, the disorder is cancer, diabetes, or a sterol synthesis disorder.

In an aspect, provided herein is a method for treating or preventing a CNS-related condition comprising administering to a subject in need thereof an effective amount of a compound described herein, or pharmaceutically acceptable salt thereof, or pharmaceutical composition thereof. In some embodiments, the CNS-related condition is an adjustment disorder, anxiety disorder (including obsessive-compulsive disorder, posttraumatic stress disorder, and social phobia), cognitive disorder (including Alzheimer's disease and other forms of dementia (e.g., frontotemporal dementia), dissociative disorder, eating disorder, mood disorder (including depression (e.g., postpartum depression), bipolar disorder, dysthymic disorder, suicidality), schizophrenia or other psychotic disorder (including schizoaffective disorder), sleep disorder (including insomnia), substance-related disorder, personality disorder (including obsessive-compulsive personality disorder), autism spectrum disorders (including those involving mutations to the Shank group of proteins (e.g., Shank3)), neurodevelopmental disorder (including Rett syndrome, Tuberous Sclerosis complex), multiple sclerosis, sterol synthesis disorders, pain (including acute and chronic pain; headaches, e.g., migraine headaches), encephalopathy secondary to a medical condition (including hepatic encephalopathy and anti-NMDA receptor encephalitis), seizure disorder (including status epilepticus and monogenic forms of epilepsy such as Dravet's disease), stroke, traumatic brain injury, movement disorder (including Huntington's disease and Parkinson's disease), vision impairment, hearing loss, or tinnitus.

In some embodiments, the disorder is Huntington's disease. In some embodiments, the disorder is Parkinson's disease. In some embodiments, the disorder is an inflammatory disease (e.g, lupus).

In some embodiments, the disorder is a sterol synthesis disorder.

In some embodiments, the disorder is Smith-Lemli-Opitz Syndrome (SLOS). In some embodiments, the disorder is desmosterolosis. In some embodiments, the disorder is sitosterolemia. In some embodiments, the disorder is cerebrotendinous xanthomatosis (CTX). In some embodiments, the disorder is Mevalonate Kinase Deficiency (MKD). In some embodiments, the disorder is SC4MOL gene mutation (SMO Deficiency). In some embodiments, the disorder is Niemann-Pick disease. In some embodiments, the disorder is autism spectrum disorder (ASD). In some embodiments, the disorder is associated with phenylketomuria.

Other objects and advantages will become apparent to those skilled in the art from a consideration of the ensuing Detailed Description, Examples, and Claims.

Definitions

Chemical Definitions

Definitions of specific functional groups and chemical terms are described in more detail below. The chemical elements are identified in accordance with the Periodic Table of the Elements, CAS version, *Handbook of Chemistry and Physics*, 75th Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5th Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3rd Edition, Cambridge University Press, Cambridge, 1987.

Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al, *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

The "enantiomeric excess" ("e.e.") or "% enantiomeric excess" ("% e.e") of a composition refers to an excess of one enantiomer relative to the other enantiomer present in the composition. For example, a composition can contain 90% of one enantiomer, e.g, the S enantiomer, and 10% of the other enantiomer, i.e., the R enantiomer.

e.e.=(90−10)/100=80%.

Thus, a composition containing 90% of one enantiomer and 10% of the other enantiomer is said to have an enantiomeric excess of 80%.

The "diastereomeric excess" ("d.e.") or "% diastereomeric excess" ("% d.e.") of a composition refers to an excess of one diastereomer relative to one or more different diastereomers present in the composition. For example, a composition can contain 90% of one diastereomer, and 10% of one or more different diastereomers.

d.e.=(90−10)/100=80%.

Thus, a composition containing 90% of one diastereomers and 10% of one or more different diastereomers is said to have a diastereomeric excess of 80%.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-6}$, and $C_{5-6}$ alkyl.

The following terms are intended to have the meanings presented therewith below and are useful in understanding the description and intended scope of the present invention. When describing the invention, which may include compounds, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein. The articles "a" and "an" may be used herein to refer to one or to more than one (i.e. at least one) of the grammatical objects of the article. By way of example "an analogue" means one analogue or more than one analogue.

"Aliphatic" refers to an alkyl, alkenyl, alkynyl, or carbocyclyl group, as defined herein.

"Alkyl" refers to a radical of a straight-chain or branched saturated hydrocarbon group having from 1 to 20 carbon atoms ("$C_{1-20}$ alkyl"). In some embodiments, an alkyl group has 1 to 12 carbon atoms ("$C_{1-12}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl", also referred to herein as "lower alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently optionally substituted, i.e., unsubstituted (an "unsubstituted alkyl") or substituted (a "substituted alkyl") with one or more substituents; e.g., for instance from 1 to 5 substituents, 1 to 3 substituents, or 1 substituent. In certain embodiments, the alkyl group is unsubstituted $C_{1-10}$ alkyl (e.g., —$CH_3$). In certain embodiments, the alkyl group is substituted $C_{1-10}$ alkyl. Common alkyl abbreviations include Me (—$CH_3$), Et (—$CH_2CH_3$), iPr (—$CH(CH_3)_2$), nPr (—$CH_2CH_2CH_3$), n-Bu (—$CH_2CH_2CH_2CH_3$), or i-Bu (—$CH_2CH(CH_3)_2$).

"Alkylene" refers to an alkyl group wherein two hydrogens are removed to provide a divalent radical, and which may be substituted or unsubstituted. Unsubstituted alkylene groups include, but are not limited to, methylene (—$CH_2$—), ethylene (—$CH_2CH_2$—), propylene (—$CH_2CH_2CH_2$—), butylene (—$CH_2CH_2CH_2CH_2$—), pentylene (—$CH_2CH_2CH_2CH_2CH_2$—), hexylene (—$CH_2CH_2CH_2CH_2CH_2CH_2$—), and the like. Exemplar substituted alkylene groups, e.g., substituted with one or more alkyl (methyl) groups, include but are not limited to, substituted methylene (—$CH(CH_3)$—, —$C(CH_3)_2$—), substituted ethylene (—$CH(CH_3)CH_2$—, —$CH_2CH(CH_3)$—, —$C(CH_3)_2CH_2$—, —$CH_2C(CH_3)_2$—), substituted propylene (—$CH(CH_3)CH_2CH_2$—, —$CH_2CH(CH_3)CH_2$—, —$CH_2CH_2CH(CH_3)$—, —$C(CH_3)_2CH_2CH_2$—, —$CH_2C(CH_3)_2CH_2$—, —$CH_2CH_2C(CH_3)_2$—), and the like. When a range or number of carbons is provided for a particular alkylene group, it is understood that the range or number refers to the range or number of carbons in the linear carbon divalent chain. Alkylene groups may be substituted or unsubstituted with one or more substituents as described herein.

"Alkenyl" refers to a radical of a straight-chain or branched hydrocarbon group having from 2 to 20 carbon atoms, one or more carbon-carbon double bonds (e.g., 1, 2, 3, or 4 carbon-carbon double bonds), and optionally one or more carbon-carbon triple bonds (e.g., 1, 2, 3, or 4 carbon-carbon triple bonds) ("$C_{2-20}$ alkenyl"). In certain embodiments, alkenyl does not contain any triple bonds. In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents e.g., for instance from 1 to 5 substituents, 1 to 3 substituents, or 1 substituent. In certain embodiments, the alkenyl group is unsubstituted $C_{2-10}$ alkenyl. In certain embodiments, the alkenyl group is substituted $C_{2-10}$ alkenyl.

"Alkynyl" refers to a radical of a straight-chain or branched hydrocarbon group having from 2 to 20 carbon atoms, one or more carbon-carbon triple bonds (e.g., 1, 2, 3, or 4 carbon-carbon triple bonds), and optionally one or more carbon-carbon double bonds (e.g, 1, 2, 3, or 4 carbon-carbon double bonds) ("$C_{2-20}$ alkynyl"). In certain embodiments, alkynyl does not contain any double bonds. In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_2$-g alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents; e.g, for instance from 1 to 5 substituents, 1 to 3 substituents, or 1 substituent. In certain embodiments, the alkynyl group is unsubstituted $C_{2-10}$ alkynyl. In certain embodiments, the alkynyl group is substituted, $C_{2-10}$ alkynyl.

The term "heteroalkyl," as used herein, refers to an alkyl group, as defined herein, which further comprises 1 or more (e.g., 1, 2, 3, or 4) heteroatoms (e.g., oxygen, sulfur, nitrogen, boron, silicon, phosphorus) within the parent chain, wherein the one or more heteroatoms is inserted between adjacent carbon atoms within the parent carbon chain and/or one or more heteroatoms is inserted between a carbon atom and the parent molecule, i.e., between the point of attachment. In certain embodiments, a heteroalkyl group refers to a saturated group having from 1 to 10 carbon atoms and 1, 2, 3, or 4 heteroatoms ("heteroC$_{1-10}$ alkyl"). In some embodiments, a heteroalkyl group is a saturated group having 1 to 9 carbon atoms and 1, 2, 3, or 4 heteroatoms ("heteroC$_{1-9}$ alkyl"). In some embodiments, a heteroalkyl group is a saturated group having 1 to 8 carbon atoms and 1, 2, 3, or 4 heteroatoms ("heteroC$_{1-8}$ alkyl"). In some embodiments, a heteroalkyl group is a saturated group having 1 to 7 carbon atoms and 1, 2, 3, or 4 heteroatoms ("heteroC$_{1-7}$ alkyl"). In some embodiments, a heteroalkyl group is a group having 1 to 6 carbon atoms and 1, 2, or 3 heteroatoms ("heteroC$_{1-6}$ alkyl"). In some embodiments, a heteroalkyl group is a saturated group having 1 to 5 carbon atoms and 1 or 2 heteroatoms ("heteroC$_{1-5}$ alkyl"). In some embodiments, a heteroalkyl group is a saturated group having 1 to 4 carbon atoms and 1 or 2 heteroatoms ("heteroC$_{1-4}$ alkyl"). In some embodiments, a heteroalkyl group is a saturated group having 1 to 3 carbon atoms and 1 heteroatom ("heteroC$_{1-3}$ alkyl"). In some embodiments, a heteroalkyl group is a saturated group having 1 to 2 carbon atoms and 1 heteroatom ("heteroC$_{1-2}$ alkyl"). In some embodiments, a heteroalkyl group is a saturated group having 1 carbon atom and 1 heteroatom ("heteroC$_1$ alkyl"). In some embodiments, a heteroalkyl group is a saturated group having 2 to 6 carbon atoms and 1 or 2 heteroatoms ("heteroC$_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is ah unsubstituted heteroC$_{1-10}$ alkyl. In certain embodiments, the heteroalkyl group is a substituted heteroC$_{1-10}$ alkyl.

"Aryl" refers to a radical of a monocyclic or polycyclic (e.g., bicyclic or tricyclic) 4n+2 aromatic ring system (e.g., having 6, 10, or 14% electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, and trinaphthalene. Particularly aryl groups include phenyl, naphthyl, indenyl, and tetrahydronaphthyl. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

In certain embodiments, an aryl group substituted with one or more of groups selected from halo, $C_1$-$C_8$ alkyl, G-$C_8$ haloalkyl, cyano, hydroxy, $C_1$-$C_8$ alkoxy, and amino.

Examples of representative substituted aryls include the following

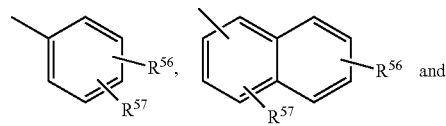

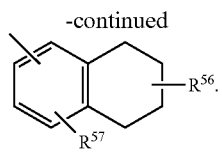

wherein one of $R^{56}$ and $R^{57}$ may be hydrogen and at least one of $R^{56}$ and $R^{57}$ is each independently selected from $C_1$-$C_8$ alkyl, $C_1$-$C_8$ haloalkyl, 4-10 membered heterocyclyl, alkanoyl, $C_1$-$C_8$ alkoxy, heteroaryloxy, alkylamino, arylamino, heteroarylamino, $NR^{58}COR^{59}$, $NR^{58}SOR^{59}$ $NR^{58}SO_2R^{59}$, COOalkyl, COOaryl, $CONR^{58}R^{59}$, $CONR^{58}OR^{59}$, $NR^{58}R^{59}$, $SO_2NR^{58}R^{59}$, S-alkyl, SOalkyl, $SO_2$alkyl, Saryl, SOaryl, $SO_2$aryl; or $R^{56}$ and $R^{57}$ may be joined to form a cyclic ring (saturated or unsaturated) from 5 to 8 atoms, optionally containing one or more heteroatoms selected from the group N, O, or S. $R^{60}$ and $R^{61}$ are independently hydrogen, $C_1$-$C_8$ alkyl, $C_1$-$C_4$ haloalkyl, $C_3$-$C_{10}$ cycloalkyl, 4-10 membered heterocyclyl, $C_6$-$C_{10}$ aryl, substituted $C_6$-$C_{10}$ aryl, 5-10 membered heteroaryl, or substituted 5-10 membered heteroaryl.

"Fused aryl" refers to an aryl having two of its ring carbon in common with a second aryl or heteroaryl ring or with a carbocyclyl or heterocyclyl ring.

"Heteroaryl" refers to a radical of a 5-10 membered monocyclic or bicyclic 4n+2 aromatic ring system (e.g., having 6 or 10 n electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g, 5-indolyl).

In some embodiments, a heteroaryl group is a 5-10 membered aromatic ring system having ring carbon atoms; and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

Examples of representative heteroaryls include the following:

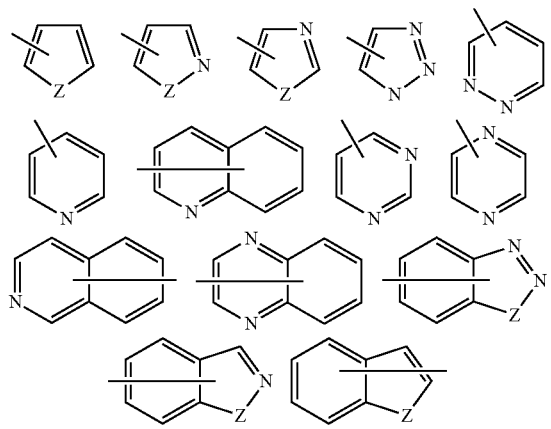

wherein each Z is selected from carbonyl, N, $NR^{65}$, O, and S; and $R^{65}$ is independently hydrogen, $C_1$-$C_8$ alkyl, $C_3$-$C_{10}$ cycloalkyl, 4-10 membered heterocyclyl, $C_6$-$C_{10}$ aryl, and 5-10 membered heteroaryl.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Nitrogen-containing heterocyclyl" group means a 4- to 7-membered non-aromatic cyclic group containing at least one nitrogen atom, for example, but without limitation, morpholine, piperidine (e.g. 2-piperidinyl, 3-piperidinyl and 4-piperidinyl), pyrrolidine (e.g. 2-pyrrolidinyl and 3-pyrrolidinyl), azetidine, pyrrolidone, imidazoline, imidazolidinone, 2-pyrazoline, pyrazolidine, piperazine, and N-alkyl piperazines such as N-methyl piperazine. Particular examples include azetidine, piperidone and piperazone.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g., heteroalkyl, cycloalkyl, e.g., heterocyclyl, aryl, e.g. heteroaryl, cycloalkenyl, e.g. cycloheteroalkenyl, and the like having from 1 to 5, and particularly from 1 to 3 heteroatoms.

"Acyl" refers to a radical —C(O)$R^{20}$, where $R^{20}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, as defined herein. "Alkanoyl" is an acyl group wherein $R^{20}$ is a group other than hydrogen. Representative acyl groups include, but are not limited to, formyl (—CHO), acetyl (—C(=O)CH$_3$), cyclohexylcarbonyl, cyclohexylmethylcarbonyl, benzoyl (—C(=O)Ph), benzylcarbonyl (—C(=O)CH$_2$Ph), —C(O)—C$_1$-C$_8$ alkyl, —C(O)—(CH$_2$)$_t$(C$_6$-C$_{10}$ aryl), —C(O)—(CH$_2$)$_t$(5-10 membered heteroaryl), —C(O)—(CH$_2$)$_t$(C$_3$-C$_{10}$ cycloalkyl), and —C(O)—(CH$_2$)$_t$(4-10 membered heterocyclyl), wherein t is an integer from 0 to 4. In certain embodiments, $R^{21}$ is C$_1$-C$_8$ alkyl, substituted with halo or hydroxy; or C$_3$-C$_{10}$ cycloalkyl, 4-10 membered heterocyclyl, C$_6$-C$_{10}$ aryl, arylalkyl, 5-10 membered heteroaryl or heteroarylalkyl, each of which is substituted with unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

"Alkoxy" refers to the group —OR$^{29}$ where $R^{29}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl. Particular alkoxy groups are methoxy, ethoxy, n-propoxy, isopropoxy, n-butoxy, tert-butoxy, sec-butoxy, n-pentoxy, n-hexoxy, and 1,2-dimethylbutoxy. Particular alkoxy groups are lower alkoxy, i.e. with between 1 and 6 carbon atoms. Further particular alkoxy groups have between 1 and 4 carbon atoms.

In certain embodiments, $R^{29}$ is a group that has 1 or more substituents, for instance from 1 to 5 substituents, and particularly from 1 to 3 substituents, in particular 1 substituent, selected from the group consisting of amino, substituted amino, C$_6$-C$_{10}$ aryl, aryloxy, carboxyl, cyano, C$_3$-C$_{10}$ cycloalkyl, 4-10 membered heterocyclyl, halogen, 5-10 membered heteroaryl, hydroxyl, nitro, thioalkoxy, thioaryloxy, thiol, alkyl-S(O)—, aryl-S(O)—, alkyl-S(O)$_2$— and aryl-S(O)$_2$—. Exemplary 'substituted alkoxy' groups include, but are not limited to, —O—(CH$_2$)$_t$(C$_6$-C$_{10}$ aryl), —O—(CH$_2$)$_t$(5-10 membered heteroaryl), —O—(CH$_2$)$_t$(C$_3$-C$_{10}$ cycloalkyl), and —O—(CH$_2$)$_t$(4-10 membered heterocyclyl), wherein t is an integer from 0 to 4 and any aryl, heteroaryl, cycloalkyl or heterocyclyl groups present, may themselves be substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy. Particular exemplary 'substituted alkoxy' groups are —OCF$_3$, —OCH$_2$CF$_3$, —OCH$_2$Ph, —OCH$_2$-cyclopropyl, —OCH$_2$CH$_2$OH, and —OCH$_2$CH$_2$NMe$_2$.

"Amino" refers to the radical —NH$_2$.

"Oxo group" refers to —C(=O)—.

"Substituted amino" refers to an amino group of the formula —N(R$^{38}$)$_2$ wherein $R^{38}$ is hydrogen, substituted or unsubstituted alkyl, substituted or unsubstitued alkenyl, substituted or unsubstitued alkynyl, substituted or unsubstitued carbocyclyl, substituted or unsubstituted heterocyclyl, substituted or unsubstitued aryl, substituted or unsubstitued heteroaryl, or an amino protecting group, wherein at least one of $R^{38}$ is not a hydrogen. In certain embodiments, each $R^{38}$ is independently selected from hydrogen, C$_1$-C$_8$ alkyl, C$_3$-C$_8$ alkenyl, C$_3$-C$_8$ alkynyl, C$_6$-C$_{10}$ aryl, 5-10 membered heteroaryl, 4-10 membered heterocyclyl, or C$_3$-C$_{10}$ cycloalkyl; or C$_1$-C$_8$ alkyl, substituted with halo or hydroxy; C$_3$-C$_8$ alkenyl, substituted with halo or hydroxy; C$_3$-C$_8$ alkynyl, substituted with halo or hydroxy, or —(CH$_2$)$_t$(C$_6$-C$_{10}$ aryl), —(CH$_2$)$_t$(5-10 membered heteroaryl), —(CH$_2$)$_t$(C$_3$-C$_{10}$ cycloalkyl), or —(CH$_2$)$_t$(4-10 membered heterocyclyl), wherein t is an integer between 0 and 8, each of which is substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy; or both $R^{38}$ groups are joined to form an alkylene group.

Exemplary "substituted amino" groups include, but are not limited to, —NR$^{39}$—C$_1$-C$_8$ alkyl, —NR$^{39}$—(CH$_2$)$_t$(C$_6$-C$_{10}$ aryl), —NR$^{39}$—(CH$_2$)$_t$(5-10 membered heteroaryl), —NR$^{39}$—(CH$_2$)$_t$(C$_3$-C$_{10}$ cycloalkyl), and —NR$^{39}$—(CH$_2$)$_t$(4-10 membered heterocyclyl), wherein t is an integer from 0 to 4, for instance 1 or 2, each $R^{39}$ independently represents H or C$_1$-C$_8$ alkyl; and any alkyl groups present, may themselves be substituted by halo, substituted or unsubstituted amino, or hydroxy; and any aryl, heteroaryl, cycloalkyl, or heterocyclyl groups present, may themselves be substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy. For the avoidance of doubt the term 'substituted amino' includes the groups alkylamino, substituted alkylamino, alkylarylamino, substituted alkylarylamino, arylamino, substituted arylamino, dialkylamino, and substituted dialkylamino as defined below.

Substituted amino encompasses both monosubstituted amino and disubstituted amino groups.

"Carboxy" refers to the radical —C(O)OH.

"Cyano" refers to the radical —CN.

"Halo" or "halogen" refers to fluoro (F), chloro (Cl), bromo (Br), and iodo (I). In certain embodiments, the halo group is either fluoro or chloro.

"Haloalkyl" refers to an alkyl radical in which the alkyl group is substituted with one or more halogens. Typical haloalkyl groups include, but are not limited to, trifluoromethyl, difluoromethyl, fluoromethyl, chloromethyl, dichloromethyl, dibromoethyl, tribromoethyl, tetrafluoroethyl, and the like.

"Hydroxy" refers to the radical —OH.

"Nitro" refers to the radical —$NO_2$.

"Thioketo" refers to the group =S.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g. a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —$NO_2$, —$N_3$, —$SO_2H$, —$SO_3H$, —OH, —$OR^{aa}$, —$ON(R^{bb})_2$, —$N(R^{bb})_2$, —$N(R^{bb})_3^+X^-$, —$N(OR^{cc})R^{bb}$, —SH, —$SR^{aa}$, —$SSR^{cc}$, —C(=O)$R^{aa}$, —$CO_2H$, —CHO, —C($OR^{cc}$)$_2$, —$CO_2R^{aa}$, —OC(=O)$R^{aa}$, —$OCO_2R^{aa}$, —C(=O)N($R^{bb}$)$_2$, —OC(=O)N($R^{bb}$)$_2$, —$NR^{bb}$C(=O)$R^{aa}$, —$NR^{bb}CO_2R^{aa}$, —$NR^{bb}$C(=O)N($R^{bb}$)$_2$, —C(=$NR^{bb}$)$R^{aa}$, —C(=$NR^{bb}$)$OR^{aa}$, —OC(=$NR^{bb}$)$R^{aa}$, —OC(=$NR^{bb}$)$OR^{aa}$, —C(=$NR^{bb}$)N($R^{bb}$)$_2$, —OC(=$NR^{bb}$)N($R^{bb}$)$_2$, —$NR^{bb}$C(=$NR^{bb}$)N($R^{bb}$)$_2$, —C(=O)$NR^{bb}SO_2R^{aa}$, —$NR^{bb}SO_2R^{aa}$, —$SO_2$N($R^{bb}$)$_2$, —$SO_2R^{aa}$, —$SO_2OR^{aa}$, —$OSO_2R^{aa}$, —S(=O)$R^{aa}$, —OS(=O)$R^{aa}$, —Si($R^{aa}$)$_3$, —OSi($R^{aa}$)$_3$—C(=S)N($R^{bb}$)$_2$, —C(=O)$SR^{aa}$, —C(=S)$SR^{aa}$, —SC(=S)$SR^{aa}$, —SC(=O)$SR^{aa}$, —OC(=O)$SR^{aa}$, —SC(=O)$OR^{aa}$, —SC(=O)$R^{aa}$, —P(=O)$_2R^{aa}$, —OP(=O)$_2R^{aa}$, —P(=O)($R^{aa}$)$_2$, —OP(=O)($R^{aa}$)$_2$, —OP(=O)($OR^{cc}$)$_2$, —P(=O)$_2$N($R^{bb}$)$_2$, —OP(=O)$_2$N($R^{bb}$)$_2$, —P(=O)(N$R^{bb}$)$_2$, —OP(=O)(N$R^{bb}$)$_2$, —$NR^{bb}$P(=O)($OR^{cc}$)$_2$, —$NR^{bb}$P(=O)(N$R^{bb}$)$_2$, —P($R^{cc}$)$_2$, —P($R^{cc}$)$_3$, —OP($R^{cc}$)$_2$, —OP($R^{cc}$)$_3$, —B($R^{aa}$)$_2$, —B($OR^{cc}$)$_2$, —$BR^{aa}(OR^{cc})$, $C_{1-10}$ alkyl, $C_{1-10}$ haloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 $R^{dd}$ groups; or two geminal hydrogens on a carbon atom are replaced with the group =O, =S, =NN($R^{bb}$)$_2$, =$NNR^{bb}$C(=O)$R^{aa}$, =$NNR^{bb}$C(=O)$OR^{aa}$, =$NNR^{bb}S(=O)_2R^{aa}$, =$NR^{bb}$, or =$NOR^{cc}$;

each instance of $R^{aa}$ is, independently, selected from $C_{1-10}$ alkyl, $C_{1-10}$ haloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, —$OR^{aa}$, —N($R^{cc}$)$_2$, —CN, —C(=O)$R^{aa}$, —C(=O)N($R^{cc}$)$_2$, —$CO_2R^{aa}$, —$SO_2R^{aa}$, —C(=$NR^{cc}$)$OR^{aa}$, —C(=$NR^{cc}$)N($R^{cc}$)$_2$, —$SO_2N(R^{cc})_2$, —$SO_2R^{cc}$, —$SO_2OR^{cc}$, —$SOR^{aa}$, —C(=S)N($R^{cc}$)$_2$, —C(=O)$SR^{cc}$, —C(=S)$SR^{cc}$, —P(=O)$_2R^{aa}$, —P(=O)($R^{aa}$)$_2$, —P(=O)$_2$N($R^{cc}$)$_2$, —P(=O)(N$R^{cc}$)$_2$, $C_{1-10}$ alkyl, $C_{1-10}$ haloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{cc}$ is, independently, selected from hydrogen, $C_{1-10}$ alkyl, $C_{1-10}$ haloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —$NO_2$, —$N_3$, —$SO_2H$, —$SO_3H$, —OH, —$OR^{ee}$, —ON($R^{ff}$)$_2$, —N($R^{ff}$)$_2$, —N($R^{ff}$)$_3^+X^-$, —N($OR^{ee}$)$R^{ff}$, —SH, —$SR^{ee}$, —$SSR^{ee}$, —C(=O)$R^{ee}$, —$CO_2H$, —$CO_2R^{ee}$, —OC(=O)$R^{ee}$, —$OCO_2R^{ee}$, —C(=O)N($R^{ff}$)$_2$, —OC(=O)N($R^{ff}$)$_2$, —$NR^{ff}$C(=O)$R^{ee}$, —$NR^{ff}CO_2R^{ee}$, —$NR^{ff}$C(=O)N($R^{ff}$)$_2$, —C(=$NR^{ff}$)$OR^{ee}$, —OC(=$NR^{ff}$)$R^{ee}$, —OC(=$NR^{ff}$)$OR^{ee}$, —C(=$NR^{ff}$)N($R^{ff}$)$_2$, —OC(=$NR^{ff}$)N($R^{ff}$)$_2$, —$NR^{ff}$C(=$NR^{ff}$)N($R^{ff}$)$_2$, —$NR^{ff}SO_2R^{ee}$, —$SO_2N(R^{ff})_2$, —$SO_2R^{ee}$, —$SO_2OR^{ee}$, —$OSO_2R^{ee}$, —S(=O)$R^{ee}$, —Si($R^{ee}$)$_3$, —OSi($R^{ee}$)$_3$, —C(=S)N($R^{ff}$)$_2$, —C(=O)$SR^{ee}$, —C(=S)$SR^{ee}$, —SC(=S)$SR^{ee}$, —P(=O)$_2R^{ee}$, —P(=O)($R^{ee}$)$_2$, —OP(=O)($R^{ee}$)$_2$, —OP(=O)($OR^{ee}$)$_2$, $C_{1-6}$ alkyl, $C_{1-6}$ haloalkyl, $C_{2-6}$ alkenyl, $C_{2-6}$ alkynyl, $C_{3-10}$ carbocyclyl, 3-10 membered heterocyclyl, $C_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S;

each instance of $R^{ee}$ is, independently, selected from $C_{1-6}$ alkyl, $C_{1-6}$ haloalkyl, $C_{2-6}$ alkenyl, $C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ haloalkyl, $C_{2-6}$ alkenyl, $C_{2-5}$ alkynyl, $C_{3-10}$ carbocyclyl, 3-10 membered heterocyclyl, $C_{6-10}$ aryl and 5-10 membered heteroaryl, or two $R^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —$NO_2$, —$N_3$, —$SO_2H$, —$SO_3H$, —OH, —$OC_{1-6}$ alkyl, —$ON(C_{1-6}$ alkyl$)_2$, —$N(C_{1-6}$ alkyl$)_2$, —$N(C_{1-6}$ alkyl$)_3^+X^-$, —$NH(C_{1-6},$ alkyl$)_2^+X^-$, —$NH_2(C_{1-6}$ alkyl$)^+X$, —$NH_3^+X^-$, —$N(OC_{1-6}$ alkyl$)_2(C_{1-6}$ alkyl), —$N(OH)(C_{1-6}$ alkyl), —NH(OH), —SH, —$SC_{1-6}$ alkyl, —$SS(C_{1-6}$ alkyl), —C(=O)($C_{1-6}$ alkyl), —$CO_2H$, —$CO_2(C_{1-6}$ alkyl), —OC(=O)($C_{1-6}$ alkyl), —$OCO_2(C_{1-6}$ alkyl), —C(=O)$NH_2$, —C(=O)N($C_{1-6}$ alkyl$)_2$, —OC(=O)NH($C_{1-6}$ alkyl), —NHC(=O)($C_{1-6}$ alkyl), —N($C_{1-6}$ alkyl)C(=O)($C_{1-6}$ alkyl), —$NHCO_2$($C_{1-6}$ alkyl), —NHC(=O)N($C_{1-6}$ alkyl$)_2$, —NHC(=O)NH($C_{1-6}$ alkyl), —NHC(=O)$NH_2$, —C(=NH)O($C_{1-6}$ alkyl), —OC(=NH)($C_{1-6}$ alkyl), —OC(=NH)O$C_{1-6}$ alkyl, —C(=NH)N($C_{1-6}$ alkyl$)_2$, —C(=NH)NH($C_{1-6}$ alkyl), —C(=NH)$NH_2$, —OC(=NH)N($C_{1-6}$ alkyl$)_2$, —OC(NH)NH($C_{1-6}$ alkyl), —OC(NH)$NH_2$, —NHC(NH)N($C_{1-6}$ alkyl$)_2$, —NHC(=NH)$NH_2$, —$NHSO_2$($C_{1-6}$ alkyl), —$SO_2N(C_{1-6}$ alkyl$)_2$, —$SO_2NH(C_{1-6}$ alkyl), —$SO_2NH_2$, —$SO_2C_{1-6}$ alkyl, —$SO_2OC_{1-6}$ alkyl, —$OSO_2C_{1-6}$ alkyl, —$SOC_{1-6}$ alkyl, —Si($C_{1-6}$ alkyl$)_3$, —OSi($C_{1-6}$ alkyl$)_3$-C(=S)N($C_{1-6}$ alkyl$)_2$, C(=S)NH($C_{1-6}$ alkyl), C(=S)$NH_2$, —C(=O)S($C_{1-6}$ alkyl), —C(=S)S$C_{1-6}$ alkyl, —SC(=S)S$C_{1-6}$ alkyl, —P(=O)$_2$($C_{1-6}$ alkyl), —P(=O)($C_{1-6}$ alkyl$)_2$, —OP(=O)($C_{1-6}$ alkyl$)_2$, —OP(=O)(O$C_{1-6}$ alkyl$)_2$, $C_{1-6}$ alkyl, $C_{1-6}$ haloalkyl, $C_{2-6}$ alkenyl, $C_{2-6}$ alkynyl, $C_{3-10}$ carbocyclyl, $C_{6-10}$ aryl, 3-10 membered heterocyclyl, 5-16 membered heteroaryl; or two geminal $R^{gg}$ substituents can be joined to form =O or =S; wherein $X^-$ is a counterion.

A "counterion" or "anionic counterion" is a negatively charged group associated with a cationic quaternary amino group in order to maintain electronic neutrality. Exemplary counterions include halide ions (e.g., $F^-$, $Cl^-$, $Br^-$, $I^-$), $NO_3^-$, $ClO_4^-$, $OH^-$, $H_2PO_4^-$, $HSO_4^-$, $SO_4^{-2}$sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

Nitrogen atoms can be substituted or unsubstituted as valency permits, and include primary, secondary, tertiary, and quarternary nitrogen atoms. Exemplary nitrogen atom substituents include, but are not limited to, hydrogen, —OH, —$OR^{aa}$, —$N(R^{cc})_2$, —CN, —C(=O)$R^{aa}$, —C(=O)N($R^{cc})_2$, —$CO_2R^{aa}$, —$SO_2R^{aa}$, —C(=$NR^{bb}$)$R^{aa}$, —C(=$NR^{cc}$)$OR^{aa}$, —C(=$NR^{cc}$)N($R^{cc})_2$, —$SO_2N(R^{cc})_2$, —$SO_2R^{cc}$, —$SO_2OR^{cc}$, —$SOR^{aa}$, —C(=S)N($R^{cc})_2$, —C(=O)$SR^{cc}$, —C(=S)$SR^{cc}$, —P(=O)$_2R^{aa}$, —P(=O)($R^{A3})_2$, —P(=O)$_2N(R^{cc})_2$, —P(=O)($NR^{cc})_2$, $C_{1-10}$ alkyl, CHO haloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

These and other exemplary substituents are described in more detail in the Detailed Description, Examples, and claims. The invention is not intended to be limited in any manner by the above exemplary listing of substituents.

Other Definitions

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and $N^+(C_{1-4}$ alkyl$)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

A "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal. The terms "human," "patient," and "subject" are used interchangeably herein.

Disease, disorder, and condition are used interchangeably herein.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition ("therapeutic treatment"), and also contemplates an action that occurs before a subject begins to suffer from the specified disease, disorder or condition ("prophylactic treatment").

In general, the "effective amount" of a compound refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the age, health, and condition of the subject. An effective amount encompasses therapeutic and prophylactic treatment.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

As used herein, and unless otherwise specified, a "prophylactically effective amount" of a compound is an amount sufficient to prevent a disease, disorder or condition, or one or more symptoms associated with the disease, disorder or condition, or prevent its recurrence. A prophylactically effective amount of a compound means an amount of a therapeutic agent, alone or in combination with other agents, which provides a prophylactic benefit in the prevention of the disease, disorder or condition. The term "prophylactically effective amount" can encompass an amount that improves overall prophylaxis or enhances the prophylactic efficacy of another prophylactic agent.

DETAILED DESCRIPTION OF CERTAIN EMBODIMENTS OF THE INVENTION

As generally described herein, the present invention provides substituted oxysterols useful for preventing and/or treating a broad range of disorders, including, but not limited to, NMDA-mediated disorders.

Compounds

In one aspect, provided herein are compounds according to Formula (A):

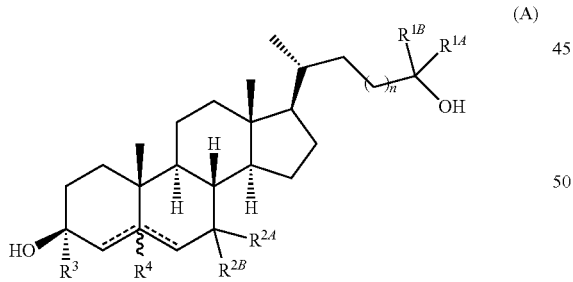

or a pharmaceutically acceptable salt thereof, wherein:

each of $R^{1A}$ and $R^{1B}$ is independently hydrogen, substituted or unsubstituted alkyl, carbocyclyl, heterocyclyl, aryl, or heteroaryl, or $R^{1A}$ and $R^{1B}$, together with the carbon atom to which they are attached form a 3-8 membered ring;

n is 1 or 2;

each of $R^{2A}$ and $R^{2B}$ is independently hydrogen, halo, $-OR^C$, alkyl, alkenyl, alkynyl, aryl, or heteroaryl, wherein $R^C$ is hydrogen or alkyl, or $R^{2A}$ and $R^{2B}$, together with the carbon atom to which they are attached form an oxo group, wherein $R^{2A}$ and $R^{2B}$ are not both simultaneously hydrogen;

$R^3$ is hydrogen, alkyl, alkenyl, alkynyl, or $-OR^A$, wherein $R^A$ is alkyl;

$R^4$ is absent or hydrogen; and

═══ represents a single or double bond, wherein when one of ═══ is a double bond, the other ═══ is a single bond; when both of ═══ are single bonds, then $R^4$ is hydrogen; and when one of the ═══ is a double bond, $R^4$ is absent.

In some embodiments, n is 1. In other embodiments, n is 2.

In some embodiments, when $R^{1A}$, $R^3$, and $R^4$ are hydrogen and $R^{1B}$ is unsubstituted isopropyl, then $R^{2A}$ and $R^{2B}$, together with the carbon atom to which they are attached do not form an oxo group; and when $R^4$ is absent, $R^3$ is hydrogen, and $R^{1A}$ and $R^{1B}$ are $-CH_3$, then $R^{2A}$ is not $-CH_3$ and $R^{2B}$ is not $-OH$.

In some embodiments, when $R^4$ is absent, $R^{2A}$ is $-OH$, $R^{2B}$ is hydrogen or $-CF_3$, and $R^{1A}$ and $R^{1B}$ are $-CH_3$, then $R^3$ is not hydrogen; and when $R^{1A}$ and $R^{1B}$ are $-CH_3$ and $R^3$ is hydrogen, then $R^{2A}$ and $R^{2B}$, together with the carbon atom to which they are attached do not form an oxo group.

In some embodiments, wherein the compound of Formula (A) is a compound of Formula (A-I):

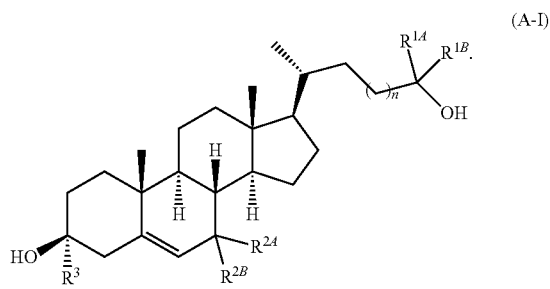

In some embodiments, the compound of Formula (A) is a compound of Formula (A-II):

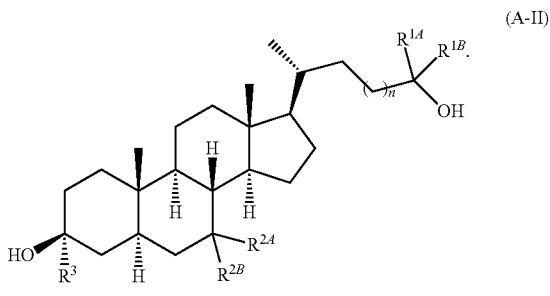

In some embodiments, the compound of Formula (A) is a compound of Formula (A-III):

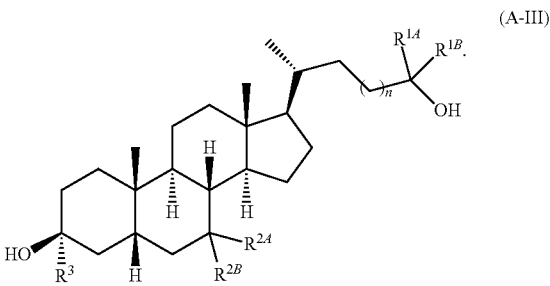

In some embodiments, the compound of Formula (A) is a compound of Formula (A-IV), (A-V), or (A-VI):

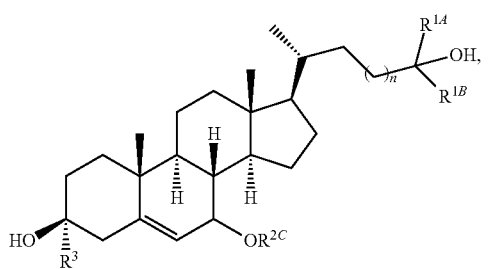
(A-IV)

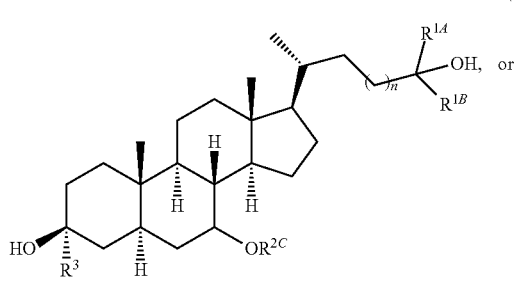
(A-V)

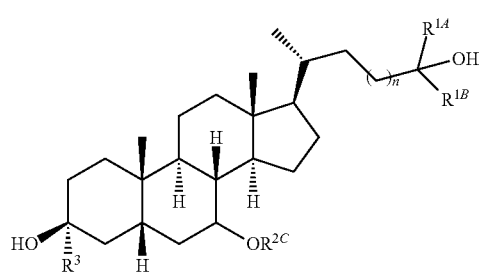
(A-VI)

wherein $R^{2C}$ is hydrogen or alkyl and $R^3$ is alkyl, alkenyl, alkynyl, or —$OR^A$, wherein $R^A$ is alkyl.

In some embodiments, the compound of Formula (A) is a compound of Formula (A-VII), (A-VIII), or (A-IX):

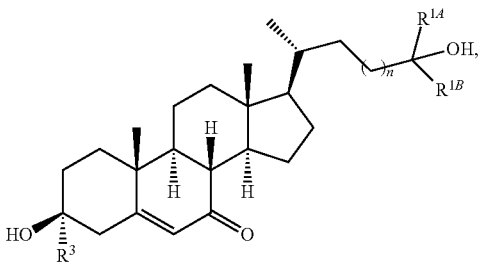
(A-VII)

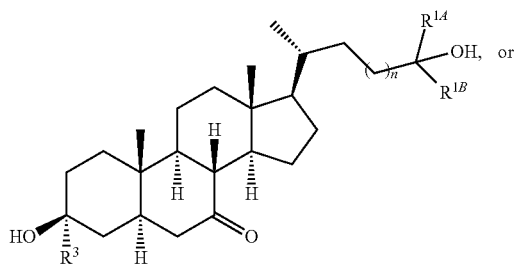
(A-VIII)

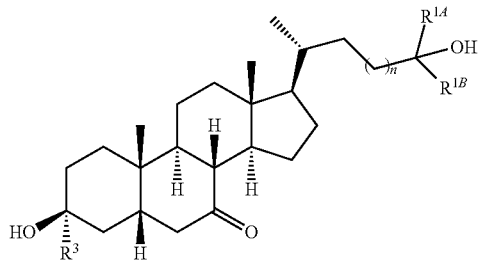
(A-IX)

wherein $R^3$ is alkyl, alkenyl, alkynyl, or —$OR^A$, wherein $R^A$ is alkyl.

In some embodiments, the compound of Formula (A) is a compound of Formula (A-X):

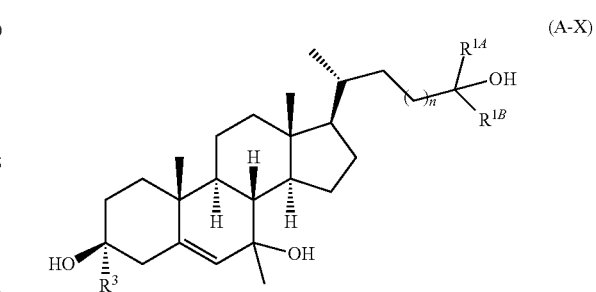
(A-X)

wherein $R^3$ is alkyl, alkenyl, alkynyl, or —$OR^A$, wherein $R^A$ is alkyl.

In some embodiments, the compound of Formula (A) is a compound of Formula (A-XII)

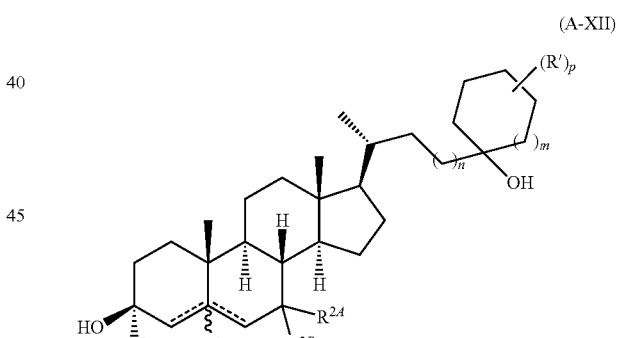
(A-XII)

where R' is alkyl or —$OR^A$, wherein $R^A$ is hydrogen or alkyl; p is 0, 1, 2, 3, 4, 5, or 6; and m is 0, 1, 2, or 3.

In some embodiments, $R^4$ is absent, one of $R^{2A}$ and $R^{2B}$ is —OH, and $R^3$ is not hydrogen.

In some embodiments, each of $R^{1A}$ and $R^{1B}$ is independently unsubstituted or substituted alkyl (e.g., haloalkyl, alkoxyalkyl, —$CH_3$, —$CH_2CH_3$, —$CH(CH_3)_2$, —$CF_3$ or —$CH_2OCH_3$).

In other embodiments, each of $R^{1A}$ and $R^{1B}$ is independently substituted alkyl (e.g., haloalkyl). In some embodiments, $R^{1A}$ and $R^{1B}$ is alkyl (e.g., unsubstituted or substituted alkyl (e.g., —$CH_3$)). In some embodiments, $R^{1A}$ and $R^{1B}$ are —$CH_3$.

In some aspects, $R^{1A}$ is —$CF_3$ or —$CH_2OCH_3$.

In other aspects, $R^{1A}$ is hydrogen and $R^{1B}$ is alkyl, carbocyclyl, heterocyclyl, aryl, or heteroaryl.

In some embodiments, $R^{1A}$ and $R^{1B}$, together with the carbon atom to which they are attached form a 3-8 membered ring.

In some aspects, $R^{1A}$ is substituted alkyl or unsubstituted $C_2$-$C_6$ alkyl and $R^{1B}$ is substituted or unsubstituted $C_1$-$C_6$ alkyl.

In some embodiments, each of $R^{2A}$ and $R^{2B}$ is independently alkyl (e.g., substituted or unsubstituted alkyl). In some aspects, each of $R^{2A}$ and $R^{2B}$ is independently —F.

In other embodiments, $R^{2A}$ and $R^{2B}$ are —CH$_3$ and $R^3$ is alkyl, alkenyl, alkynyl, or —OR$^4$, wherein $R^4$ is alkyl. In some other embodiments, each of $R^{2A}$ and $R^{2B}$ is independently hydrogen and $R^3$ is alkyl (e.g., substituted or unsubstituted alkyl).

In some embodiments, wherein $R^3$ is alkyl (e.g., substituted or unsubstituted alkyl), alkenyl, alkynyl, or —OR$^4$, wherein $R^4$ is alkyl. In other embodiments, $R^3$ is alkyl (e.g., substituted or unsubstituted alkyl).

In one aspect, provided herein are compounds according to Formula (B):

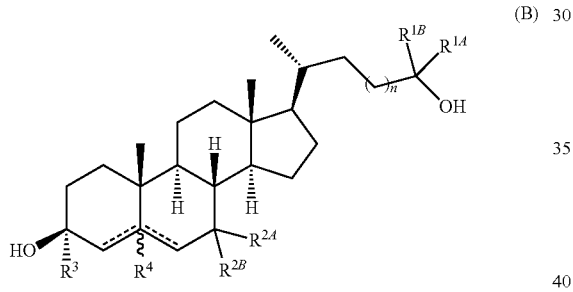

(B)

or a pharmaceutically acceptable salt thereof, wherein:

each of $R^{1A}$ and $R^{1B}$ is independently hydrogen, substituted or unsubstituted alkyl, carbocyclyl, heterocyclyl, aryl, or heteroaryl, or $R^{1A}$ and $R^{1B}$, together with the carbon atom to which they are attached form a 3-8 membered ring;

n is 1 or 2;

each of $R^{2A}$ and $R^{2B}$ is independently hydrogen, halo, —OR$^C$, alkyl, alkenyl, alkynyl, aryl, or heteroaryl, wherein $R^C$ is hydrogen or alkyl, or $R^{2A}$ and $R^{2B}$, together with the carbon atom to which they are attached form an oxo group, wherein $R^{2A}$ and $R^{2B}$ are not both simultaneously hydrogen;

$R^3$ is alkyl, alkenyl, alkynyl, or —OR$^4$, wherein $R^4$ is alkyl;

$R^4$ is absent or hydrogen; and

═══ represents a single or double bond, wherein when one of ═══ is a double bond, the other ═══ is a single bond; when both of ═══ are single bonds, then $R^4$ is hydrogen; and when one of the ═══ is a double bond, $R^4$ is absent.

In some embodiments, n is 1. In other embodiments, n is 2.

In some embodiments, wherein the compound of Formula (B) is a compound of Formula (B-I):

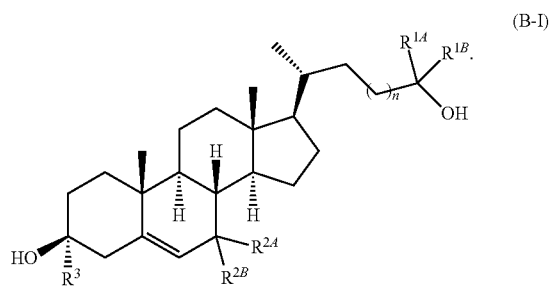

(B-I)

In some embodiments, the compound of Formula (B) is a compound of Formula (B-II):

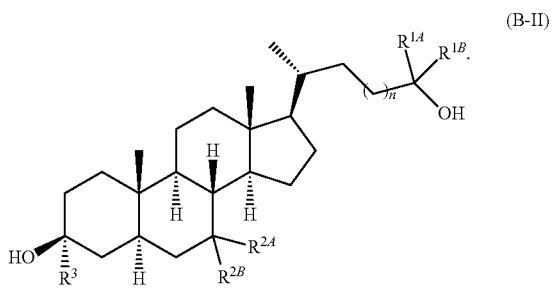

(B-II)

In some embodiments, the compound of Formula (B) is a compound of Formula (B-III):

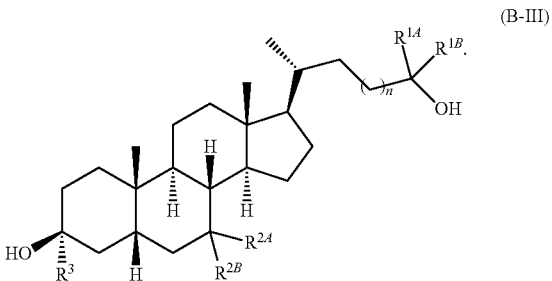

(B-III)

In some embodiments, the compound of Formula (B) is a compound of Formula (B-IV), (B-V), or (B-VI):

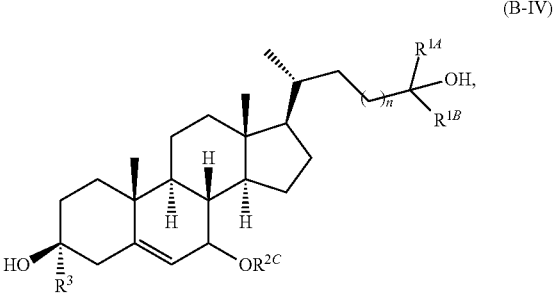

(B-IV)

-continued

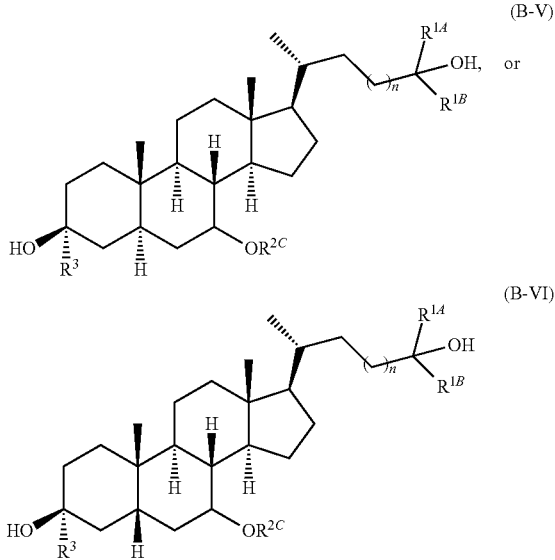

(B-V)

(B-VI)

wherein $R^{2C}$ is hydrogen or alkyl and $R^3$ is alkyl, alkenyl, alkynyl, or $-OR^A$, wherein $R^A$ is alkyl.

In some embodiments, the compound of Formula (B) is a compound of Formula (B-VII), (B-VIII), or (B-IX):

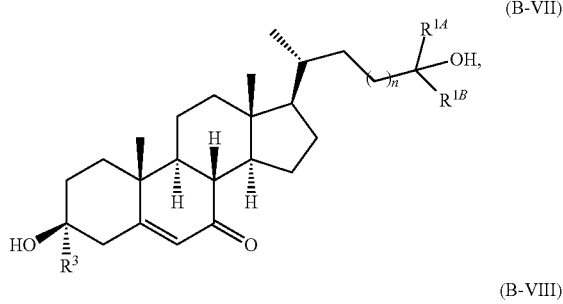

(B-VII)

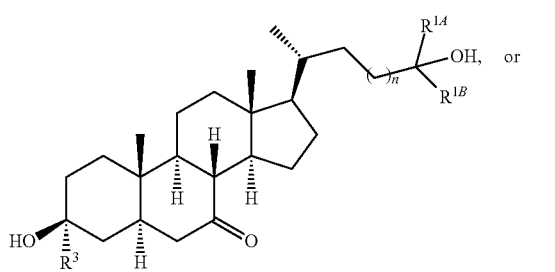

(B-VIII)

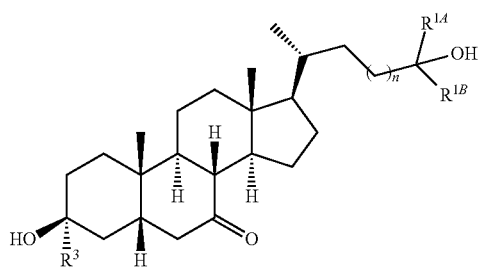

(B-IX)

wherein $R^3$ is alkyl, alkenyl, alkynyl, or —$OR^A$, wherein $R^A$ is alkyl.

In some embodiments, the compound of Formula (B) is a compound of Formula (B-X):

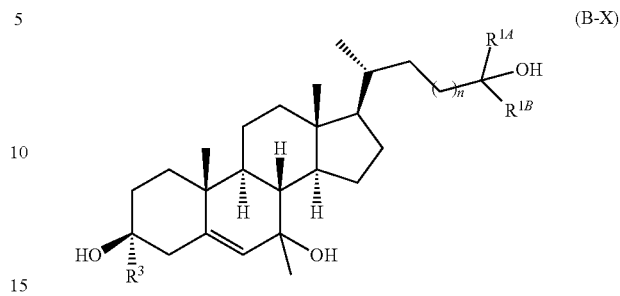

(B-X)

wherein $R^3$ is alkyl, alkenyl, alkynyl, or $-OR^A$, wherein $R^A$ is alkyl.

In some embodiments, the compound of Formula (B) is a compound of Formula (B-XII)

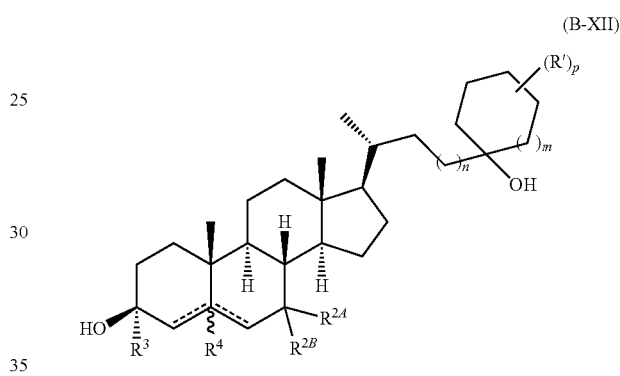

(B-XII)

where R' is alkyl or —$OR^A$, wherein $R^A$ is hydrogen or alkyl; p is 0, 1, 2, 3, 4, 5, or 6; and m is 0, 1, 2, or 3.

In some embodiments, each of $R^{1A}$ and $R^{1B}$ is independently unsubstituted or substituted alkyl (e.g., haloalkyl, alkoxyalkyl, —$CH_3$, —$CH_2CH_3$, —$CH(CH_3)_2$, —$CF_3$ or —$CH_2OCH_3$).

In other embodiments, each of $R^{1A}$ and $R^{1B}$ is independently substituted alkyl (e.g., haloalkyl). In some embodiments, $R^{1A}$ and $R^{1B}$ is alkyl (e.g., unsubstituted or substituted alkyl (e.g., —$CH_3$)). In some embodiments, $R^{1A}$ and $R^{1B}$ are —$CH_3$.

In some aspects, $R^{1A}$ is —$CF_3$ or —$CH_2OCH_3$.

In other aspects, $R^{1A}$ is hydrogen and $R^{1B}$ is alkyl, carbocyclyl, heterocyclyl, aryl, or heteroaryl.

In some embodiments, $R^{1A}$ and $R^{1B}$, together with the carbon atom to which they are attached form a 3-8 membered ring.

In some aspects, $R^{1A}$ is substituted alkyl or unsubstituted $C_2$-$C_6$ alkyl and $R^{1B}$ is substituted or unsubstituted $C_1$-$C_6$ alkyl.

In some embodiments, each of $R^{2A}$ and $R^{2B}$ is independently alkyl (e.g., substituted or unsubstituted alkyl). In some aspects, each of $R^{2A}$ and $R^{2B}$ is independently —F.

In other embodiments, $R^{2A}$ and $R^{2B}$ are —$CH_3$ and $R^3$ is alkyl, alkenyl, alkynyl, or —$OR^A$, wherein $R^A$ is alkyl. In some other embodiments, each of $R^{2A}$ and $R^{2B}$ is independently hydrogen and $R^3$ is alkyl (e.g., substituted or unsubstituted alkyl).

In some embodiments, wherein $R^3$ is alkyl (e.g., substituted or unsubstituted alkyl), alkenyl, alkynyl, or —$OR^A$, wherein $R^A$ is alkyl. In other embodiments, $R^3$ is alkyl (e.g., substituted or unsubstituted alkyl).

In one aspect, provided herein are compounds according to Formula (I):

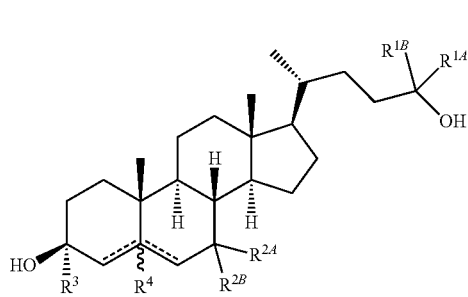

(I)

or a pharmaceutically acceptable salt thereof, wherein:

each of $R^{1A}$ and $R^{1B}$ is independently hydrogen, substituted or unsubstituted alkyl, carbocyclyl, heterocyclyl, aryl, or heteroaryl, or $R^{1A}$ and $R^{1B}$, together with the carbon atom to which they are attached forms a 3-8 membered ring; each of $R^{2A}$ and $R^{2B}$ is independently hydrogen, halo, —$OR^C$, alkyl, alkenyl, alkynyl, aryl, or heteroaryl, wherein $R^C$ is hydrogen or alkyl, or $R^{2A}$ and $R^{2B}$, together with the carbon atom to which they are attached form an oxo group, wherein $R^{2A}$ and $R^{2B}$ are not both simultaneously hydrogen; $R^3$ is hydrogen, alkyl, alkenyl, alkynyl, or —$OR^A$, wherein $R^A$ is alkyl; $R^4$ is absent or hydrogen; and ══ represents a single or double bond, wherein when one of ══ is a double bond, the other ══ is a single bond; when both of ══ are single bonds, then $R^4$ is hydrogen; and when one of the ══ is a double bond, $R^4$ is absent; wherein when $R^{1A}$, $R^3$, and $R^4$ are hydrogen and $R^{1B}$ is unsubstituted isopropyl, then $R^{2A}$ and $R^{2B}$, together with the carbon atom to which they are attached do not form an oxo group; and when $R^4$ is absent, $R^3$ is hydrogen, and $R^{1A}$ and $R^{1B}$ are —$CH_3$, then $R^{2A}$ is not —$CH_3$ and $R^{2B}$ is not —OH.

In some embodiments, $R^{1A}$, $R^3$, and $R^4$ are hydrogen, $R^{1B}$ is unsubstituted isopropyl, and $R^{2A}$ and $R^{2B}$, together with the carbon atom to which they are attached do not form an oxo group.

In some embodiments, $R^4$ is absent, $R^3$ is hydrogen, $R^{1A}$ and $R^{1B}$ are —$CH_3$, $R^{2A}$ is not —$CH_3$, and $R^{2B}$ is not —OH.

In some embodiments, wherein the compound of Formula (I) is a compound of Formula (I-A):

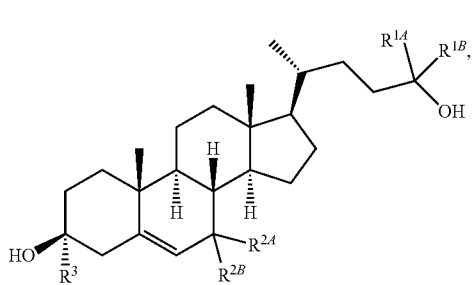

(I-A)

In some embodiments, the compound of Formula (I) is a compound of Formula (I-B):

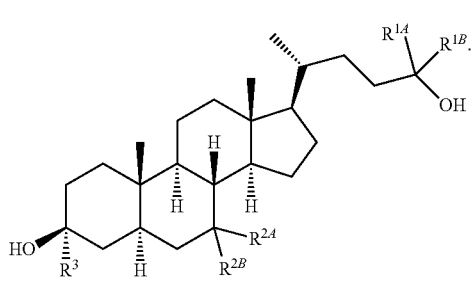

(I-B)

In some embodiments, the compound of Formula (I) is a compound of Formula (I-C):

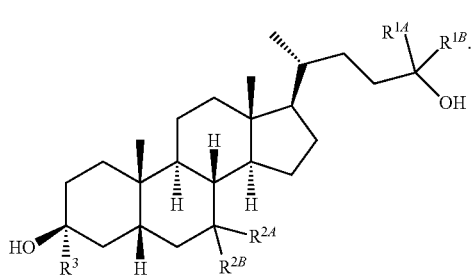

(I-C)

In some embodiments, the compound of Formula (I) is a compound of Formula (I-E), (I-F), or (I-G):

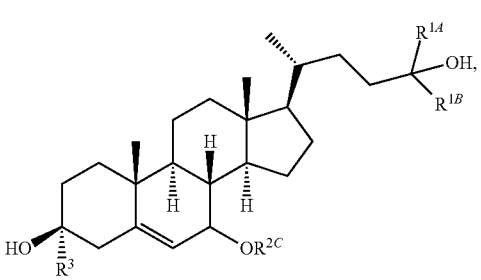

(I-E)

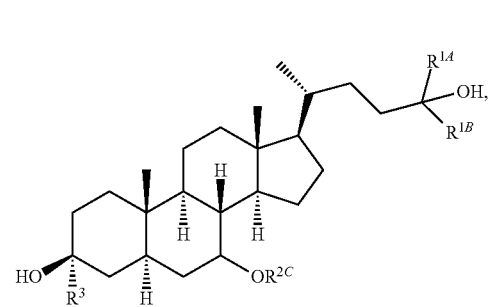

(I-F)

or

-continued

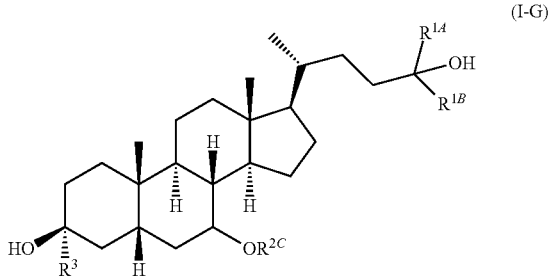
(I-G)

wherein $R^{2C}$ is hydrogen or alkyl and $R^3$ is alkyl, alkenyl, alkynyl, or —$OR^A$, wherein $R^A$ is alkyl.

In some embodiments, the compound of Formula (I) is a compound of Formula (I-H), (I-I), or (I-J):

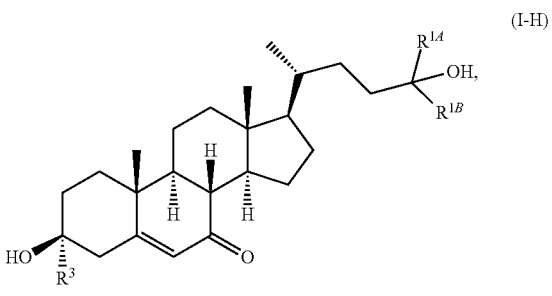
(I-H)

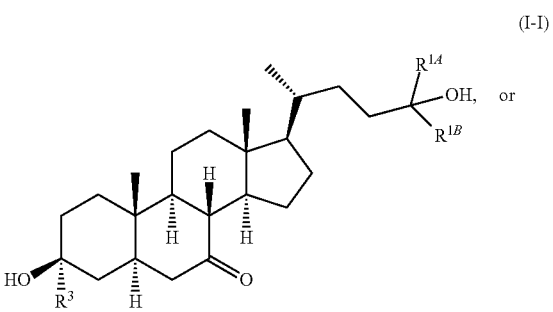
(I-I)

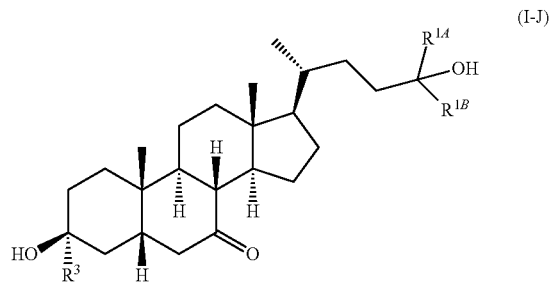
(I-J)

wherein $R^3$ is alkyl, alkenyl, alkynyl, or —$OR^A$, wherein $R^A$ is alkyl.

In some embodiments, the compound of Formula (I) is a compound of Formula (J-K):

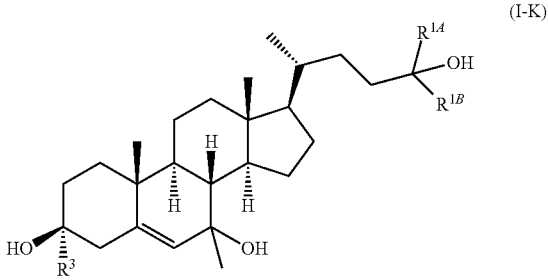
(I-K)

wherein $R^3$ is alkyl, alkenyl, alkynyl, or —$OR^A$, wherein $R^A$ is alkyl.

In some embodiments, the compound of Formula (I) is a compound of Formula (I-M):

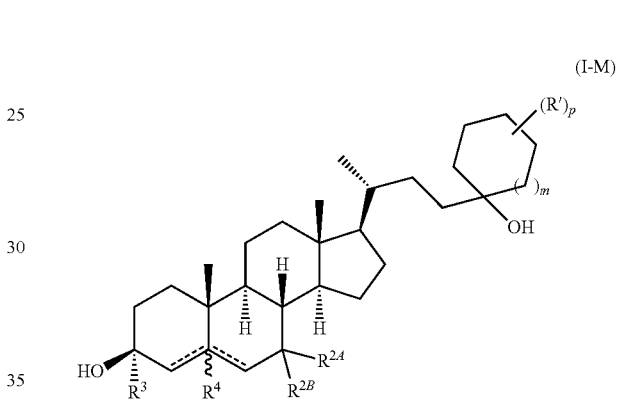
(I-M)

where R' is alkyl or —$OR^A$, wherein $R^A$ is hydrogen or alkyl; p is 0, 1, 2, 3, 4, 5, or 6; and m is 0, 1, 2, or 3.

In some embodiments, each of $R^{1A}$ and $R^{1B}$ is independently unsubstituted or substituted alkyl (e.g., substituted or unsubstituted, —$CH_3$, —$CH_2CH_3$, —$CH(CH_3)_2$, —$CF_3$ or —$CH_2OCH_3$).

In some embodiments, each of $R^{1A}$ and $R^{1B}$ is independently substituted alkyl (e.g., haloalkyl).

In some embodiments, $R^{1A}$ is —$CF_3$ or —$CH_2OCH_3$.

In some embodiments, $R^{1A}$ and $R^{1B}$ is alkyl (e.g, unsubstituted or substituted alkyl (e.g., —$CH_3$)).

In some embodiments, $R^{1A}$ and $R^{1B}$ are —$CH_3$.

In some embodiments, $R^{1A}$ and $R^{1B}$, together with the carbon atom to which they are attached form a 3-8 membered ring.

In some embodiments, $R^{1A}$ is hydrogen and $R^{1B}$ is alkyl, carbocyclyl, heterocyclyl, aryl, or heteroaryl.

In some embodiments, $R^{1A}$ is substituted alkyl or unsubstituted $C_2$-$C_6$ alkyl and $R^{1B}$ is substituted or unsubstituted $C_1$-$C_6$ alkyl.

In some embodiments, each of $R^{2A}$ and $R^{2B}$ is independently alkyl (e.g., substituted or unsubstituted alkyl).

In some embodiments, each of $R^{2A}$ and $R^{2B}$ is independently —F.

In some embodiments, $R^{2A}$ and $R^{2B}$ are —$CH_3$ and $R^3$ is alkyl, alkenyl, alkynyl, or —$OR^A$, wherein $R^A$ is alkyl.

In some embodiments, $R^{2A}$ and $R^{2B}$ are —F.

In some embodiments, $R^3$ is alkyl (e.g. substituted or unsubstituted alkyl), alkenyl, alkynyl, or —$OR^A$, wherein $R^A$ is alkyl.

In some embodiments, $R^3$ is alkyl (e.g, substituted or unsubstituted alkyl).

In some embodiments, each of $R^{2A}$ and $R^{2B}$ is independently hydrogen and $R^3$ is alkyl (e.g., substituted or unsubstituted alkyl).

In one aspect, provided herein are compounds according to Formula (II):

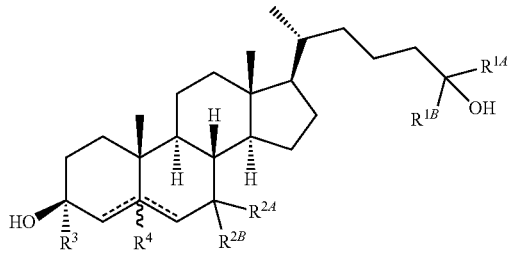

(II)

or a pharmaceutically acceptable salt thereof, wherein:

each of $R^{1A}$ and $R^{1B}$ is independently hydrogen, substituted or unsubstituted alkyl, carbocyclyl, heterocyclyl, aryl, or heteroaryl, or $R^{1A}$ and $R^{1B}$, together with the carbon atom to which they are attached form a 3-8 membered ring;

each of $R^{2A}$ and $R^{2B}$ is independently hydrogen, halo, —$OR^C$, alkyl, alkenyl, alkynyl, aryl, or heteroaryl, wherein $R^C$ is hydrogen or alkyl, or $R^{2A}$ and $R^{2B}$, together with the carbon atom to which they are attached form an oxo group, wherein $R^{2A}$ and $R^{2B}$ are not both simultaneously hydrogen;

$R^3$ is hydrogen, alkyl, alkenyl, alkynyl, or —$OR^A$, wherein $R^A$ is alkyl;

$R^4$ is absent or hydrogen; and

═ represents a single or double bond, wherein when one of ═ is a double bond, the other ═ is a single bond; when both of ═ are single bonds, then $R^4$ is hydrogen; and when one of the ═ is a double bond, $R^4$ is absent;

provided that when $R^4$ is absent, $R^{2A}$ is —OH, $R^{2B}$ is hydrogen or —$CF_3$, and $R^{1A}$ and $R^{1B}$ are —$CH_3$, then $R^3$ is not hydrogen; and when $R^{1A}$ and $R^{1B}$ are —$CH_3$ and $R^3$ is hydrogen, then $R^{2A}$ and $R^{2B}$, together with the carbon atom to which they are attached do not form an oxo group.

In some embodiments, $R^4$ is absent, one of $R^{2A}$ and $R^{2B}$ is —OH, and $R^3$ is not hydrogen.

In some embodiments, the compound of Formula (II) is a compound of Formula (II-A):

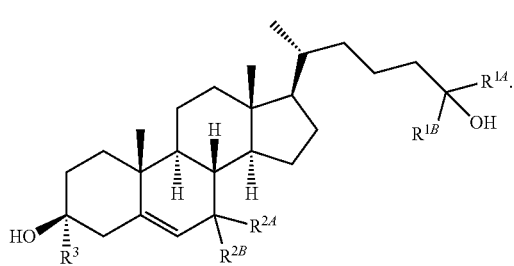

(II-A)

In some embodiments, the compound of Formula (II) is a compound of Formula

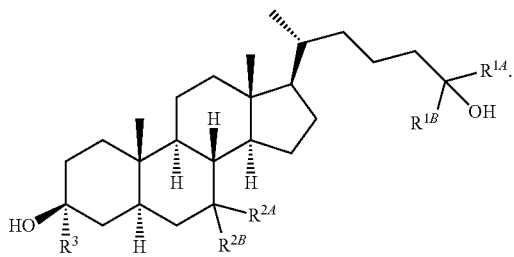

(II-B)

In some embodiments, the compound of Formula (II) is a compound of Formula (II-C):

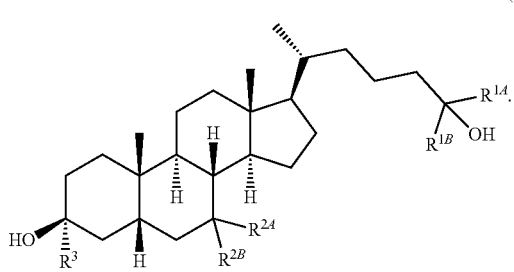

(II-C)

In some embodiments, the compound of Formula (II) is a compound of Formula (II-D):

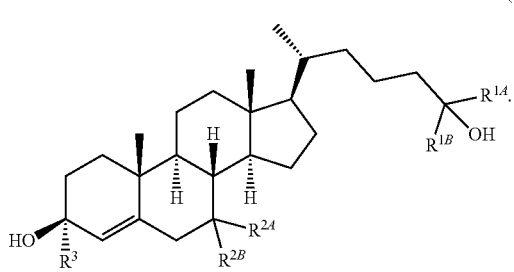

(II-D)

In some embodiments, the compound of Formula (II) is a compound of Formula (II-E), (II-F), or (II-G):

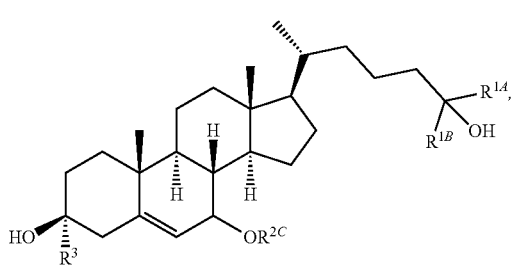

(II-E)

-continued (II-F)

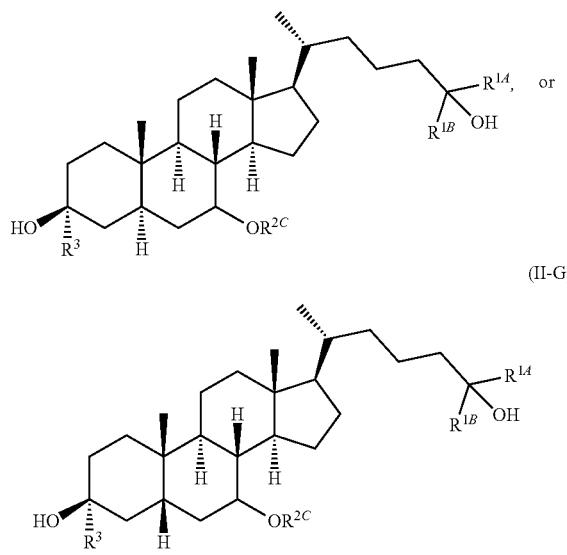

(II-G)

wherein $R^{2C}$ is hydrogen or alkyl (e.g., substituted or unsubstituted alkyl) and $R^3$ is alkyl (e.g., substituted or unsubstituted alkyl).

In some embodiments, the compound of Formula (II) is a compound of Formula (II-H), (II-I), or (II-J):

(II-H)

(II-I)

(II-J)

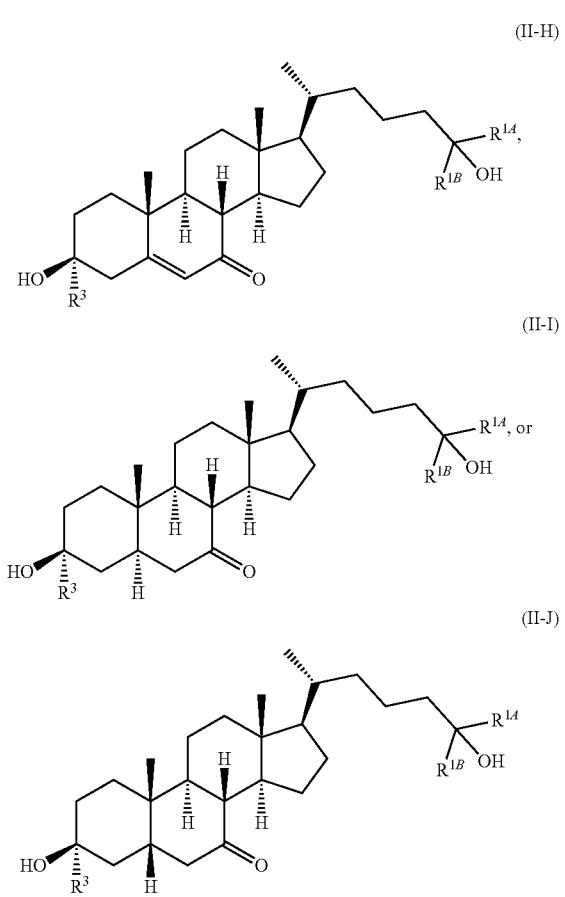

wherein $R^3$ is alkyl, alkenyl, alkynyl, or —$OR^A$, wherein $R^A$ is alkyl.

In some embodiments, the compound of Formula (II) is a compound of Formula (II-K):

(II-K)

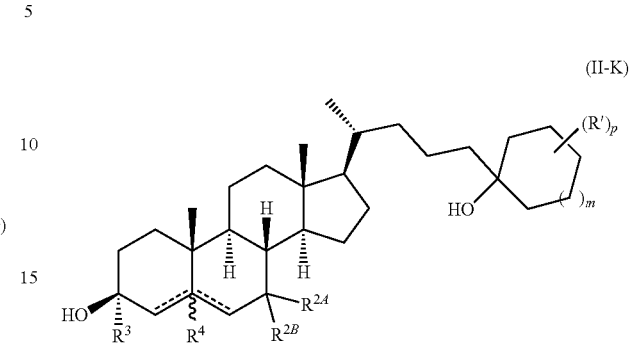

where R' is alkyl or —$OR^A$, wherein $R^A$ is hydrogen or alkyl; p is 0, 1, 2, 3, 4, 5, or 6; and m is 0, 1, or 2, or 3.

In some embodiments, each of $R^{1A}$ and $R^{1B}$ is independently unsubstituted or substituted alkyl (e.g., haloalkyl, alkoxyalkyl, —$CH_3$, —$CH_2CH_3$, —$CH(CH_3)_2$, —$CF_3$ or —$CH_2OCH_3$).

In some embodiments, each of $R^{1A}$ and $R^{1B}$ is independently substituted alkyl (e.g., haloalkyl).

In some embodiments, $R^{1A}$ is —$CF_3$ or —$CH_2OCH_3$.

In some embodiments, $R^{1A}$ and $R^{1B}$ is alkyl (e.g., unsubstituted or substituted alkyl (e.g., —$CH_3$)).

In some embodiments, $R^{1A}$ and $R^{1B}$ are —$CH_3$.

In some embodiments, $R^{1A}$ and $R^{1B}$, together with the carbon atom to which they are attached form a ring.

In some embodiments, $R^{1A}$ is hydrogen and $R^{1B}$ is alkyl, carbocyclyl, heterocyclyl, aryl, or heteroaryl;

In some embodiments, each of $R^{2A}$ and $R^{2B}$ is independently alkyl (e.g., substituted or unsubstituted alkyl).

In some embodiments, $R^3$ is alkyl (e.g., substituted or unsubstituted alkyl).

In some embodiments, each of $R^{2A}$ and $R^{2B}$ is independently hydrogen and $R^3$ is alkyl (e.g., substituted or unsubstituted alkyl).

In some embodiments, each of $R^{2A}$ and $R^{2B}$ is independently —F.

In some embodiments, $R^{2A}$ and $R^{2B}$ are —$CH_3$ and $R^3$ is alkyl, alkenyl, alkynyl, or —$OR^A$, wherein $R^A$ is alkyl.

In some embodiments, $R^{2A}$ and $R^{2B}$ are —F.

In some embodiments, $R^{1A}$ is substituted alkyl or unsubstituted $C_2$-$C_6$ alkyl and $R^{1B}$ is substituted or unsubstituted $C_1$-$C_6$ alkyl.

In some aspects, the compound is a compound of Formula (III):

(III)

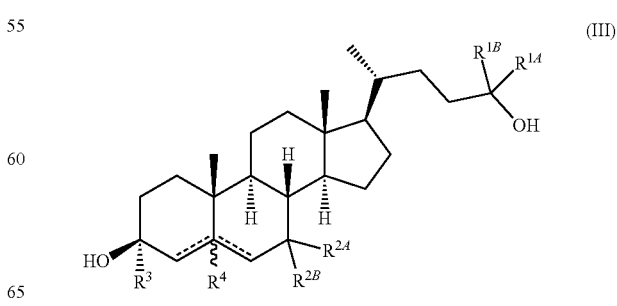

or a pharmaceutically acceptable salt thereof, wherein:

each of $R^{1A}$ and $R^{1B}$ is alkyl;

each of $R^{2A}$ and $R^{2B}$ is independently hydrogen, —$OR^C$, or alkyl, wherein $R^C$ is hydrogen or alkyl, or $R^{2A}$ and $R^{2B}$, together with the carbon atom to which they are attached form an oxo group, wherein $R^{2A}$ and $R^{2B}$ are not both simultaneously hydrogen;

$R^3$ is alkyl;

$R^4$ is absent or hydrogen; and

═ represents a single or double bond, wherein when one of ═ is a double bond, the other ═ is a single bond; when both of ═ are single bonds, then $R^4$ is hydrogen; and when one of the ═ is a double bond, $R^4$ is absent.

In some aspects, $R^{1A}$ and $R^{1B}$ are each —$CH_3$.

In some aspects, $R^{2A}$ and $R^{2B}$ together with the carbon atom to which they are attached form an oxo group.

In some aspects, $R^3$ is —$CH_2CH_3$.

In some aspects, $R^{2A}$ is —OH and $R^{2B}$ is H.

In some aspects, $R^{2A}$ is —$CH_3$ and $R^{2B}$ is H.

In some aspects, $R^{2A}$ is —OH and $R^{2B}$ is —$CH_3$.

In some aspects, $R^{1A}$ is —$CF_3$.

In an alternative embodiment, compounds described herein may also comprise one or more isotopic substitutions. For example, hydrogen may be $^2H$ (D or deuterium) or $^3H$ (T or tritium); carbon may be, for example, $^{13}C$ or $^{14}C$; oxygen may be, for example, $^{18}O$; nitrogen may be, for example, $^{15}N$, and the like. In other embodiments, a particular isotope (e.g., $^3H$, $^{13}C$, $^{14}C$, $^{18}O$, or $^{15}N$) can represent at least 1%, at least 5%, at least 10%, at least 15%, at least 20%, at least 25%, at least 30%, at least 35%, at least 40%, at least 45%, at least 50%, at least 60%, at least 65%, at least 70%, at least 75%, at least 80%, at least 85%, at least 90%, at least 95%, at least 99%, or at least 99.9% of the total isotopic abundance of an element that occupies a specific site of the compound.

Pharmaceutical Compositions

In another aspect, the invention provides a pharmaceutical composition comprising a pharmaceutically acceptable carrier and an effective amount of a compound of Formula (A), Formula (B), Formula (I), Formula (II), or Formula (III).

When employed as pharmaceuticals, the compounds provided herein are typically administered in the form of a pharmaceutical composition. Such compositions can be prepared in a manner well known in the pharmaceutical art and comprise at least one active compound.

In one embodiment, with respect to the pharmaceutical composition, the carrier is a parenteral carrier, oral or topical carrier.

The present invention also relates to a compound of Formula (A), Formula (B), Formula (I), Formula (II), or Formula (III) or pharmaceutical composition thereof for use as a pharmaceutical or a medicament.

Generally, the compounds provided herein are administered in a therapeutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions provided herein can be administered by a variety of routes including oral, rectal, transdermal, subcutaneous, intravenous, intramuscular, and intranasal. Depending on the intended route of delivery, the compounds provided herein are preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as an ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope provided herein.

The compounds provided herein can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences,* 17th edition, 1985, Mack Publishing Company, Easton, Pa., which is incorporated herein by reference.

The above-described components for orally administrable, injectable, or topically administrable compositions are merely representative. Other materials as well as processing techniques and the like are set forth in Part 8 of

*Remington's The Science and Practice of Pharmacy*, 21st edition, 2005, Publisher: Lippincott Williams & Wilkins, which is incorporated herein by reference.

The compounds of this invention can also be administered in sustained release forms or from sustained release drug delivery systems. A description of representative sustained release materials can be found in *Remington's Pharmaceutical Sciences*.

The present invention also relates to the pharmaceutically acceptable formulations of a compound of Formula (A), Formula (B), Formula (I), Formula (II), or Formula (III). In one embodiment, the formulation comprises water. In another embodiment, the formulation comprises a cyclodextrin derivative. The most common cyclodextrins are α-, β- and γ-cyclodextrins consisting of 6, 7 and 8 α-1,4-linked glucose units, respectively, optionally comprising one or more substituents on the linked sugar moieties, which include, but are not limited to, methylated, hydroxyalkylated, acylated, and sulfoalkylether substitution. In certain embodiments, the cyclodextrin is a sulfoalkyl ether β-cyclodextrin, e.g, for example, sulfobutyl ether β-cyclodextrin, also known as Captisol®. See, e.g., U.S. Pat. No. 5,376,645. In certain embodiments, the formulation comprises hexapropyl-β-cyclodextrin. In a more particular embodiment, the formulation comprises hexapropyl-β-cyclodextrin (10-50% in water).

The present invention also relates to the pharmaceutically acceptable acid addition salt of a compound of Formula (A), Formula (B), Formula (I), Formula (II), or Formula (III). The acid which may be used to prepare the pharmaceutically acceptable salt is that which forms a non-toxic acid addition salt, i.e., a salt containing pharmacologically acceptable anions such as the hydrochloride, hydroiodide, hydrobromide, nitrate, sulfate, bisulfate, phosphate, acetate, lactate, citrate, tartrate, succinate, maleate, fumarate, benzoate, para-toluenesulfonate, and the like.

The following formulation examples illustrate representative pharmaceutical compositions that may be prepared in accordance with this invention. The present invention, however, is not limited to the following pharmaceutical compositions.

Exemplary Formulation 1—Tablets: A compound of Formula (A), Formula (B), Formula (I), Formula (II), or Formula (III), or pharmaceutically acceptable salt thereof, may be admixed as a dry powder with a dry gelatin binder in an approximate 1:2 weight ratio. A minor amount of magnesium stearate is added as a lubricant. The mixture is formed into 240-270 mg tablets (80-90 mg of active compound per tablet) in a tablet press.

Exemplary Formulation 2—Capsules: A compound of Formula (A), Formula (B), Formula (I), Formula (II), or Formula (III), or pharmaceutically acceptable salt thereof, may be admixed as a dry powder with a starch diluent in an approximate 1:1 weight ratio. The mixture is filled into 250 mg capsules (125 mg of active compound per capsule).

Exemplary Formulation 3—Liquid: A compound of Formula (A), Formula (B), Formula (I), Formula (II), or Formula (III), or pharmaceutically acceptable salt thereof, (125 mg) may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water may then be added to produce a total volume of 5 mL.

Exemplary Formulation 4— Tablets: A compound of Formula (A), Formula (B), Formula (I), Formula (II), or Formula (III), or pharmaceutically acceptable salt thereof, may be admixed as a dry powder with a dry gelatin binder in an approximate 1:2 weight ratio. A minor amount of magnesium stearate is added as a lubricant. The mixture is formed into 450-900 mg tablets (150-300 mg of active compound) in a tablet press.

Exemplary Formulation 5-Injection: A compound of Formula (A), Formula (B), Formula (I), Formula (II), or Formula (III), or pharmaceutically acceptable salt thereof, may be dissolved or suspended in a buffered sterile saline injectable aqueous medium to a concentration of approximately 5 mg/mL.

Exemplary Formulation 6—Tablets: A compound of Formula (A), Formula (B), Formula (I), Formula (II), or Formula (III), or pharmaceutically acceptable salt thereof, may be admixed as a dry powder with a dry gelatin binder in an approximate 1:2 weight ratio. A minor amount of magnesium stearate is added as a lubricant. The mixture is formed into 90-150 mg tablets (30-50 mg of active compound per tablet) in a tablet press.

Exemplary Formulation 7—Tablets: A compound of Formula (A), Formula (B), Formula (I), Formula (II), or Formula (III), or pharmaceutically acceptable salt thereof, may be may be admixed as a dry powder with a dry gelatin binder in an approximate 1:2 weight ratio. A minor amount of magnesium stearate is added as a lubricant. The mixture is formed into 30-90 mg tablets (10-30 mg of active compound per tablet) in a tablet press.

Exemplary Formulation 8—Tablets: A compound of Formula (A), Formula (B), Formula (I), Formula (II), or Formula (III), or pharmaceutically acceptable salt thereof, may be admixed as a dry powder with a dry gelatin binder in an approximate 1:2 weight ratio. A minor amount of magnesium stearate is added as a lubricant. The mixture is formed into 0.3-30 mg tablets (0.1-10 mg of active compound per tablet) in a tablet press.

Exemplary Formulation 9—Tablets: A compound of Formula (A), Formula (B), Formula (I), Formula (II), or Formula (III), or pharmaceutically acceptable salt thereof, may be admixed as a dry powder with a dry gelatin binder in an approximated 1:2 weight ratio. A minor amount of magnesium stearate is added as a lubricant. The mixture is formed into 150-240 mg tablets (50-80 mg of active compound per tablet) in a tablet press.

Exemplary Formulation 10—Tablets: A compound of Formula (A), Formula (B), Formula (I), Formula (II), or Formula (III), or pharmaceutically acceptable salt thereof, may be admixed as a dry powder with a dry gelatin binder in an approximate 1:2 weight ratio. A minor amount of magnesium stearate is added as a lubricant. The mixture is formed into 270-450 mg tablets (90-150 mg of active compound per tablet) in a tablet press.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

For the prevention and/or treatment of long-term conditions the regimen for treatment usually stretches over many months or years so oral dosing is preferred for patient convenience and tolerance. With oral dosing, one to five and especially two to four and typically three oral doses per day are representative regimens. Using these dosing patterns, each dose provides from about 0.01 to about 20 mg/kg of the compound provided herein, with preferred doses each providing from about 0.1 to about 10 mg/kg, and especially about 1 to about 5 mg/kg.

Transdermal doses are generally selected to provide similar or lower blood levels than are achieved using injection doses.

When used to prevent the onset of a CNS-disorder, the compounds provided herein will be administered to a subject at risk for developing the condition, typically on the advice and under the supervision of a physician, at the dosage levels described above. Subjects at risk for developing a particular condition generally include those that have a family history of the condition, or those who have been identified by genetic testing or screening to be particularly susceptible to developing the condition.

Methods of Treatment and Use

Compounds of the present invention, e.g., a compound of Formula (A), Formula (B), Formula (I), Formula (II), or Formula (III), and pharmaceutically acceptable salts thereof, as described herein, are generally designed to modulate NMDA function, and therefore to act as oxysterols for the treatment and prevention of, e.g., CNS-related conditions in a subject. In some embodiments, the compounds described herein, e.g., a compound of Formula (A), Formula (B), Formula (I), Formula (II), or Formula (III), and pharmaceutically acceptable salts thereof, as described herein, are generally designed to penetrate the blood brain barrier (e.g., designed to be transported across the blood brain barrier). Modulation, as used herein, refers to, for example, the inhibition or potentiation of NMDA receptor function. In certain embodiments, the compound of Formula (A), Formula (B), Formula (I), Formula (II), or Formula (III), or pharmaceutically acceptable salt thereof, acts as a negative allosteric modulator (NAM) of NMDA, and inhibit NMDA receptor function. In certain embodiments, the present invention, e.g., a compound of Formula (A), Formula (B), Formula (I), Formula (II), or Formula (III), or pharmaceutically acceptable salt thereof, acts as a positive allosteric modulator (PAM) of NMDA, and potentiate NMDA receptor function. In certain embodiments, the compound of Formula (A), Formula (B), Formula (I), Formula (II), or Formula (III), or pharmaceutically acceptable salt thereof, blocks or reduces the potentiation or inhibition of NMDA receptor function by a naturally-occurring substrate. Such compounds do not act as negative allosteric modulators (NAMs) or positive allosteric modulators (PAMs) of NMDA. In some embodiments, the disorder is cancer. In some embodiments, the disorder is diabetes. In some embodiments, the disorder is a sterol synthesis disorder. In some embodiments, the disorder is a gastrointestinal (GI) disorder, e.g., constipation, irritable bowel syndrome (IBS), inflammatory bowel disease (IBD) (e.g., ulcerative colitis, Crohn's disease), structural disorders affecting the GI, anal disorders (e.g., hemorrhoids, internal hemorrhoids, external hemorrhoids, anal fissures, perianal abscesses, anal fistula), colon polyps, cancer, or colitis. In some embodiments, the disorder is inflammatory bowel disease.

Exemplary conditions related to NMDA-modulation include, but are not limited to, gastrointestinal (GI) disorder, e.g., constipation, irritable bowel syndrome (IBS), inflammatory bowel disease (IBD) (e.g., ulcerative colitis, Crohn's disease), structural disorders affecting the GI, anal disorders (e.g., hemorrhoids, internal hemorrhoids, external hemorrhoids, anal fissures, perianal abscesses, anal fistula), colon polyps, cancer, colitis, and CNS conditions, e.g., as described herein.

Exemplary conditions (e.g., CNS conditions) related to NMDA-modulation include, but are not limited to, adjustment disorders, anxiety disorders (including obsessive-compulsive disorder, posttraumatic stress disorder, social phobia, generalized anxiety disorder), cognitive disorders (including Alzheimer's disease and other forms of dementia including cortico-basal dementia-progressive supranucelar palsy, frontal-temoral dementia, primary progressive aphasia, Parkinson's disease dementia, and Lewy body dementia), dissociative disorders, eating disorders, mood disorders (including depression (e.g., postpartum depression), bipolar disorder, dysthymic disorder, suicidality), schizophrenia or other psychotic disorders (including schizoaffective disorder), sleep disorders (including insomnia), substance abuse-related disorders, personality disorders (including obsessive-compulsive personality disorder), autism spectrum disorders (including those involving mutations to the Shank group of proteins (e.g., Shank3)), neurodevelopmental disorders (including Rett syndrome), multiple sclerosis, sterol synthesis disorders, Smith-Lemli-Opitz syndrome, pain-(including acute pain, chronic pain, and neuropathic pain), seizure disorders (including status epilepticus and monogenic forms of epilepsy such as Dravet's disease, Tuberous Sclerosis Complex (TSC), and infantile spasms), stroke, subarachnoid hemorrhage, intracerebral hemorrhage, cerebral ischemia, traumatic brain injury, movement disorders (including Huntington's disease and Parkinson's disease) attention deficit disorder, attention deficit hyperactivity disorder, metabolic encephalopathies (including phenylketonuria), post-partum psychosis, syndromes associated with high titers of anti-NMDA receptor antibodies (including anti-NMDA receptor encephalitis), neurodegenerative disorders, neuroinflammation, neuropsychiatric lupus, Niemann-Pick C disorder, and tinnitus.

In certain embodiments, compounds of the present invention, e.g, a compound of Formula (A), Formula (B), Formula (I), Formula (II), or Formula (III), or pharmaceutically acceptable salt thereof, can be used to induce sedation or anesthesia.

In certain embodiments, the compound of Formula (A), Formula (B), Formula (I), Formula (II), or Formula (III), or pharmaceutically acceptable salt thereof, is useful in the treatment or prevention of adjustment disorders, anxiety disorders (including obsessive-compulsive disorder, posttraumatic stress disorder, social phobia, generalized anxiety disorder), cognitive disorders (including Alzheimer's disease and other forms of dementia including cortico-basal dementia-progressive supranucelar palsy, frontal-temoral dementia, primary progressive aphasia, Parkinson's disease dementia, and Lewy body dementia), dissociative disorders, eating disorders, mood disorders (including depression (e.g., postpartum depression), bipolar disorder, dysthymic disorder, suicidality), schizophrenia or other psychotic disorders (including schizoaffective disorder), sleep disorders (including insomnia), substance abuse-related disorders, personality disorders (including obsessive-compulsive personality disorder), autism spectrum disorders (including those involving mutations to the Shank group of proteins (e.g, Shank3)), neurodevelopmental disorders (including Rett syndrome), multiple sclerosis, sterol synthesis disorders, Smith-Lemli-Opitz syndrome, pain (including acute pain, chronic pain, and neuropathic pain), seizure disorders (including status epilepticus and monogenic forms of epilepsy such as Dravet's disease, Tuberous Sclerosis Complex (TSC), and infantile spasms), stroke, subarachnoid hemorrhage, intracerebral hemorrhage, cerebral ischemia, traumatic brain injury, movement disorders (including Huntington's disease and Parkinson's disease) attention deficit disorder, attention deficit hyperactivity disorder, metabolic encephalopathies (including phenylketoneuria), post-partum psychosis, syndromes associated with high titers of anti-NMDA receptor antibodies (including anti-NMDA receptor encephalitis), neurodegenerative disorders, neuroinflammation, neuropsychiatric lupus, Niemann-Pick C disorder, and tinnitus.

In certain embodiments, the compound of Formula (A), Formula (B), Formula (I), Formula (II), or Formula (III), or pharmaceutically acceptable salt thereof, is useful in the treatment or prevention of adjustment disorders, anxiety disorders (including obsessive-compulsive disorder, posttraumatic stress disorder, social phobia, generalized anxiety disorder), cognitive disorders (including Alzheimer's disease and other forms of dementia including cortico-basal dementia-progressive supranucelar palsy, frontal-temoral dementia, primary progressive aphasia, Parkinson's disease dementia, and Lewy body dementia), substance abuse-related disorders, dissociative disorders, eating disorders mood disorders (including depression (e.g., postpartum depression), bipolar disorder, dysthymic disorder, suicidality), schizophrenia or other psychotic disorders (including schizoaffective disorder), personality disorders (including obsessive-compulsive personality disorder), autism spectrum disorders (including those involving mutations to the Shank group of proteins (e.g., Shank3)), or post-partum psychosis.

In certain embodiments, the compound of Formula (A), Formula (B), Formula (I), Formula (II), or Formula (III), or pharmaceutically acceptable salt thereof, is useful in the treatment or prevention of neurodevelopmental disorders (including Rett syndrome), multiple sclerosis, sterol synthesis disorders, Smith-Lemli-Opitz syndrome, pain (including acute pain, chronic pain, and neuropathic pain), seizure disorders (including status epilepticus and monogenic forms of epilepsy such as Dravet's disease, Tuberous Sclerosis Complex (TSC), and infantile spasms), stroke, subarachnoid hemorrhage, intracerebral hemorrhage, cerebral ischemia, traumatic brain injury, movement disorders (including Huntington's disease and Parkinson's disease) attention deficit disorder, attention deficit hyperactivity disorder, metabolic encephalopathies (including phenylketoneuria), syndromes associated with high titers of anti-NMDA receptor antibodies (including anti-NMDA receptor encephalitis), neurodegenerative disorders, neuroinflammation, neuropsychiatric lupus, Niemann-Pick C disorder, or tinnitus.

In some embodiments, a compound of the invention, e.g., a compound of Formula (A), Formula (B), Formula (I), Formula (II), or Formula (III) that acts as a PAM of NMDA receptor function can be useful in the treatment or prevention of conditions (e.g., CNS-related conditions) including schizophrenia or other psychotic disorders (including schizoaffective disorder), sleep disorders (including insomnia), autism spectrum disorders (including those involving mutations to the Shank group of proteins (e.g., Shank3)), multiple sclerosis, movement disorders (including Huntington's disease and Parkinson's disease), attention deficit disorder, attention deficit hyperactivity disorder, metabolic encephalopathies (including phenylketoneuria), post-partum psychosis, and syndromes associated with high titers or anti-NMDA receptor antibodies (including anti-NMDA receptor encephalitis).

In some embodiments, a compound of the invention, e.g., a compound of Formula (A), Formula (B), Formula (I), Formula (II), or Formula (III), that acts as a NAM of NMDA receptor function can be useful in the treatment or prevention of conditions (e.g., CNS-related conditions) including anxiety disorders (including obsessive-compulsive disorder, posttraumatic stress disorder, social phobia, generalized anxiety disorder), mood disorders (including depression (e.g., postpartum depression), bipolar disorder, dysthymic disorder, suicidality), personality disorders (including obsessive-compulsive personality disorder), neurodevelopmental disorders (including Rett syndrome), pain (including acute and chronic pain), seizure disorders (including status epilepticus and monogenic forms of epilepsy such as Dravet's disease, and Tuberous Sclerosis Complex (TSC)), stroke, traumatic brain injury, adjustment disorders, neuropsychiatric lupus, and tinnitus.

In some embodiments, a compound of the invention, e.g., a compound of Formula (A), Formula (B), Formula (I), Formula (II), or Formula (III), that acts as a PAM or a NAM of NMDA receptor function can be useful in the treatment or prevention of conditions (e.g., CNS-related conditions) including cognitive disorders (including Alzheimer's disease and other forms of dementia including cortico-basal dementia-progressive supranucelar palsy, frontal-temoral dementia, primary progressive aphasia, Parkinson's disease dementia, and Lewy body dementia), sterol synthesis disorders, and eating disorders.

In another aspect, provided is a method of treating or preventing brain excitability in a subject susceptible to or afflicted with a condition associated with brain excitability, comprising administering to the subject an effective amount of a compound of the present invention, e.g., a compound of Formula (A), Formula (B), Formula (I), Formula (II), or Formula (III), or a pharmaceutically acceptable salt thereof.

In yet another aspect, the present invention provides a combination of a compound of the present invention, e.g., a compound of Formula (A), Formula (B), Formula (I), Formula (II), or Formula (III), or pharmaceutically acceptable salt thereof, and another pharmacologically active agent. The compounds provided herein can be administered as the sole active agent or they can be administered in combination with other agents. Administration in combination can proceed by any technique apparent to those of skill in the art including, for example, separate, sequential, concurrent and alternating administration.

Movement Disorders

Also described herein are methods for treating a movement disorder. As used herein, "movement disorders" refers to a variety of diseases and disorders that are associated with hyperkinetic movement disorders and related abnormalities in muscle control. Exemplary movement disorders include, but are not limited to, Parkinson's disease and Parkinsonism (defined particularly by bradykinesia), dystonia, chorea and Huntington's disease, ataxia, tremor (e.g., essential tremor), myoclonus and startle, tics and Tourette syndrome, Restless legs syndrome, stiff person syndrome; and gait disorders.

Tremor is an involuntary, at times rhythmic, muscle contraction and relaxation that can involve oscillations or twitching of one or more body parts (e.g., hands, arms, eyes, face, head, vocal folds, trunk, legs). Tremor includes hereditary, degenerative, and idiopathic disorders such as Wilson's disease, Parkinson's disease, and essential tremor, respectively; metabolic diseases (e.g., thyroid-parathyroid-, liver disease and hypoglycemia); peripheral neuropathies (associated with Charcot-Marie-Tooth, Roussy-Levy, diabetes mellitus, complex regional pain syndrome); toxins (nicotine, mercury, lead, CO, Manganese, arsenic, toluene); drug-induced (narcoleptics, tricyclics, lithium, cocaine, alcohol, adrenaline, bronchodilators, theophylline, caffeine, steroids, valproate, amiodarone, thyroid hormones, vincristine); and psychogenic disorders. Clinical tremor can be classified into physiologic tremor, enhanced physiologic tremor, essential tremor syndromes (including classical essential tremor, primary orthostatic tremor, and task- and position-specific tremor), dystonic tremor, parkinsonian tremor, cerebellar tremor, Holmes' tremor (i.e., rubral tremor), palatal tremor, neuropathic tremor, toxic or drug-induced tremor, and psychogenic tremor. Other forms of tremor include cerebellar tremor or intention tremor, dystonic tremor, essential tremor, orthostatic tremor, parkinsonian tremor, physiological tremor, psychogenic tremor, or rubral tremor.

Cerebellar tremor or intention tremor is a slow, broad tremor of the extremities that occurs after a purposeful movement. Cerebellar tremor is caused by lesions in or damage to the cerebellum resulting from, e.g., tumor, stroke, disease (e.g., multiple sclerosis, an inherited degenerative disorder).

Dystonic tremor occurs in individuals affected by dystonia, a movement disorder in which sustained involuntary muscle contractions cause twisting and repetitive motions and/or painful and abnormal postures or positions. Dystonic tremor may affect any muscle in the body. Dystonic tremors occurs irregularly and often can be relieved by complete rest.

Essential tremor or benign essential tremor is the most common type of tremor. Essential tremor may be mild and nonprogressive in some, and may be slowly progressive, starting on one side of the body but affect both sides within 3 years. The hands are most often affected, but the head, voice, tongue, legs, and trunk may also be involved. Tremor frequency may decrease as the person ages, but severity may increase. Heightened emotion, stress, fever, physical exhaustion, or low blood sugar may trigger tremors and/or increase their severity. Symptoms generally evolve over time and can be both visible and persistent following onset.

Orthostatic tremor is characterized by fast (e.g., greater than 12 Hz) rhythmic muscle contractions that occurs in the legs and trunk immediately after standing. Cramps are felt in the thighs and legs and the patient may shake uncontrollably when asked to stand in one spot. Orthostatic tremor may occur in patients with essential tremor.

Parkinsonian tremor is caused by damage to structures within the brain that control movement. Parkinsonian tremor is often a precursor to Parkinson's disease and is typically seen as a "pill-rolling" action of the hands that may also affect the chin, lips, legs, and trunk. Onset of parkinsonian tremor typically begins after age 60. Movement starts in one limb or on one side of the body and can progress to include the other side.

Physiological tremor can occur in normal individuals and have no clinical significance. It can be seen in all voluntary muscle groups. Physiological tremor can be caused by certain drugs, alcohol withdrawal, or medical conditions including an overactive thyroid and hypoglycemia. The tremor classically has a frequency of about 10 Hz.

Psychogenic tremor or hysterical tremor can occur at rest or during postural or kinetic movement. Patient with psychogenic tremor may have a conversion disorder or another psychiatric disease.

Rubral tremor is characterized by coarse slow tremor which can be present at rest, at posture, and with intention. The tremor is associated with conditions that affect the red nucleus in the midbrain, classical unusual strokes.

Parkinson's disease affects nerve cells in the brain that produce dopamine. Symptoms include muscle rigidity, tremors, and changes in speech and gait. Parkinsonism is characterized by tremor, bradykinesia, rigidity, and postural instability. Parkinsonism shares symptoms found in Parkinson's disease, but is a symptom complex rather than a progressive neurodegenerative disease.

Dystonia is a movement disorder characterized by sustained or intermittent muscle contractions causing abnormal, often repetitive movements or postures. Dystonic movements can be patterned, twisting, and may be tremulous. Dystonia is often initiated or worsened by voluntary action and associated with overflow muscle activation.

Chorea is a neurological disorder characterized by jerky involuntary movements typically affecting the shoulders, hips, and face.

Huntington's Disease is an inherited disease that causes nerve cells in the brain to waste away. Symptoms include uncontrolled movements, clumsiness, and balance problems. Huntington's disease can hinder walk, talk, and swallowing.

Ataxia refers to the loss of full control of bodily movements, and may affect the fingers, hands, arms, legs, body, speech, and eye movements.

Myoclonus and Startle is a response to a sudden and unexpected stimulus, which can be acoustic, tactile, visual, or vestibular.

Tics are an involuntary movement usually onset suddenly, brief, repetitive, but non-rhythmical, typically imitating normal behavior and often occurring out of a background of normal activity. Tics can be classified as motor or vocal, motor tics associated with movements while vocal tics associated with sound. Tics can be characterized as simple or complex. For example simple motor tics involve only a few muscles restricted to a specific body part.

Tourette Syndrome is an inherited neuropsychiatric disorder with onset in childhood, characterized by multiple motor tics and at least one vocal tic.

Restless Legs Syndrome is a neurologic sensorimotor disorder characterized by an overwhelming urge to move the legs when at rest.

Stiff Person Syndrome is a progressive movement disorder characterized by involuntary painful spasms and rigidity of muscles, usually involving the lower back and legs.

Stiff-legged gait with exaggerated lumbar hyperlordosis typically results. Characteristic abnormality on EMG recordings with continuous motor unit activity of the paraspinal axial muscles is typically observed. Variants include "stiff-limb syndrome" producing focal stiffness typically affecting distal legs and feet.

Gait disorders refer to an abnormality in the manner or style of walking, which results from neuromuscular, arthritic, or other body changes. Gait is classified according to the system responsible for abnormal locomotion, and include hemiplegic gait, diplegic gait, neuropathic gait, myopathic gait, parkinsonian gait, choreiform gait, ataxic gait, and sensory gait.

Mood Disorders

Also provided herein are methods for treating a mood disorder, for example clinical depression, postnatal depression or postpartum depression, perinatal depression, atypical depression, melancholic depression, psychotic major depression, cationic depression, seasonal affective disorder, dysthymia, double depression, depressive personality disorder, recurrent brief depression, minor depressive disorder, bipolar disorder or manic depressive disorder, depression caused by chronic medical conditions, treatment-resistant depression, refractory depression, suicidality, suicidal ideation, or suicidal behavior.

Clinical depression is also known as major depression, major depressive disorder (MDD), severe depression, unipolar depression, unipolar disorder, and recurrent depression, and refers to a mental disorder characterized by pervasive and persistent low mood that is accompanied by low self-esteem, and loss of interest or pleasure in normally enjoyable activities. Some people with clinical depression have trouble sleeping, lose weight, and generally feel agitated and irritable. Clinical depression affects how an individual feels, thinks, and behaves and may lead to a variety of emotional and physical problems. Individuals with clinical depression may have trouble doing day-to-day activities and make an individual feel as if life is not worth living.

Postnatal depression (PND) is also referred to as postpartum depression (PPD), and refers to a type of clinical depression that affects women after childbirth. Symptoms can include sadness, fatigue, changes in sleeping and eating habits, reduced sexual desire, crying episodes, anxiety, and irritability. In some embodiments, the PND is a treatment-resistant depression (e.g., a treatment-resistant depression as described herein). In some embodiments, the PND is refractory depression (e.g., a refractory depression as described herein).

In some embodiments, a subject having PND also experienced depression, or a symptom of depression during pregnancy. This depression is referred to herein as) perinatal depression. In an embodiment, a subject experiencing perinatal depression is at increased risk of experiencing PND.

Atypical depression (AD) is characterized by mood reactivity (e.g., paradoxical anhedonia) and positivity, significant weight gain or increased appetite. Patients suffering from AD also may have excessive sleep or somnolence (hypersomnia), a sensation of limb heaviness, and significant social impairment as a consequence of hypersensitivity to perceived interpersonal rejection.

Melancholic depression is characterized by loss of pleasure (anhedonia) in most or all activities, failures to react to pleasurable stimuli, depressed mood more pronounced than that of grief or loss, excessive weight loss, or excessive guilt.

Psychotic major depression (PMD) or psychotic depression refers to a major depressive episode, in particular pf melancholic nature, where the individual experiences psychotic symptoms such as delusions and hallucinations.

Catatonic depression refers to major depression involving disturbances of motor behavior and other symptoms. An individual may become mute and stuporose, and either is immobile or exhibits purposeless or bizarre movements.

Seasonal affective disorder (SAD) refers to a type of seasonal depression wherein an individual has seasonal patterns of depressive episodes coming on in the fall or winter.

Dysthymia refers to a condition related to unipolar depression, where the same physical and cognitive problems are evident. They are not as severe and tend to last longer (e.g at least 2 years).

Double depression refers to fairly depressed mood (dysthymia) that lasts for at least 2 years and is punctuated by periods of major depression.

Depressive Personality Disorder (DPD) refers to a personality disorder with depressive features.

Recurrent Brief Depression (RBD) refers to a condition in which individuals have depressive episodes about once per month, each episode lasting 2 weeks or less and typically less than 2-3 days.

Minor depressive disorder or minor depression refers to a depression in which at least 2 symptoms are present for 2 weeks.

Bipolar disorder or manic depressive disorder causes extreme mood swings that include emotional highs (mania or hypomania) and lows (depression). During periods of mania the individual may feel or act abnormally, happy, energetic, or irritable. They often make poorly thought out decisions with little regard to the consequences. The need for sleep is usually reduced. During periods of depression there may be crying, poor eye contact with others, and a negative outlook on life. The risk of suicide among those with the disorder is high at greater than 6% over 20 years, while self-harm occurs in 30-40%. Other mental health issues such as anxiety disorder and substance use disorder are commonly associated with bipolar disorder.

Depression caused by chronic medical conditions refers to depression caused by chronic medical conditions such as cancer or chronic pain, chemotherapy, chronic stress.

Treatment-resistant depression refers to a condition where the individuals have been treated for depression, but the symptoms do not improve. For example, antidepressants or psychological counseling (psychotherapy) do not ease depression symptoms for individuals with treatment-resistant depression. In some cases, individuals with treatment-resistant depression improve symptoms, but come back. Refractory depression occurs in patients suffering from depression, who are resistant to standard pharmacological treatments, including tricyclic antidepressants, MAOIs, SSRIs, and double and triple uptake inhibitors and/or anxiolytic drugs, as well as non-pharmacological treatments (e.g., psychotherapy, electroconvulsive therapy, vagus nerve stimulation and/or transcranial magnetic stimulation).

Suicidality, suicidal ideation, suicidal behavior refers to the tendency of an individual to commit suicide. Suicidal ideation concerns thoughts about or an unusual preoccupation with suicide. The range of suicidal ideation varies greatly, from e.g., fleeting thoughts to extensive thoughts, detailed planning, role playing, incomplete attempts. Symptoms include talking about suicide, getting the means to commit suicide, withdrawing from social contact, being preoccupied with death, feeling trapped or hopeless about a situation, increasing use of alcohol or drugs, doing risky or self-destructive things, saying goodbye to people as if they won't be seen again.

Symptoms of depression include persistent anxious or sad feelings, feelings of helplessness, hopelessness, pessimism, worthlessness, low energy, restlessness, difficulty sleeping, sleeplessness, irritability, fatigue, motor challenges, loss of interest in pleasurable activities or hobbies, loss of concentration, loss of energy, poor self-esteem, absence of positive thoughts or plans, excessive sleeping, overeating, appetite loss, insomnia, self-harm, thoughts of suicide, and suicide attempts. The presence, severity, frequency, and duration of symptoms may vary on a case to, case basis. Symptoms of depress ion, and relief of the same, may be ascertained by a physician or psychologist (e.g., by a mental state examination).

Anxiety Disorders

Provided herein are methods for treating anxiety disorders. Anxiety disorder is a blanket term covering several different forms of abnormal and pathological fear and anxiety. Current psychiatric diagnostic criteria recognize a wide variety of anxiety disorders.

Generalized anxiety disorder is a common chronic disorder characterized by long-lasting anxiety that is not focused on any one object or situation. Those suffering from generalized anxiety experience non-specific persistent fear and worry and become overly concerned with everyday matters. Generalized anxiety disorder is the most common anxiety disorder to affect older adults.

In panic disorder, a person suffers from brief attacks of intense terror and apprehension, often marked by trembling, shaking, confusion, dizziness, nausea, difficulty breathing. These panic attacks, defined by the APA as fear or discomfort that abruptly arises, and peaks in less than ten minutes, can last for, several hours and can be triggered by stress, fear, or even exercise; although the specific cause is not always apparent. In addition to recurrent unexpected panic attacks, a diagnosis of panic disorder also requires that said attacks have chronic consequences: either worry over the attacks' potential implications, persistent fear of future attacks, or significant changes in behavior related to the attacks. Accordingly, those suffering from panic disorder experience symptoms even outside of specific panic episodes. Often, normal changes in heartbeat are noticed by a panic sufferer, leading them to think something is wrong with their heart or they are about to have another panic attack. In some cases, a heightened awareness (hypervigilance) of body functioning occurs during panic attacks, wherein any perceived physiological change is interpreted as a possible life threatening illness (i.e. extreme hypochondriasis).

Obsessive compulsive disorder is a type of anxiety disorder primarily characterized by repetitive obsessions (distressing, persistent, and intrusive thoughts or images) and compulsions (urges to perform specific acts or rituals). The OCD thought pattern may be likened to superstitions insofar as it involves a belief in a causative relationship where, in reality, one does not exist. Often the process is entirely illogical; for example, the compulsion of walking in a certain pattern may be employed to alleviate the obsession of impending harm. And in many cases, the compulsion is entirely inexplicable, simply an urge to complete a ritual triggered by nervousness. In a minority of cases, sufferers of OCD may only experience obsessions, with no overt compulsions; a much smaller number of sufferers experience only compulsions.

The single largest category of anxiety disorders is that of phobia, which includes all cases in which fear and anxiety is triggered by a specific stimulus or situation. Sufferers typically anticipate terrifying consequences from encountering the object of their fear, which can be anything from an animal to a location to a bodily fluid.

Post-traumatic stress disorder or PTSD is an anxiety disorder which results from a traumatic, experience. Post-traumatic stress can result from, an extreme situation, such as combat, rape, hostage situations, or even serious accident. It can also result from long term (chronic) exposure to a severe stressor, for example soldiers who endure individual battles but cannot cope with continuous combat. Common symptoms include flashbacks, avoidant behaviors, and depression.

Epilepsy

Epilepsy is a brain, disorder characterized by repeated, seizures over time. Types of epilepsy can include, but are not limited to generalized epilepsy, e.g., childhood absence epilepsy, juvenile myoclonic epilepsy, epilepsy with grand-mal seizures on awakening, West syndrome, Lennox-Gastaut syndrome, partial epilepsy, e.g., temporal lobe epilepsy, frontal lobe epilepsy, benign focal epilepsy of childhood.

Epileptogenesis

Epileptogenesis is a gradual process by which a normal brain develops epilepsy (a chronic condition in which seizures occur). Epileptogenesis results from neuronal damage precipitated by the initial insult (e.g., status epilepticus).

Status Epilepticus (SE)

Status epilepticus (SE) can include, e.g., convulsive status epilepticus, e.g., early status epilepticus, established status epilepticus, refractory status epilepticus, super-refractory status epilepticus; non-convulsive status epilepticus, e.g., generalized status epilepticus, complex partial status epilepticus; generalized periodic epileptiform discharges; and periodic lateralized epileptiform discharges. Convulsive status epilepticus is characterized by the presence of convulsive status epileptic seizures, and can include early status epilepticus, established status epilepticus, refractory status epilepticus, super-refractory status epilepticus. Early status epilepticus is treated with a first line therapy. Established status epilepticus is characterized by status epileptic seizures which persist despite treatment with a first line therapy, and a second line therapy is administered. Refractory status epilepticus is characterized by status epileptic seizures which persist despite treatment with a first line and a second line therapy, and a general anesthetic is generally administered. Super refractory status epilepticus is characterized by status epileptic seizures which persist despite treatment with a first line therapy, a second line therapy, and a general anesthetic for 24 hours or more.

Non-convulsive status epilepticus can include, e.g., focal non-convulsive status epilepticus, e.g., complex partial non-convulsive status epilepticus, simple partial non-convulsive status epilepticus, subtle non-convulsive status epilepticus; generalized non-convulsive status epilepticus, e.g., late onset absence non-convulsive status epilepticus, atypical absence non-convulsive status epilepticus, or typical absence non-convulsive status epilepticus.

Seizure

A seizure is the physical findings or changes in behavior that occur after an episode of abnormal electrical activity in the brain. The term "seizure" is often used interchangeably with "convulsion," Convulsions are when a person's body shakes rapidly and uncontrollably. During convulsions, the person's muscles contract and relax repeatedly.

Based on the type of behavior and brain activity, seizures are divided into two broad categories: generalized and partial (also called local or focal). Classifying the type of seizure helps doctors diagnose whether or not a patient has epilepsy.

Generalized seizures are produced by electrical impulses from throughout the entire brain, whereas partial seizures are produced (at least initially) by electrical impulses in a relatively small part of the brain. The part of the brain generating the seizures is sometimes called the focus.

There are six types of generalized seizures. The most common and dramatic, and therefore the most well-known, is the generalized convulsion, also called the grand-mal seizure. In this type of seizure, the patient loses consciousness and usually collapses. The loss of consciousness is followed by generalized body stiffening (called the "tonic" phase of the seizure) for 30 to 60 seconds, then by violent jerking (the "clonic" phase) for 30 to 60 seconds, after which the patient goes into a deep sleep (the "postictal" or after-seizure phase). During grand-mal seizures, injuries and accidents may occur, such as tongue biting and urinary incontinence.

Absence seizures cause a short loss of consciousness (just a few seconds) with few or no symptoms. The patient, most often a child, typically interrupts an activity and stares blankly. These seizures begin and end abruptly and may occur several times a day. Patients are usually not aware that they are having a seizure, except that they may be aware of "losing time."

Myoclonic seizures consist of sporadic jerks, usually on both sides of the body. Patients sometimes describe the jerks as brief electrical shocks. When violent, these seizures may result in dropping or involuntarily throwing objects.

Clonic seizures are repetitive, rhythmic jerks that involve both sides of the body at the same time.

Tonic seizures are characterized by stiffening of the muscles.

Atonic seizures consist of a sudden and general loss of muscle tone, particularly in the arms and legs, which often results in a fall.

Seizures described herein can include epileptic seizures; acute repetitive seizures; cluster seizures; continuous seizures; unremitting seizures; prolonged seizures; recurrent seizures; status epilepticus seizures, e.g., refractory convulsive status epilepticus, non-convulsive status epilepticus seizures; refractory seizures; myoclonic seizures; tonic seizures; tonic-clonic seizures; simple partial seizures; complex partial seizures; secondarily generalized seizures; atypical absence seizures; absence seizures; atonic seizures; benign Rolandic seizures; febrile seizures; emotional seizures; focal seizures; gelastic seizures; generalized onset seizures; infantile spasms; Jacksonian seizures; massive bilateral myoclonus seizures; multifocal seizures; neonatal onset seizures; nocturnal seizures; occipital lobe seizures; post traumatic seizures; subtle seizures; Sylvan seizures; visual reflex seizures; or withdrawal seizures. In some embodiments, the seizure is a generalized seizure associated with Dravet Syndrome, Lennox-Gastaut Syndrome, Tuberous Sclerosis Complex, Rett Syndrome or PCDH19 Female Pediatric Epilepsy.

Example 1: Synthesis of 61

Overview:

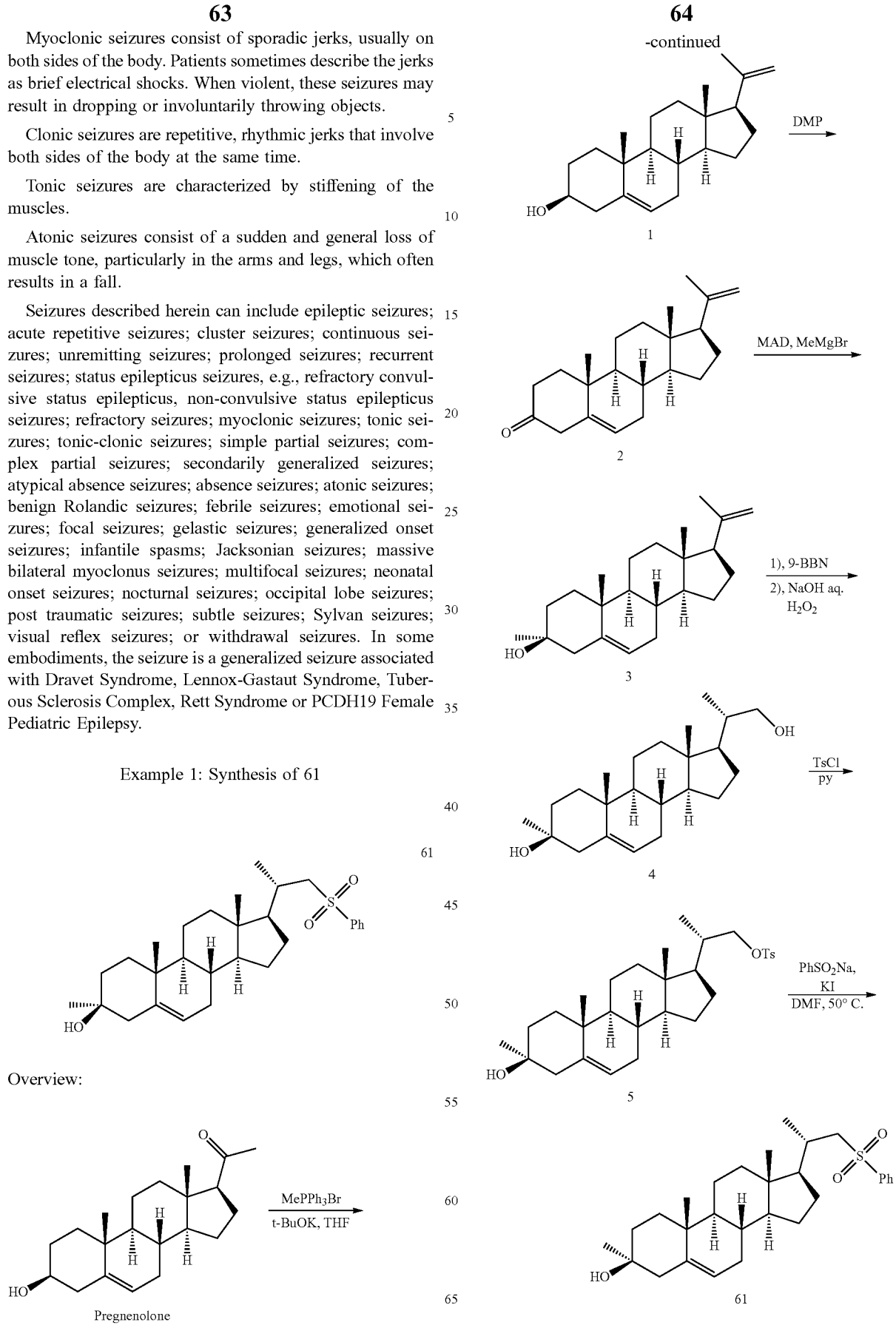

Synthesis of 1

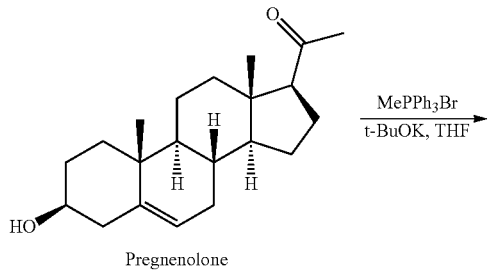

Pregnenolone

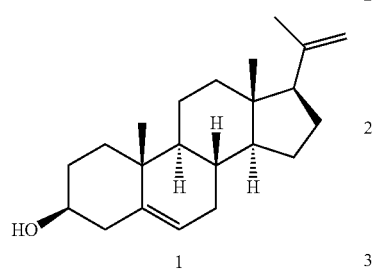

1

To a mixture of MePPh$_3$Br (1.28 kg, 3.6 mol) in THF (4.5 L) was added 1-BuOK (404 g, 3.6 mol) at 15° C. under N$_2$. The resulting mixture was stirred at 50° C. for 30 mins. Pregnenolone (950 g, 2.9 mol) was added in portions below 65° C. The reaction mixture was stirred at 50° C. for 1 hour. The combined mixture was quenched with saturated NH$_4$Cl aqueous (1 L) at 15° C. THF layer was separated. The aqueous was extracted with EtOAc (2×2 L). The combined organic phase was concentrated under vacuum to give a solid. The solid was further purified by trituration with MeOH/H$_2$O (1:1, 15 L) at reflux to give 1 (940 g, 99%) as a solid.

$^1$H NMR (400 MHz, CDCl$_3$) δ 5.40-5:32 (m, 1H), 4.85 (s, 1H), 4.71 (s, 1H), 3.58-3.46 (m, 1H), 2.36-2.16 (m, 2H), 2.08-1.94 (m, 2H), 1.92-1.62 (m, 9H), 1.61-1.39 (m, 6H), 1.29-1.03 (m, 4H), 1.01 (s, 3H), 0.99-0.91 (m, 1H), 0.59 (s, 3H).

Synthesis of 2

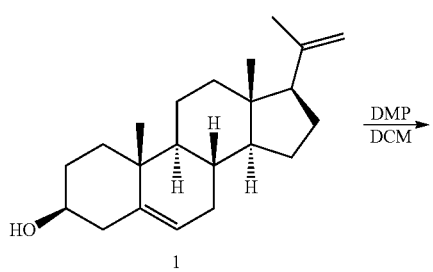

1

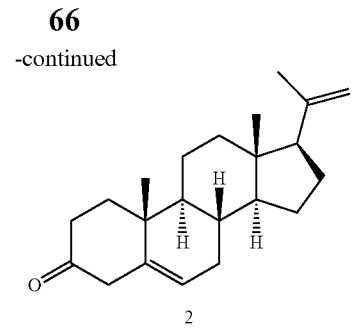

2

To a solution of 1 (800 g, 2.54 mol) in DCM (8 L) was added DMP (2.14 kg, 5.08 mol) in portions at 35° C. The reaction mixture was stirred at 35° C. for 20 mins. The reaction mixture was filtered. The filtered cake was washed with DCM (3×1 L). The combined organic phase was washed with saturated Na$_2$S$_2$O$_3$/saturated NaHCO$_3$ aqueous (3:1, 2×1.5 L), brine (1.5 L), dried over Na$_2$SO$_4$, filtered and concentrated under vacuum to give 2 (794 g, crude) as a solid, which was used for next step directly.

Synthesis of 3

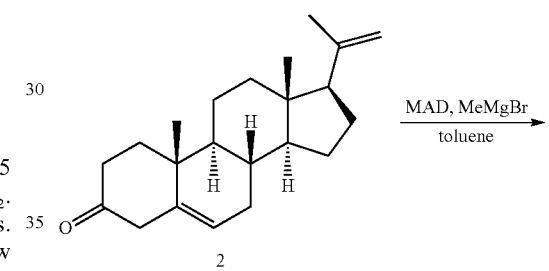

3

To a solution of BHT (1.97 kg, 8.94 mol) in toluene (1 L) was added AlMe$_3$ (2.14 L, 2.0 M in toluene, 4.28 mol) drop-wise below 25° C. under N$_2$ atmosphere. The resulting mixture was stirred at 25° C. for 1 hour. 2 (794 g, 85% percent weight, 2.16 mol) in DCM (3 L) was added at −70° C. The mixture was stirred at −70° C. for 1 hour. MeMgBr (862 mL, 3.0 M in diethyl ether, 2.59 mol) was added at −70° C. The reaction mixture was stirred at −70° C. for 10 mins. The mixture was quenched by saturated critic acid (3 L), extracted with EtOAc (2×2 L). The combined organic phase was washed with brine (2 L), dried over Na$_2$SO$_4$, filtered and concentrated under vacuum to give a residue, which was triturated from MeCN (3 L) at 25° C. to give 3 (340 g, 43%) as a solid.

$^1$H NMR (400 MHz, CDCl$_3$) δ 5.34-5.26 (m, 1H), 4.85 (s, 1H), 4.71 (s, 1H), 2.50-2.35 (m, 1H), 2.07-1.94 (m, 3H), 1.91-1.84 (m, 1H), 1.83-1.63 (m, 8H), 1.58-1.33 (m, 6H), 1.27-1.13 (m, 3H), 1.12 (s, 3H), 1.10-1.05 (m, 1H), 1.02 (s, 3H), 1.00-0.92 (m, 1H), 0.58 (s, 3H).

Synthesis of 4

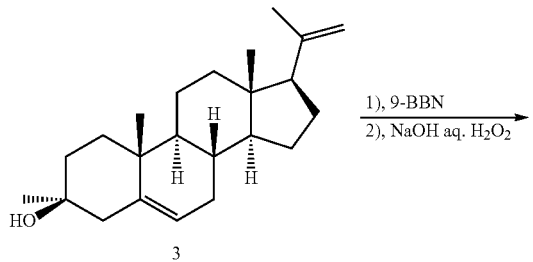

3 (100 g, 304 mmol) was dissolved in 9-BBN (1.21 L, 0.5 M in THF, 608 mmol) at 0° C. under N$_2$. The solution was stirred at 65° C. for 1 hour and re-cooled to 10° C. A lot of solid was precipitated. Ethanol (279 g, 6080 mmol) and NaOH aqueous (304 mL, 5 M, 1520 mmol) were added drop-wise to the mixture below 10° C. to give a clear solution. After that, hydrogen peroxide (343 g, 30% in water, 3040 mmol) was added drop-wise below 10° C. The reaction mixture was stirred at 75° C. for 1 hour. After re-cooling to 20° C., solid was precipitated and collected by filtration. The filter cake was washed with water (3×500 mL), dried under vacuum to give a solid, which was triturated in ethanol (1.5 L) at reflux to give 4 (92 g, 87.6%) as a solid.

$^1$H NMR (400 MHz, CDCl$_3$) δ 5.31-5.29 (m, 1H), 3.65-3.63 (m, 1H), 3.38-3.37 (m, 1H), 2.42 (d, J=12.4, 1H), 2.05-1.92 (m, 3H), 1.88-1.63 (m, 4H), 1.63-1.40 (m, 8H), 1.40-0.90 (m, 16H), 0.70 (s, 3H).

Synthesis of 5

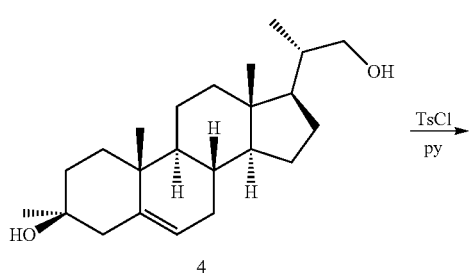

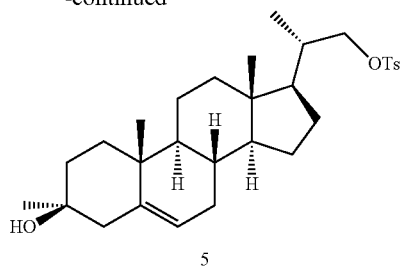

To a solution of 4 (124.5 g, 357 mmol) in chloroform (1 L) and pyridine (700 mL) was added TsCl (204 g, 1071 mmol) at 15° C. The mixture was stirred at 15° C. for 2 hrs. The mixture was concentrated under vacuum to remove most of chloroform. The pyridine mixture was added into water (6 L). A solid was produced and collected by filtration, which was washed with water (6×1 L). The solid was dissolved in DCM (3.5 L), dried over Na$_2$SO$_4$, filtered and concentrated under vacuum to give 5 (163 g, 92%) as a solid.

$^1$H NMR (400 MHz, CDCl$_3$) δ 7:78 (d, J=8.0 Hz, 2H), 7.34 (d, J=8.4 Hz, 2H), 5.29-5.28 (m, 1H), 3.96 (dd, J=3.2, 9.6 Hz, 1H), 3.79 (dd, J=6.4, 9.2 Hz, 1H), 2.45 (s, 3H), 2.41 (d, j=13.6 Hz, 1H), 1.99-1.91 (m, 3H), 1.77-1.39 (m, 11H), 1.26-0.86 (m, 16H), 0.64 (s, 3H).

Synthesis of 61

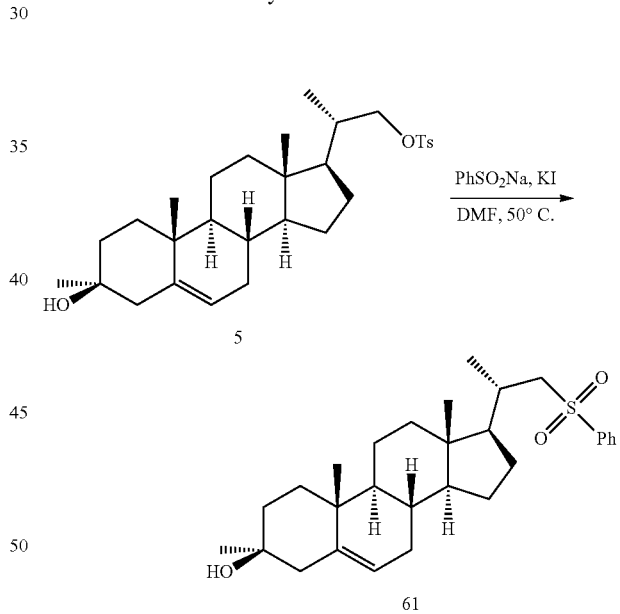

To a solution of 5 (163 g, 325 mmol) in DMF (1.7 L) was added KI (258 g, 1560 mmol) at 15° C. The mixture was stirred at 60° C. for 2 hours. After that, sodium benzenesulfinate (195 g, 975 mmol) was added and the mixture was stirred at 60° C. for 2 hours. The reaction mixture was cooled to 25° C. and combined with another batch from 83 g of 5. The combined mixture was poured into water (20 L) and some solid was produced. The mixture was filtered and the filter cake was washed with water (3×2 L). The resulting filter cake dissolved in DCM (5 L), washed with water (2×1 L), brine (2×1 L), dried over Na$_2$SO$_4$, filtered and concentrated in vacuum to give a crude product as a solid, which was re-crystallized in toluene (2.5 L) to give 61 (150 g, 65%)

as a solid. The re-crystallization filtrate was concentrated under vacuum to give a crude 61 (30 g) as a solid.

$^1$H NMR (400 MHz, CDCl$_3$) δ 7.91 (d, J=7.2 Hz, 2H), 7.69-7.61 (m, 1H), 7.60-7.50 (m, 2H), 5.28-5.27 (m, 1H), 3.14 (d, J=14.0 Hz, 1H), 2.85 (dd, J=9.6, 14.0 Hz, 1H), 2.41 (d, J=12.8 Hz, 1H), 2.17-2.03 (m, 1H), 2.02-1.87 (m, 3H), 1.81-1.65 (m, 3H), 1.60-1.32 (m, 8H), 1.25-0.85 (m, 16H), 0.65 (s, 3H).

LCMS Rt=2.057 min in 3.0 min chromatography, 30-90 AB, purity 100%, MS ESI calcd. for C$_{29}$H$_{41}$O$_2$S [M+H-H$_2$O]$^+$ 453, found 453.

Example 2: Synthesis of Epoxide

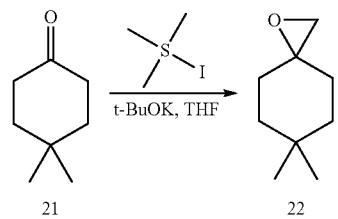

To a suspension of t-BuOK (3.53 g, 31.6 mmol) in THF (30 mL) was added Me$_3$SI (4.18 g, 20.5 mmol) under N$_2$ at 15° C. The suspension was stirred at 15° C. for 30 min. To the mixture was added a solution of 21 (2 g, 15.8 mmol) in 10 ml of THF dropwise at 15° C. The mixture was stirred at 15° C. for 16 hrs. The mixture was quenched with sat.NH$_4$C$_1$ (100 mL) and extracted with EtOAc (3×150 mL). The combined organic phase was dried over Na$_2$SO$_4$, filtered, and concentrated in vacuum to give 22 (1.8 g, 81%) as a liquid.

$^1$H NMR (400 MHz, CDCl$_3$) δ 2.58 (s, 2H), 1.90-1.80 (m, 1H), 1.70-1.55 (m, 2H), 1.54-1.45 (m, 3H), 1.40-1.30 (m, 2H), 1.00-0.90 (m, 6H).

Example 3: Synthesis of 71

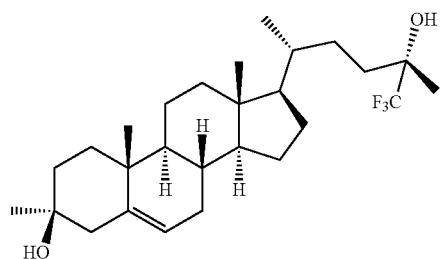

Overview:

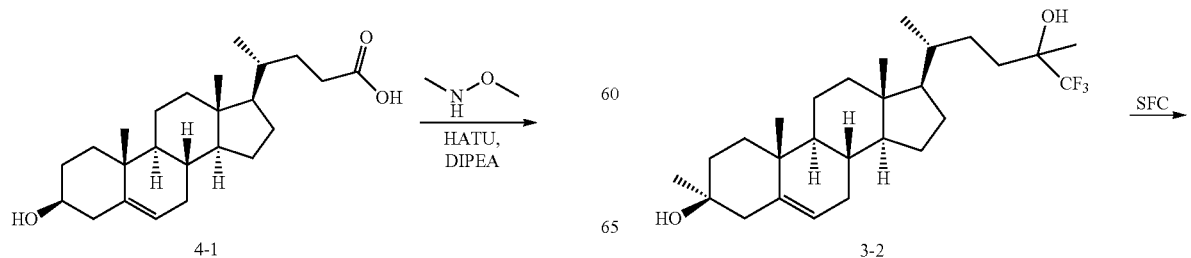

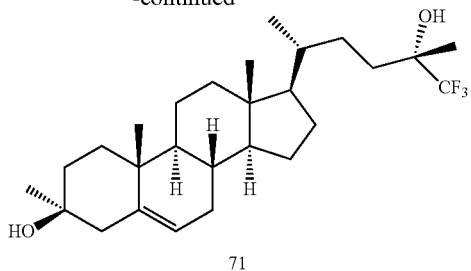

71

Synthesis of Compound 4-2. To a solution of 4-1 (38 g, 101.5 mmol) in THF (400 mL) at room temperature was added HATU (46.3 g, 121.8 mmol), DIPEA (45.9 g, 355.2 mmol). The mixture was stirred for 1 h, and N,O-dimethylhydroxylamine hydrochloride (19.8 g, 203 mmol) was added. The mixture was stirred at room temperature for another 6 h. The reaction mixture was concentrated, poured into water, extracted with EtOAc, washed with water, dried over $Na_2SO_4$, and concentrated to give crude product. The crude product was purified by column chromatography on silica gel (eluent: PE:EA=3:1) to afford the desired product 4-2 (24 g, 57%) as a solid.

$^1$H NMR: (300 MHz, CDCl3) δ: ppm 5.25 (d, J=5.2 Hz, 1H), 3.59 (s, 3H), 3.46-3.37 (m, 1H), 3.07 (s, 3H), 2.70 (s, 1H), 2.40-2.09 (m, 4H), 1.92-1.63 (m, 6H), 1.44-1.33 (m, 6H), 1.29-1.15 (m, 3H), 1.11-0.93 (m, 5H), 0.90 (s, 3H), 0.85 (d, J=6.4 Hz, 3H), 0.82-0.78 (m, 1H), 0.58 (s, 3H).

Synthesis of Compound 4-3. To a solution of compound 4-2 (14 g, 33.52 mmol, 1.0 eq) in dry $CH_2Cl_2$ (600 mL) was added Dess-Martin (28 g, 67.04 mmol, 2.0 eq) in portions at 0° C. Then the reaction mixture was stirred at room temperature for 6.5 h. TLC (PE:EA=3:1) showed the starting material was consumed completely. The mixture was quenched with saturated aqueous $NaHCO_3/Na_2S_2O_3$=1:3 (800 mL). The organic phase was washed with brine (500 mL) and dried over $Na_2SO_4$, and the solvent was evaporated to afford crude product 4-3 (14.0 g, 100%).

Synthesis of Compound 4-4. To a solution of MAD (101 mmol, 3.0 eq) in toluene, freshly prepared by addition of a solution of $Me_3Al$ (50.5 mL, 101.00 mmol, 2 M in hexane) to a stirred solution of 2,6-di-terf-butyl-4-methylphenol (44.4 g, 202 mmol) in toluene (200 mL) followed by stirring for 1 h at room temperature, was added dropwise a solution of 4-3 (14.0 g, 33.7 mmol, 1.0 eq) in toluene (10 mL) at −78° C. under nitrogen. Then the reaction mixture was stirred for 30 min, a solution of MeMgBr (33.7 mL, 101 mmol, 3.0 eq, 3 M in ether) was added dropwise at −78° C. The reaction mixture was warmed to 25° C. and stirred at this temperature for 12 h. TLC (PE:EA=3:1) showed that the starting material was consumed completely. The mixture was poured into aqueous saturated $NH_4Cl$ solution (200 mL) and extracted with EtOAc (200 mL×2). The combined organic phases were dried over $Na_2SO_4$, and the solvent was evaporated to afford crude product. The crude product was purified by column chromatography on silica gel (eluent: PE:EA=3:1) to give the pure target (7.5 g, 52%) as a powder.

$^1$H NMR: (400 MHz, CDCl3) δ 5.30 (d, J=5.2 Hz, 1H), 3.69 (s, 3H), 3.17 (s, 3H), 2.50-2.30 (m, 3H), 2.05-1.70 (m, 7H), 1.52-1.30 (m, 9H), 1.20-0.90 (m, 15H), 0.68 (s, 3H).

Synthesis of Compound 3-1. To a solution of compound 4-4 (7.5 g, 17.4 mmol, 1.0 eq) in THF (150 mL) was added dropwise a solution of MeMgBr (29 mL, 87 mmol, 5.0 eq, 3 M in THF) at room temperature during a period of 30 min under nitrogen. Then the reaction mixture was stirred at room temperature for 12 h. TLC (PE:EA=1:1) showed that the starting material was consumed completely. The mixture was poured into aqueous saturated $NH_4Cl$ solution (200 mL) and extracted with EtOAc (150 mL×2). The combined organic phases were dried over $Na_2SO_4$, and the solvent was evaporated to afford crude product. The crude product was purified by column chromatography on silica gel (eluent: PE:EA=4:1) to give the product 3-1 (5.2 g, 77%) as a powder.

$^1$H NMR: (400 MHz, CDCl3) δ 5.30 (d, J=5.2 Hz, 1H), 2.50-2.30 (m, 3H), 2.14 (s, 3H) 2.03-1.93 (m, 3H), 1.87-1.68 (m, 4H), 1.60-1.18 (m, 12H), 1.12 (s, 3H), 1.11-1.03 (m, 1H), 1.01 (s, 3H), 1.00-0.94 (m, 1H), 0.91 (d, J=6.4 Hz, 3H), 0.68 (s, 3H).

Synthesis of 3-2. To a suspension of 3-1 (400 mg, 1.035 mmol) and CsF (76 mg) in toluene/THF (20 mL, 8/1) was added TMSCFs (1.53 mL, 10.35 mmol) and the mixture was stirred for 20° C. at room temperature under nitrogen. TLC (petroleum ether:ethyl acetate=3/1) showed the starting material was consumed completely. A solution of TBAF (6.8 mL, 1 M in THF) was added and the mixture was stirred for 4 h at room temperature. The mixture was diluted with MTBE (200 mL), washed with aq. saturated $NaHCO_3$ solution (30 mL×3) and concentrated in vacuum. The residue was purified by column chromatography on silica gel (eluent: petroleum ether:ethyl acetate=20:1) to afford 3-2 (220 mg, 46%) as a solid.

$^1$H NMR: (400 MHz, CDCl3) δ 5.31 (d, J=2.0 Hz, 1H), 2.44-2.41 (m, 1H), 2.04-1.96 (m, 3H), 1.81-1.67 (m, 5H), 1.65-1.39 (m, 11H), 1.34-1.32 (m, 3H), 1.31-1.25 (m, 1H), 1.21-1.10 (m, 3H), 1.12-0.98 (m, 4H), 0.96 (s, 0.5H), 0.98-0.90 (m, 4H), 0.68 (s, 3H.)

Synthesis of 71. Compound 3-2 (1.2 g, 2.63 mmol) was split by SFC to get Product 71 (400 mg).

$^1$H NMR (71): (400 MHz, CDCl$_3$) δ 5.32 (d, J=4.0 Hz, 1H), 2.50-2.40 (m, 1H), 2.08-1.95 (m, 3H), 1.90-0.90 (m, 35H), 0.70 (s, 3H).

Example 4: Synthesis of 1201

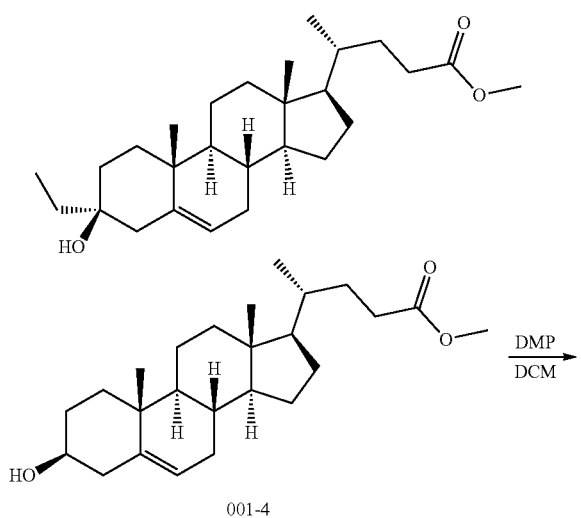

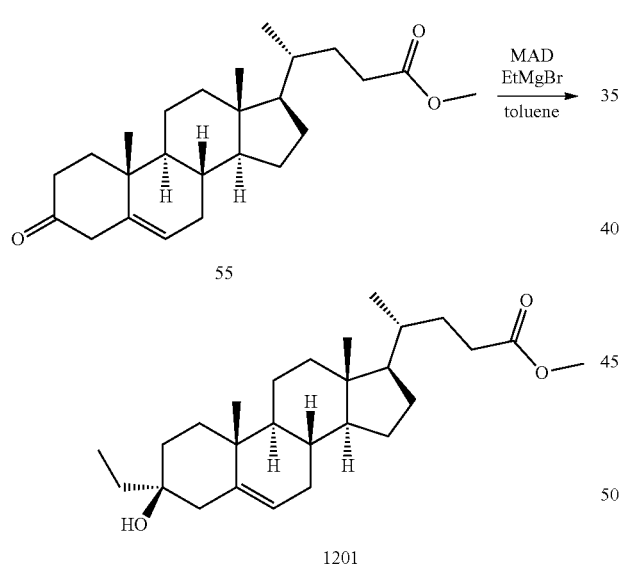

To a solution of 001-4 (50 g, 128 mmol) in DCM (800 mL) was added DMP (108 g, 256 mmol) at 30° C. The reaction mixture was stirred at 30° C. for 10 minutes. And H₂O (2.3 g, 128 mmol) was added dropwise. The reaction mixture was quenched with Saturated NaHCO₃ aqueous (500 mL) until pH of the aqueous layer became about 9. The mixture was filtered. The DCM layer was separated and the aqueous phase was extracted with DCM (100 mL). The combined organic phase was washed with saturated Na₂S₂O₃ aqueous (600 mL), brine (500 mL), dried over Na₂SO₄, filtered and concentrated to give 55 (108 g, crude) as an oil. The reaction was conducted in parallel for 2 times.

¹H NMR (400 MHz, CDCl₃) δ 5.30-5.26 (m, 1H), 3.67 (s, 3H), 3.30-3.22 (m, 1H), 2.85-2.79 (m, 1H), 2.50-2.15 (m, 4H), 2.08-1.96 (m, 3H), 1.90-1.71 (m, 2H), 1.56-1.45 (m, 6H), 144-1.19 (m, 3H), 1.17 (s, 3H), 1.15-0.97 (m, 5H), 0.96-0.88 (m, 3H), 0.70 (s, 3H).

To a solution of BHT (367 g, 1.67 mmol) in toluene (1000 mL) under nitrogen at 0° C. was added trimethylaluminum (2 M in toluene, 418 mL, 837 mmol) dropwise. The mixture was stirred at 0° C. for 30 min and used directly as a solution of MAD (0.59 M in toluene) without further purification. To the solution of MAD (0.59 M in toluene, 1410 mL, 837 mmol) under nitrogen at −78° C. was added a solution of 55 (108 g, 279 mmol) in toluene (500 mL) dropwise. The mixture was stirred at −78° C. for 30 min. EtMgBr (3 M in diethyl ether, 278 mL, 837 mmol, 3M in ether) was added dropwise. The resulting mixture was stirred at −78° C. for 1 hr. The reaction mixture was poured to ice-cooled aqueous citric acid (1000 mL), extracted with EtOAc (2×500 mL). The combined organic layer was washed with brine (500 mL), dried over anhydrous sodium sulfate, filtered and concentrated. The residue was purified by column chromatography on silica gel (0-20% of EtOAc in PE) to give 1201 (95 g, impure) as an oil. The reaction was conducted in parallel for 2 times.

¹H (400 MHz, CDCl₃) δ 5.30-5.26 (m, 1H), 3.65 (s, 3H), 2.48-2.18 (m, 4H), 2.08-1.91 (m, 2H), 1.90-1.76 (m, 4H), 1.75-1.61 (m, 4H), 1.60-1.48 (m, 5H), 1.47-1.22 (m, 5H), 1.17 (s, 1H), 1.16-1.02 (m, 3H), 1.01-0.96 (m, 2H), 0.95-0.90 (m, 1H), 0.89-0.82 (m, 4H), 0.81-0.76 (m, 2H), 0.67 (s, 3H).

Example 5: Synthesis of U6477, U6478

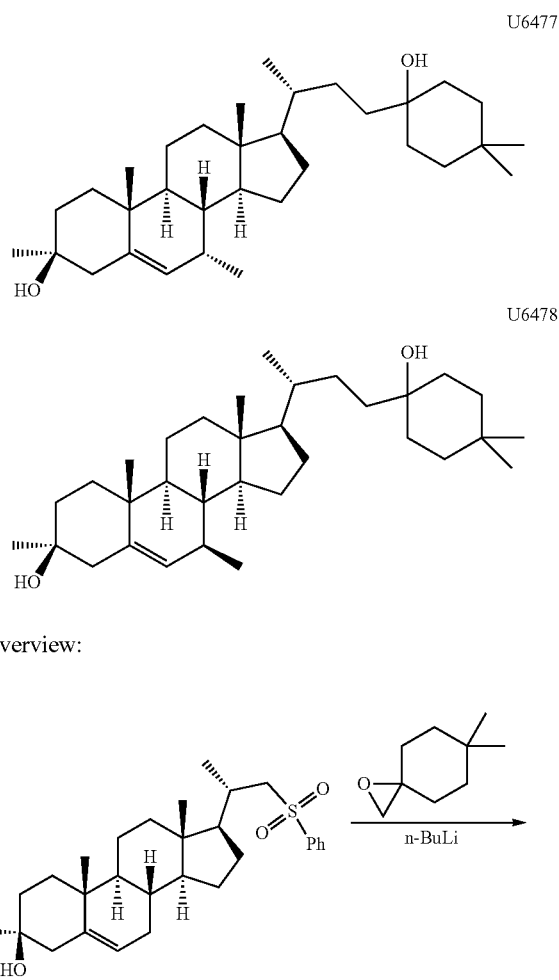

Overview:

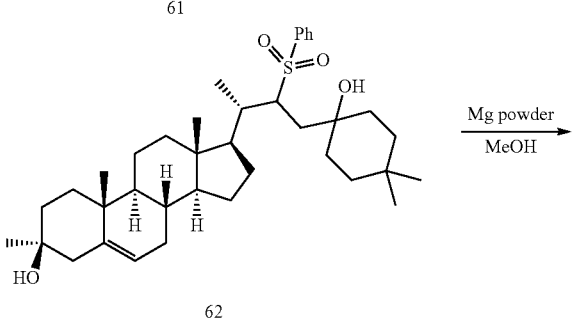

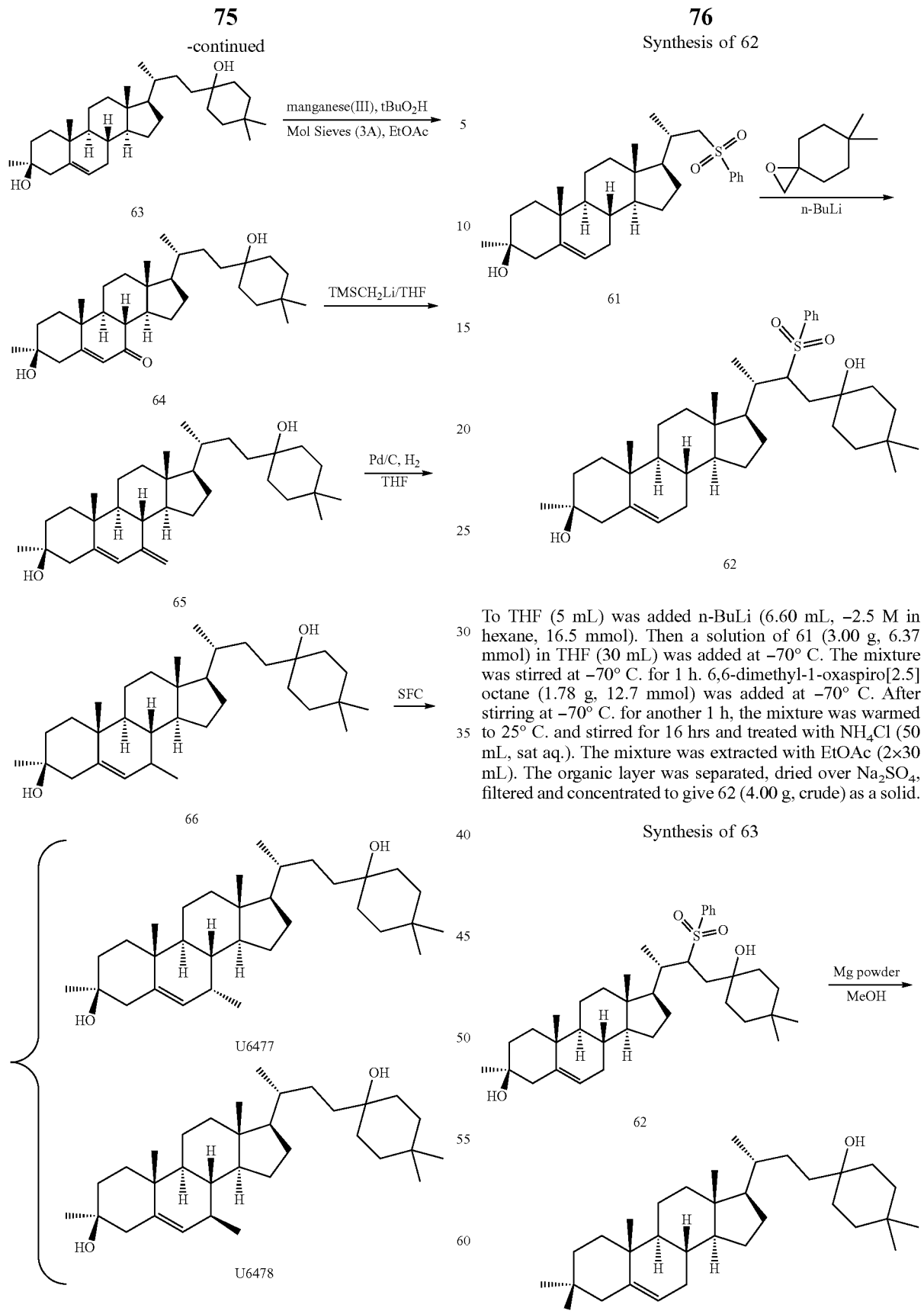

Synthesis of 62

To THF (5 mL) was added n-BuLi (6.60 mL, ~2.5 M in hexane, 16.5 mmol). Then a solution of 61 (3.00 g, 6.37 mmol) in THF (30 mL) was added at −70° C. The mixture was stirred at −70° C. for 1 h. 6,6-dimethyl-1-oxaspiro[2.5]octane (1.78 g, 12.7 mmol) was added at −70° C. After stirring at −70° C. for another 1 h, the mixture was warmed to 25° C. and stirred for 16 hrs and treated with NH₄Cl (50 mL, sat aq.). The mixture was extracted with EtOAc (2×30 mL). The organic layer was separated, dried over Na₂SO₄, filtered and concentrated to give 62 (4.00 g, crude) as a solid.

Synthesis of 63

The experimental of intermediate 61 can be found Example 1 herein. The synthesis of the epoxide can be found in Example 2 herein.

To a solution of 62 (4.00 g, 6.54 mmol) in MeOH (200 mL) was added NiCl₂ (61.5 mg, 0.654 mmol) and heated at 60° C. Mg powder (6.34 g, 261 mmol) was added in portions at 60° C. The mixture was stirred at 60° C. for 1 h. The mixture was quenched with HCl (200 mL, 2 M) until the reaction became clear and extracted with EtOAc (3×200 mL). The combined organic phase was dried over Na₂SO₄, filtered, concentrated and purified by flash column (0-15% of EtOAc in PE) to give 63 (1.20 g, 39%) as a solid.

¹H NMR 63 (400 MHz, CDCl₃) δ 5.32-5.28 (m, 1H), 2.43-2.38 (m, 1H), 2.05-1.56 (m, 9H), 1.50-1.41 (m, 8H), 1.41-1.26 (m, 5H), 1.26-0.94 (m, 15H), 0.94-0.83 (m, 12H), 0.68 (s, 3H).

Synthesis of 64

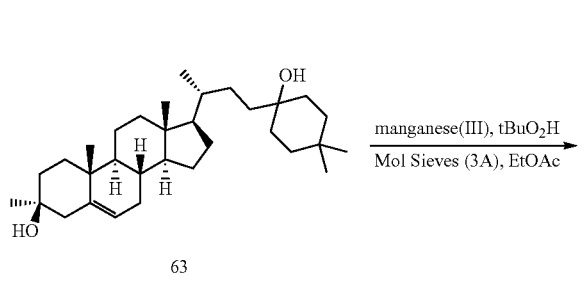

A solution of 63 (2.00 g, 4.24 mmol) in ethyl acetate (120 mL) was added molecular sieves (200 mg) and t-butylhydroperoxide (4.23 mL, 25.4 mmol, 6 M in decane). The suspension was stirred under nitrogen atmosphere for 30 min at 25° C. and manganese (III) acetate dihydrate (340 mg, 1.27 mmol) was then added in one portion. The reaction mixture was stirred at 25° C. for 48 hrs. The solids were filtered off and the filtrate was washed with Na₂SO₃ (200 mL), brine (200 mL) and dried over Na₂SO₄, filtered and concentrated in vacuum. The residue was purified by silica gel chromatograph (0-15% of EtOAc in DCM) to afford 64 (1.10 g, 54%) as a solid.

¹H NMR 64 (400 MHz, CDCl₃) δ 5.66 (s, 1H), 2.61-2.55 (m, 1H), 2.45-2.34 (m, 1H), 2.28-2.19 (m, 2H), 2.08-1.78 (m, 5H), 1.68-1.50 (m, 9H), 1.50-1.08 (m, 21H), 0.98-0.83 (m, 9H), 0.68 (s, 3H).

Synthesis of 65

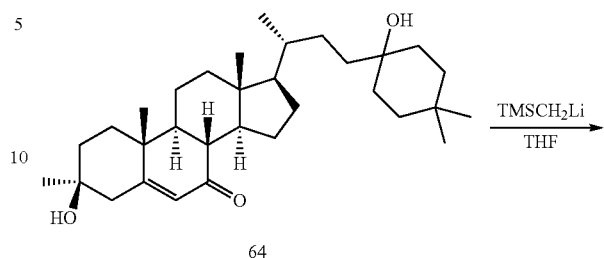

To a solution of TMSCH₂Li (0.56 M in hexane, 9.19 mL, 5.15 mmol) in anhydrous THF (25 mL) under nitrogen at −40° C. was added a solution of 64 (500 mg, 1.03 mmol) dropwise. The mixture was stirred at −40° C. for 4 hrs and warmed to 20° C. gradually and stirred at 20° C. for additional 16 hrs. The reaction mixture was quenched with saturated NH₄Cl (20 mL), acidified with 10% HCl (8 mL) and stirred for 2 hrs. The mixture was combined with another batch (prepared from 100 mg of 64), extracted with EtOAc (3×20 mL). The combined organic layer was dried over anhydrous sodium sulfate, filtered and concentrated. The residue was purified by column chromatography on silica gel (0~20% of EtOAc in PE) to give 65 (220 mg, 44%) as a solid.

¹H NMR 65 (400 MHz, CDCl₃) δ 5.79 (s, 1H), 4.93 (s, 1H), 4.74 (s, 1H), 2.51-2.42 (m, 1H), 2.19-2.00 (m, 4H), 1.97-1.85 (m, 1H), 1.82-1.70 (m, 2H), 1.63-1.58 (m, 2H), 1.52-1.37 (m, 12H), 1.36-1.14 (m, 11H), 1.13 (s, 3H), 1.09 (s, 3H), 0.96 (d, J=6.8 Hz, 3H), 0.93 (s, 3H), 0.87 (s, 3H), 0.71 (s, 3H).

Synthesis of 66

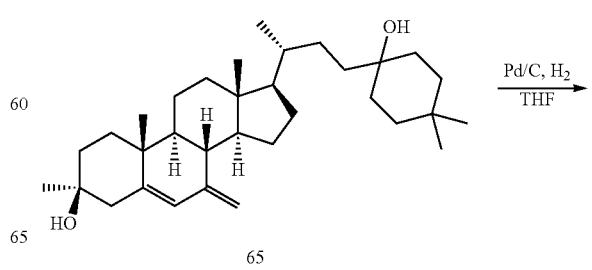

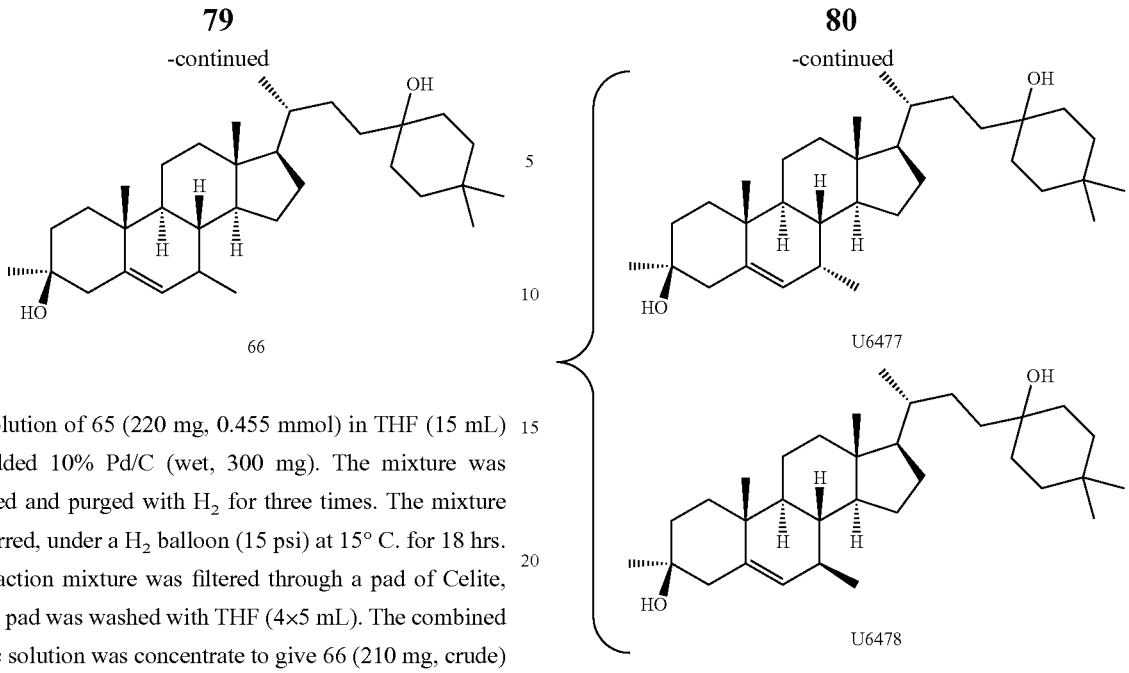

To a solution of 65 (220 mg, 0.455 mmol) in THF (15 mL) was added 10% Pd/C (wet, 300 mg). The mixture was degassed and purged with $H_2$ for three times. The mixture was stirred, under a $H_2$ balloon (15 psi) at 15° C. for 18 hrs. The reaction mixture was filtered through a pad of Celite, and the pad was washed with THF (4×5 mL). The combined organic solution was concentrate to give 66 (210 mg, crude) as a solid.

LCMS 66 Rt=5.692 min in 7.0 min chromatography, 30-90AB_7MIN_220&254_E, (Column: Xtimate C18 2.1?30 mm, 3 um; Mobile Phase: A: water (4 L)+TFA (1.5 mL) B: acetonitrile (4 L)+TFA (0.75 mL); Gradient: from 30% to 90% of B in 6 min and hold 90% for 0.5 min, then 30% of B for 0.5 min; Flow Rate: 0.8 mL/min; wavelength: UV 220 nm, 254 nm; Oven Temp: 50° C.; MS ionization: ESI; Detector: PDA, ELSD), purity 100%, MS ESI calcd. for $C_{33}H_{53}$ $[M+H-2H_2O]^+$ 449, found 449.

SFC 66 Peak 1: Rt=6.184 min and Peak 2 Rt=6.969 min in 10 min chromatography, AD_3_EtOH_DEA_5_40_25ML ("Column: Chiralpak AD-3 150×4.6 mm I.D., 3 um Mobile phase: A: $CO_2$ B: ethanol (0.05% DEA) Gradient: from 5% to 40% of B in 5 min and hold 40% for 2.5 min, then 5% of B for 2.5 min Flow rate: 2.5 mL/min Column temp: 35° C.").

Synthesis of U6477, U6478

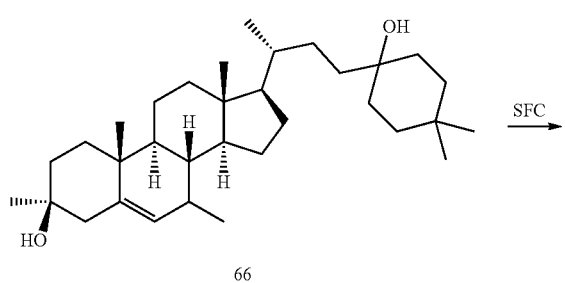

66 (210 mg, 0.433 mmol) was purified by SFC (Column: AD (250 mm*30 mm, 5 um); Condition: 0.1% $NH_3H_2O$ EtOH; Begin B: 40%; End B: 40%; Gradient Time (min): 100% B Hold Time (min); Flow Rate (ml/min): 60 ML/MIN; Injections: 200) to afford U6477 (peak 1, 56 mg, 27%) as solid and U6478 (peak 2, 30 mg, 14%) as solid. The stereochemistry at $C_7$ was assigned based on the featured HNMR of compound 82 and compound U6429 as a). 7-alpha-H isomer with H-6 as singlet in high field; b) 7-beta-H isomer with H-6 as doublet in low field.

U6477

$^1$H NMR (400 MHz, $CDCl_3$) δ 5.79 (s, 1H), 2.50-2.42 (m, 1H), 2.05-1.65 (m, 7H), 1.55-1.35 (m, 13H), 1.34-1.05 (m, 16H), 1.03-0.85 (m, 7H), 0.84-0.75 (m, 7H), 0.70-0.60 (m, 4H).

LCMS Rt=1.490 min in 2.0 min chromatography, 30-90AB_2MIN_E, purity 98.839%, MS ESI calcd. for $C_{33}H_{53}$ $[M+H-2H_2O]^+$ 449, found 449.

SFC Rt=6.292 min in 10 min chromatography, AD_3_EtOH_DEA_5_40_25ML, 100% de.

U6478

$^1$H NMR (400 MHz, $CDCl_3$) δ 5.03 (s, 1H), 2.50-2.42 (m, 1H), 2.05-1.95 (m, 2H), 1.94-1.60 (m, 6H), 1.55-1.25 (m, 15H), 1.24-1.05 (m, 12H), 1.03-0.85 (m, 16H), 0.68 (s, 3H).

LCMS Rt=1.568 min in 2.0 min chromatography, 30-90AB_2MIN_E, purity 100%, MS ESI calcd. for $C_{33}H_{53}$ $[M+H-2H_2O]^+$ 449, found 44?.

SFC Rt=7.066 min in 10 min chromatography, AD_3_EtOH__DEA_5_40_25ML, 95% de.

Example 6: Synthesis of U6472. U6473
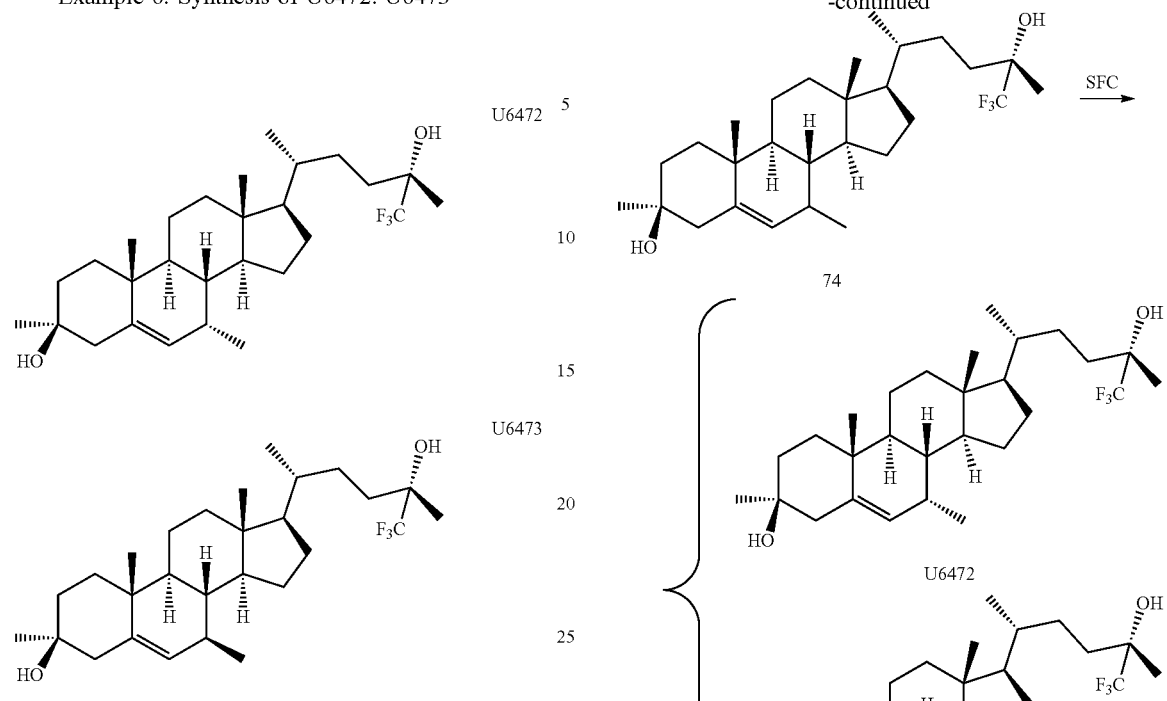
Overview:
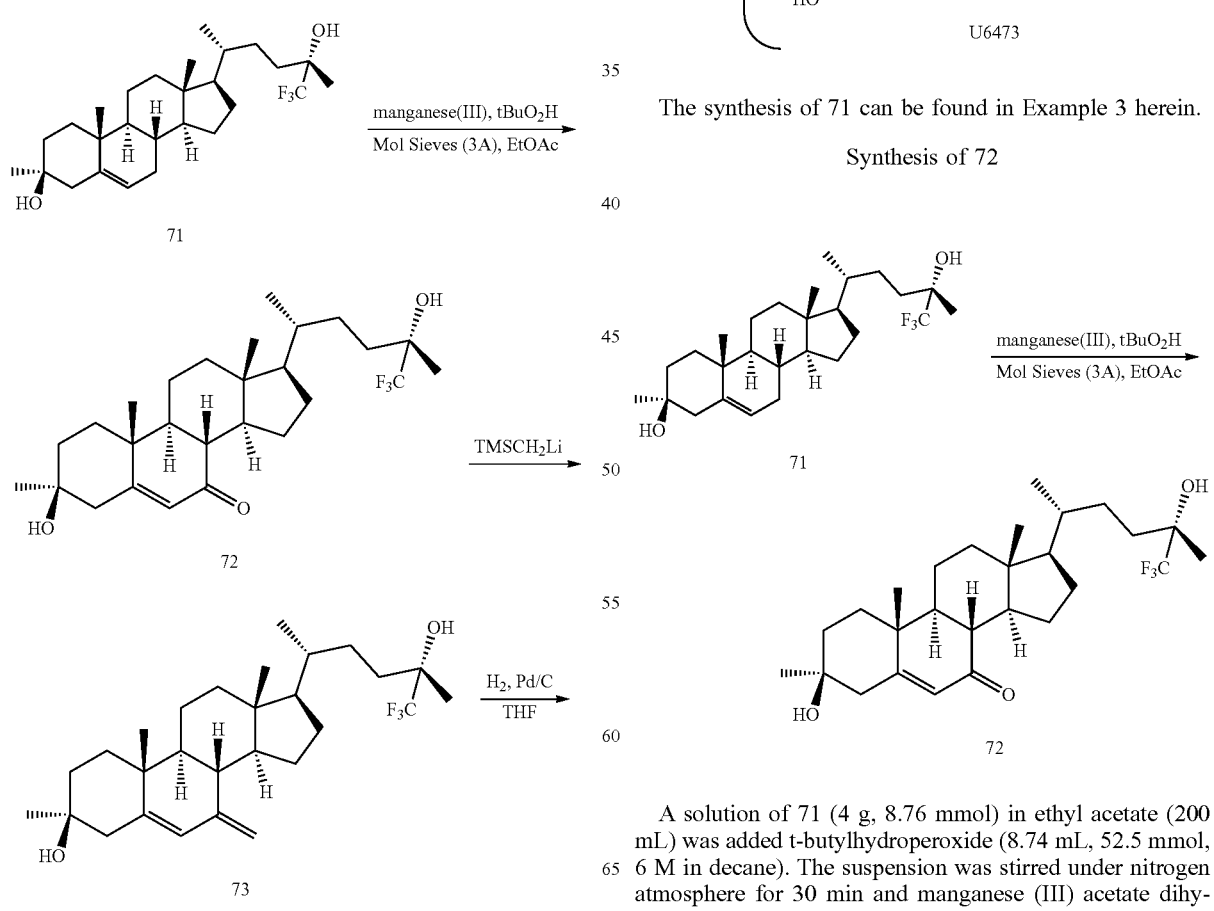
The synthesis of 71 can be found in Example 3 herein.
Synthesis of 72
A solution of 71 (4 g, 8.76 mmol) in ethyl acetate (200 mL) was added t-butylhydroperoxide (8.74 mL, 52.5 mmol, 6 M in decane). The suspension was stirred under nitrogen atmosphere for 30 min and manganese (III) acetate dihydrate (702 mg, 2.62 mmol) was then added in one portion.

After stirring at 30° C. for 48 hrs, the mixture was quenched with Na₂SO₃ (200 mL) and extracted with THF (2×100 mL). The combined organic was washed with Na₂SO₃ (200 mL), brine (200 mL), dried over Na₂SO₄, filtered and concentrated to give a residue, which was triturated with MeCN (60 mL) to give pure 72 (800 mg) as a solid.

¹H NMR 72 (400 MHz, CDCl₃) δ 5.69-5.64 (m, 1H), 2.64-2.53 (m, 1H), 2.51-2.36 (m, 1H), 2.29-2.18 (m, 2H), 2.07-1.99 (m, 1H), 1.95-1.64. (m, 6H), 1.63-1.58 (m, 3H), 1.54-1.47 (m, 3H), 1.45-1.25 (m, 8H), 1.20 (s, 3H), 1.18-1.02 (m, 6H), 0.99-0.90 (m, 3H), 0.69 (s, 3H).

Synthesis of 73

To a solution of TMSCH₂Li (18.3 mL, 8.45 mmol, 0.46M in hexane) in THF (20 mL) was added dropwise a solution of 72 (800 mg, 1.69 mmol) in THF (50 mL) at −40° C. After addition, the resulting mixture was allowed to warm to 30° C. and stirred for 16 hrs. The mixture was quenched with HCl (2M, 100 mL) and extracted with EtOAc (2×80 mL). The combined organic phase was washed with sat.NaHCO₃ (100 mL), dried over Na₂SO₄, filtered, concentrated and purified by combi-flash (0-20% of EtOAc in PE) to give 73 (350 mg, 44%) as a solid.

¹H NMR 73 (400 MHz, CDCl₃) δ 5.81-5.76 (m, 1H), 4.95-4.89 (m, 1H), 4.77-4.70 (m, 1H), 2.50-2.41 (m, 1H), 2.18-2.06 (m, 2H), 2.04-2.00 (m, 1H), 1.94-1.68 (m, 5H), 1.55-1.47 (m, 4H), 1.44-1.37 (m, 4H), 1.32 (s, 3H), 1.30-1.11 (m, 10H), 1.09 (s, 3H), 0.99-0.94 (m, 3H), 0.89-0.81 (m, 1H), 0.71 (s, 3H).

Synthesis of 74

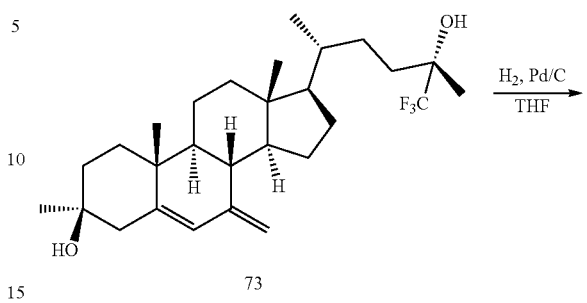

To a solution of 73 (350 mg, 0.746 mmol) in THF (30 mL)) was added Pd/C (350 mg, wet). The mixture was hydrogenated at 15 Psi, 30° C. for 16 hrs. The mixture was filtered. The filter cake was washed with THF (2×10 mL). The combined filtration was concentrated and purified by combi-flash (0-20% of EtOAc in PE) to give pure 74 (200 mg, 57%) as a solid. SFC 74-Peak 1: Rt=3.343 min and Peak 2 Rt=4.297 min in 10 min chromatography, AD_3_EtOH_DEA_5_40_25ML ("Column: Chiralpak AD-3 150×4.6 mm I.D., 3 um Mobile phase: A: CO₂ B: methanol (0.05% DEA) Gradient: from 5% to 40% of B in 5 min and hold 40% for 2.5 min, then 5% of B for 2.5 min Flow rate: 2.5 mL/min Column temp.: 35° C."

Synthesis of U6472, U6473

-continued

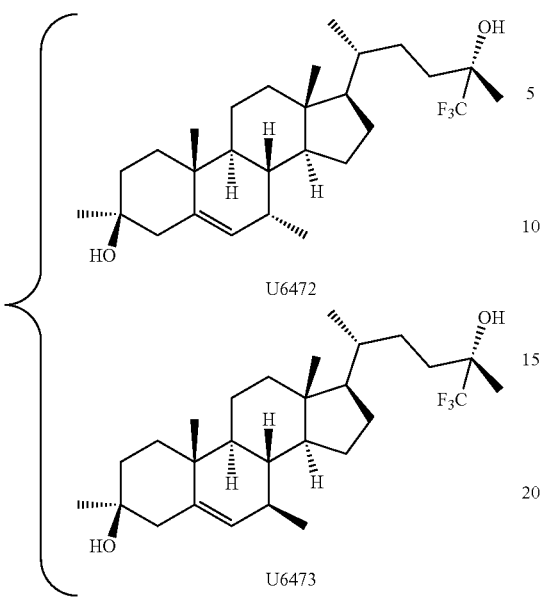

200 mg racemic sample was separated by SFC (column: AD (250 mm*30 mm, 5 um), gradient: 35-35% B (A=0.05% NH₃/H₂O, B=MeOH), flow rate: 50 mL/min) to give U6472 (57 mg, 29% yield, Peak 1) and U6473 (43 mg, 22% yield, Peak 2) as a solid. The stereochemistry at $C_7$ was assigned based on the featured HNMR of compound 82 and compound U6429 as a). 7-alpha-H isomer with H-6 as singlet in high field; b) 7-beta-H isomer with H-6 as doublet in low field.

U6472

¹H NMR (400 MHz, CDCl₃) δ 5.35-5.30 (m, 1H), 2.49-2.39 (m, 1H), 2.06-1.90 (m, 3H), 1.87-1.66 (m, 5H), 1.56-1.40 (m, 8H), 1.35-1.24 (m, 5H), 1.18-1.06 (m, 1 OH), 1.01'(s, 3H), 0.97-0.91 (m, 3H), 0.86-0.79 (m, 3H), 0.68 (s, 3H).

LCMS Rt=1.240 min in 2.0 min chromatography, 30-90AB_E, purity 100%, MS ESI calcd. for $C_{28}H_{44}F_3O$ $[M+H-H_2O]^+$ 453, found 453.

SFC Rt=3.357 min in 10 min chromatography, AD_3_EtOH_DEA_5_40_25 ML, 99.72% de.

U6473

¹H NMR (400 MHz, CDCl₃) δ 5.06-5.00 (m, 1H), 2.42-2.34 (m, 1H), 2.03-1.95 (m, 2H), 1.87-1.65 (m, 7H), 1.56-1.35 (m, 6H), 1.34-1.26 (m, 5H), 1.22-1.03 (m, 10H), 1.00-0.91 (m, 10H), 0.69 (s, 3H).

LCMS Rt=1.246 min in 2.0 min chromatography, 30-90AB_E, purity 100%, MS ESI calcd. for $C_{28}H_{44}F_3O$ $[M+H-H_2O]^+$ 453, found 453.

SFC Rt=4.300 min in 10 min chromatography, AD_3_EtOH_DEA_5_40_25 ML, 99.52% de.

Example 7: Synthesis of U6450

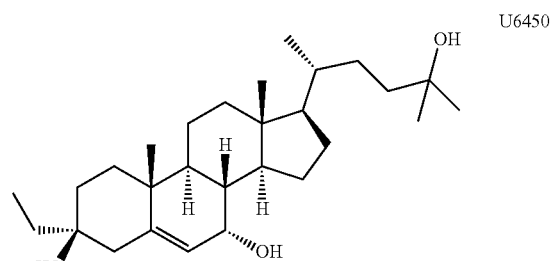

The synthesis of U6461 can be found in Example 11 herein.

Synthesis of 82

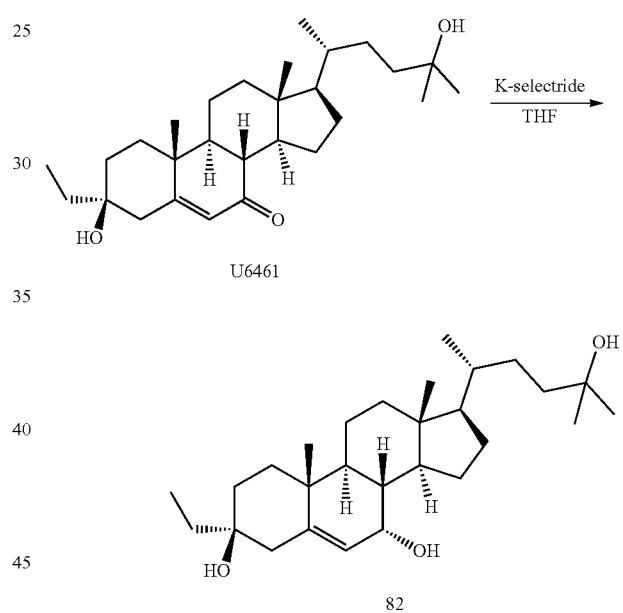

To a solution of U6461 (100 mg, 0.232 mmol) in THF (5 mL) was added dropwise K-selectride (1.16 mL, 1.16 mmoll 1M in THF) at −70° C. After addition, the mixture was warmed to 0° C. and stirred at this temperature for 1 h. The mixture was quenched with sat.NH₄Cl (20 mL) and extracted with EtOAc (3×10 mL). The combined organic phase was washed with brine (2×20 mL), dried over Na₂SO₄, filtered and concentrated and purified by combi-flash (0-60% of EtOAc in PE) to give 60 mg impure 82 as a solid, which was used directly for the next step. The stereochemistry at $C_7$ was assigned according to the literature (Synthesis, 1987, 1002) compared with compound U6429 based on a). 7-alpha-H isomer with H-6 as singlet in high field; b) 7-beta-H isomer with H-6 as doublet in low field.

Synthesis of U6450
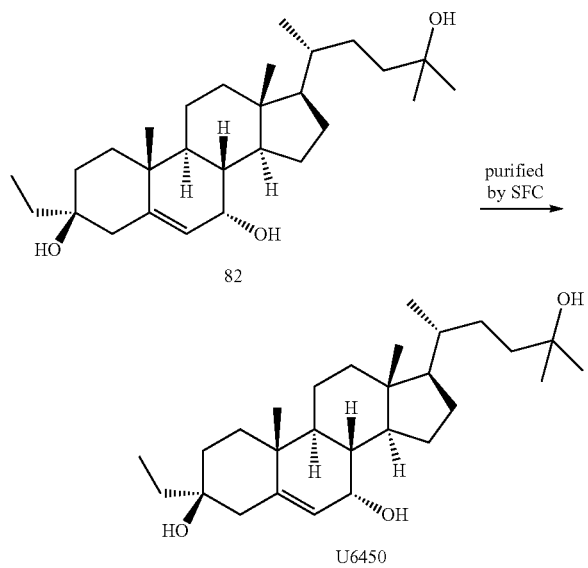
140 mg of impure 82 was separated by SFC (column: AD (250 mm*30 mm, 5 um), gradient: 50-50% B (A=0.05% NH$_3$/H$_2$O, B=MeOH), flow rate: 60 mL/min) to give 82 (70 mg, 50%) as a solid.
$^1$H NMR U6450 (400 MHz, CDCl$_3$) δ 5.58-5.52 (m, 1H), 3.87-3.79 (m, 1H), 2.46-2.38 (m, 1H), 2.14-1.84 (m, 3H), 1.80-1.57 (m, 4H), 1.55-1.38 (m, 9H), 1.37-1.22 (m, 4H), 1.21-1.06 (m, 12H), 1.04-0.97 (m, 4H), 0.96-0.91 (m, 3H), 0.88-0.82 (m, 3H), 0.68 (s, 3H).
LCMS U6450 Rt=1.108 min in 2.0 min chromatography, 30-90AB_E, purity 100%, MS ESI calcd. for C$_{28}$H$_{45}$O [M+H−2H$_2$O]$^+$ 397, found 397.
Example 8: Synthesis of U6437, U6438
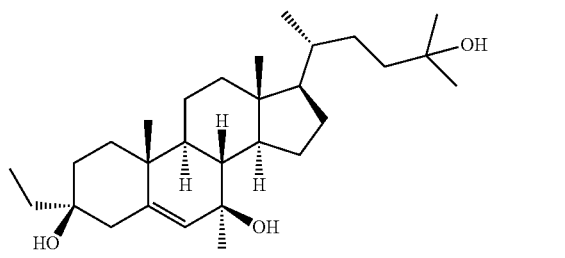
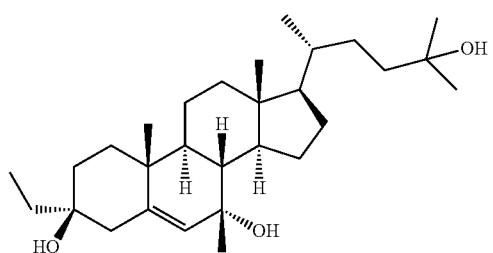
Overview:
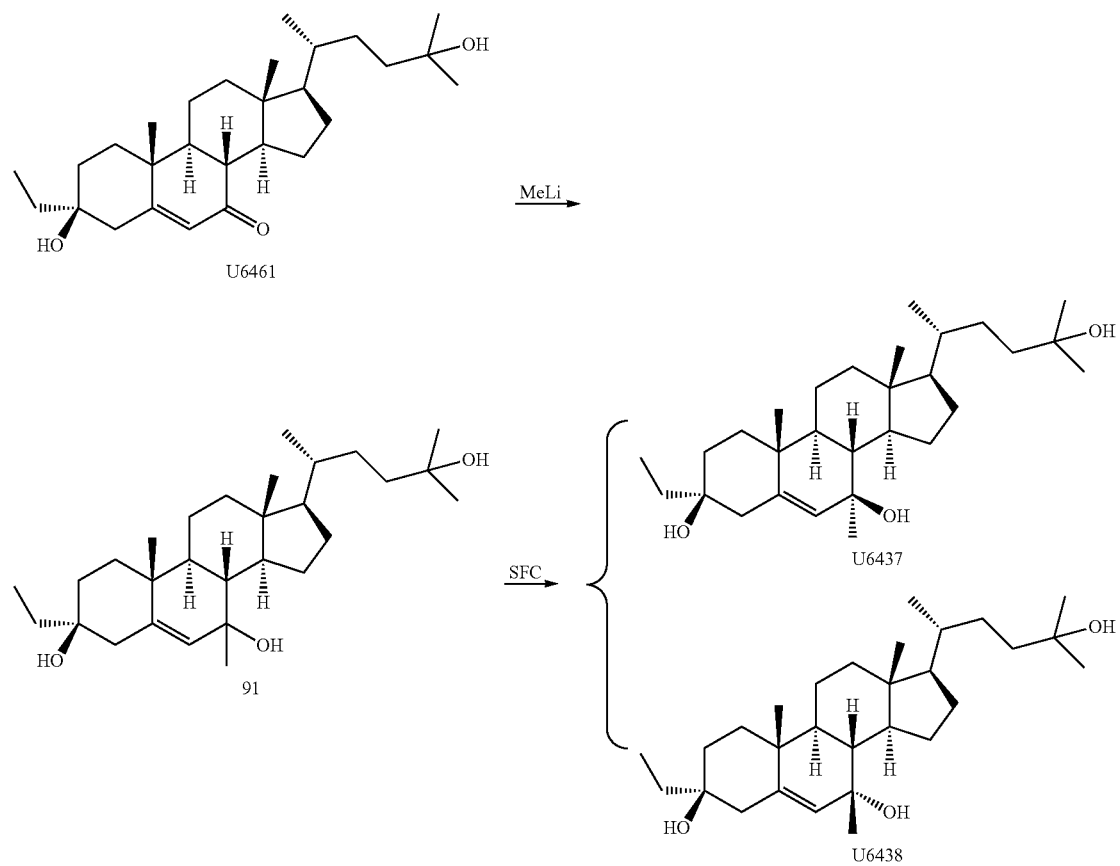

The synthesis of U6461 can be found in Example 11 herein.

Synthesis of 91

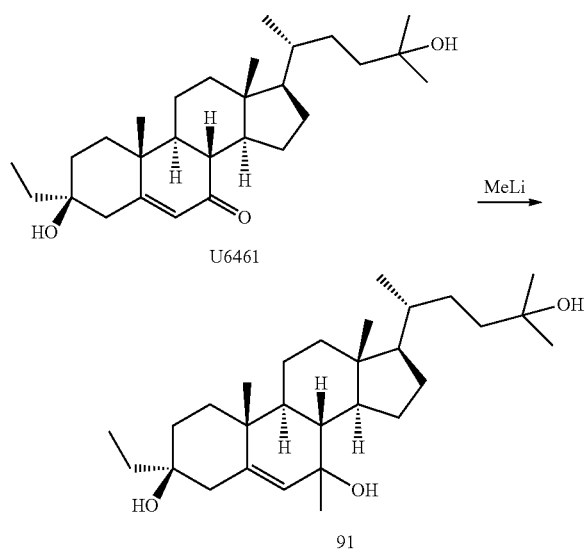

To a solution of U6461 (300 mg, 0.696 mmol) in THF (20 mL) was added MeLi (2.17 mL, 3.48 moml) at 0° C. under $N_2$. The mixture was stirred at 15° C. for 10 minutes and quenched with sat.NH$_4$Cl (30 mL). The reaction mixture was extracted with EtOAc (3×20 mL). The combined organic phase was washed with sat.NH$_4$Cl (50 mL), dried over Na$_2$SO$_4$, filtered, concentrated and purified by combi-flash (0-50% of EtOAc in PE) to give 91 (250 mg, 81%) as a solid.

Synthesis of U6437, U6438

160 mg of 91 was purified by SFC (column: AD (250 mm*30 mm, 5 um)), gradient: 50-50% B (A-0.05% NH$_3$/H$_2$O, B=MeOH) to give U6437 (Peak 1, 80 mg, 50%) and U6438 (Peak 2, 60 mg, 38%) as a solid.

U6437

$^1$H NMR (400 MHz, CDCl$_3$) δ 5.16-5.13 (m, 1H), 2.43-2.34 (m, 1H), 2.07-1.96 (m, 2H), 1.91-1.61 (m, 5H), 1.58-1.46 (m, 5H), 1.45-1.29 (m, 7H), 1.26-148 (m, 9H), 1.18-1.10 (m, 6H), 1.09-1.00 (m, 5H), 0.98-0.93 (m, 3H), 0.88-0.82 (m, 3H), 0.69 (s, 3H).

LCMS Rt=1.161 min in 2.0 min chromatography, 30-90AB_E, purity 100%, MS ESI calcd. for C$_{29}$H$_{47}$O [M+H−2H$_2$O]$^+$ 411, found 411.

SFC Rt=4.266 min in 8 min chromatography, AD_ETOH (DEA)_5_40_2.8ML_8MIN (Column: Chiralpak AD-3 100×4.6 mm I.D., 3 um Mobile phase: A: CO$_2$ B: ethanol (0.05% DEA)

Gradient: from 5% to 40% of B in 4-5 min and hold 40% for 2.5 min, then 5% of B for 1 min Flow rate: 2.8 mL/min Column temperature: 40° C.), 100% de

U6438

$^1$H NMR (400 MHz, CDCl$_3$) δ 5.19-5.16 (m, 1H), 2.40-2.32 (m, 1H), 2.08-1.98 (m, 2H), 1.94-1.85 (m, 2H), 1.77-1.59 (m, 4H), 1.52-1.29 (m, 13H), 1.24 (s, 3H), 1.22-1.19 (m, 6H), 1.17-1.03 (m, 6H), 0.99-0.92 (m, 6H), 0.88-0.82 (m, 3H), 0.70 (s, 3H).

LCMS Rt=1.162 min in 2.0 min chromatography, 30-90AB_E, purity 99.5%, MS ESI calcd. for C$_{29}$H$_{47}$O [M+H-2H$_2$O]$^+$ 411, found 411.

SFC Rt=5.815 min in 8 min chromatography, AD_ETOH (DEA)_5_40_2.8ML_8MIN (Column: Chiralpak AD-3 100×4.6 mm I.D., 3 um Mobile phase: A: CO2 B: ethanol (0.05% DEA)

Gradient: from 5% to 40% of B in 4.5 min and hold 40% for 2.5 min, then 5% of B for 1 min Flow rate: 2.8 mL/min Column temperature: 40° C.), 98% de.

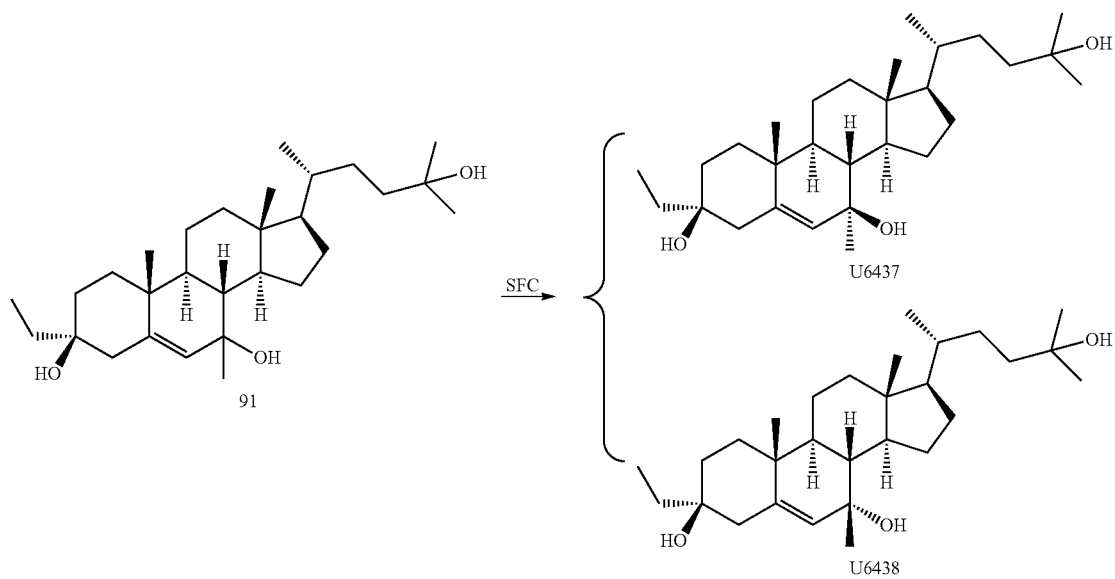

This compound structure was confirmed by X-ray.

Example 9: Synthesis of U6410

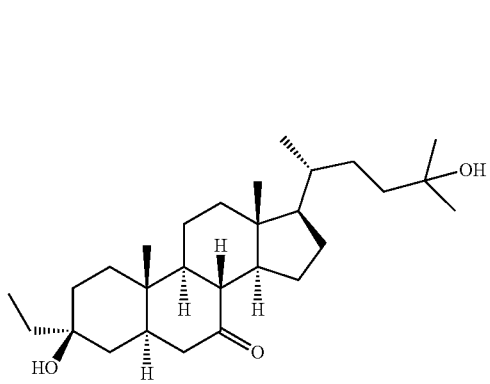
U6410

Overview:

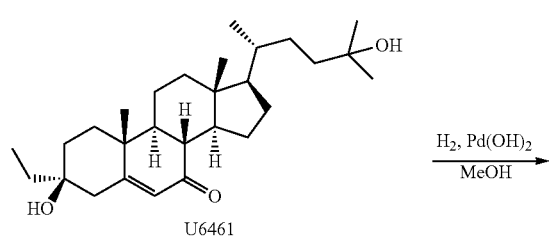

The synthesis of U6461 can be found in Example 11 herein.

Synthesis of U6410

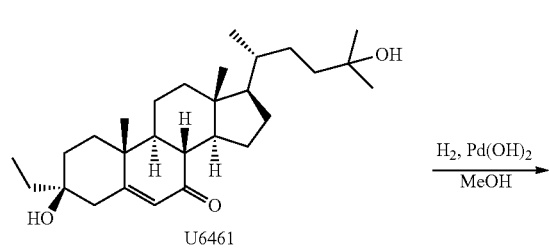

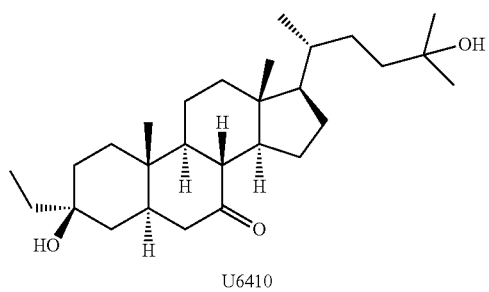
U6410

To a solution of U6461 (300 mg, 0.696 mmol) in MeOH (50 mL) was added Pd(OH)$_2$ (600 mg, dry). The mixture was stirred at 50 Psi, 50° C. for 48 hrs. The mixture was filtered, concentrated and purified by combi-flash (0-50% of EtOAc in PE) to give U6410 (35 mg, 12%) as a solid.

$^1$H NMR (400 MHz, CDCl$_3$) δ 2.39-2.29 (m, 2H), 2.26-2.15 (m, 1H), 2.03-1.87 (m, 3H), 1.70-1.56 (m, 5H), 1.53-1.37 (m, 8H), 1.36-1.24 (m, 4H), 1.23-1.16 (m, 7H), 1.15-1.04 (m, 7H), 1.02-0.90 (m, 5H), 0.89-0.83 (m, 3H), 0.65 (s, 3H).

LCMS—Rt=1.029 min in 2.0 min chromatography, 30-90AB_E, purity 100%, MS ESI calcd. for $C_{28}H_{47}O_2$ [M+H-H$_2$O]$^+$ 415, found 415.

Example 10: Synthesis of U6408, U6409

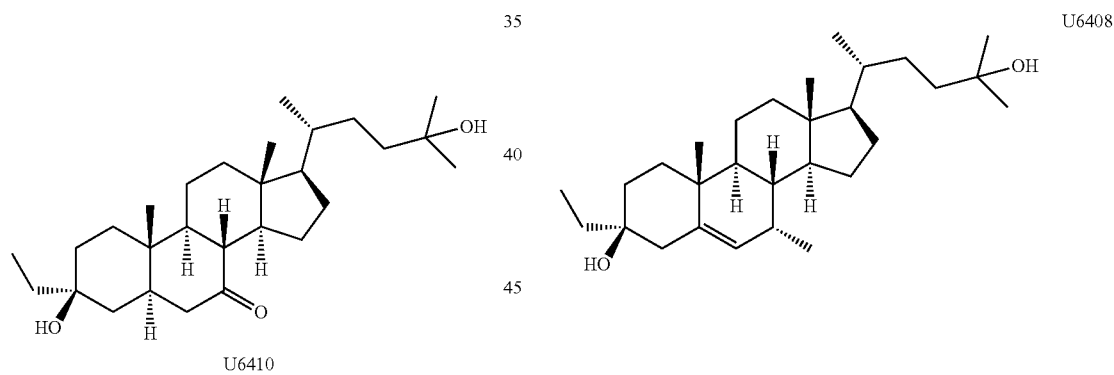

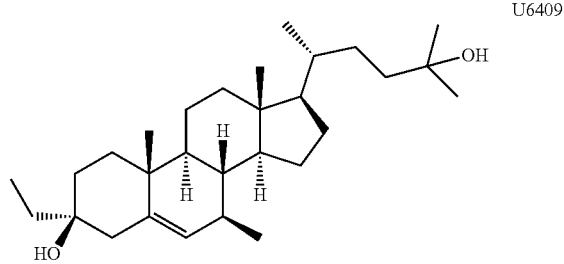

Overview:
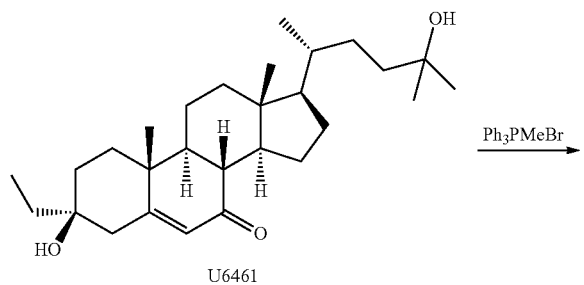
U6461 →(Ph₃PMeBr)
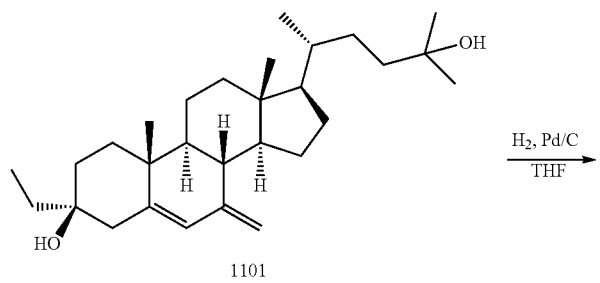
1101 →(H₂, Pd/C, THF)
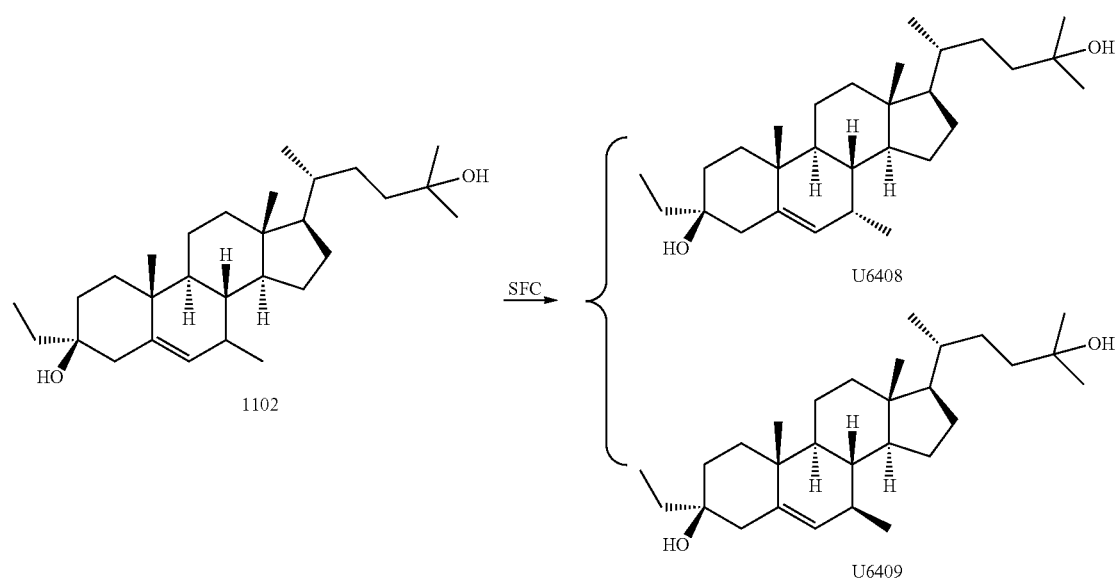
1102 →(SFC) { U6408, U6409 }

The synthesis of U6461 can be found in Example 11 herein.

Synthesis of 1101

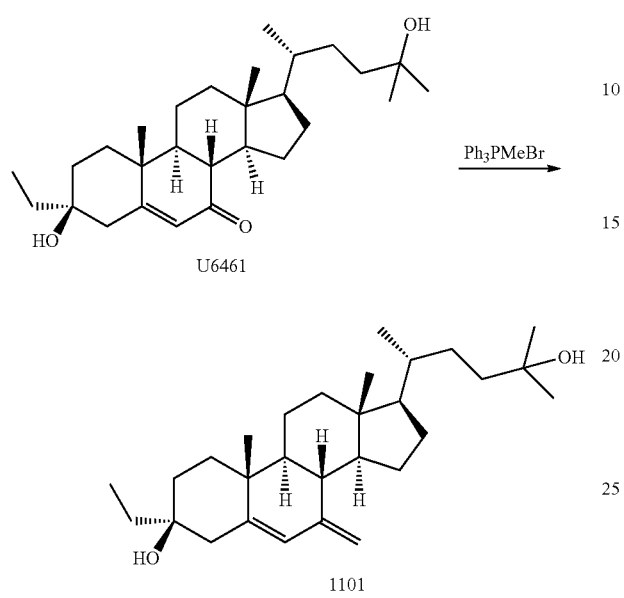

To a suspension of bromo(methyl)triphenylphosphorane (1.24 g, 3.48 mmo) in THF (45 mL) was added t-BuOK (389 mg, 3.48 mmol). The mixture was stirred at 50° C. for 30 minutes under $N_2$. Then a solution of U6461 (300 mg, 0.696 mmol) in THF (5 mL) was added and the mixture was stirred at 50° C. for 1 h. The mixture was quenched with sat.$NH_4Cl$ (50 mL) and extracted with EtOAc (3×15 mL). The combined organic phase was dried over $Na_2SO_4$, filtered, concentrated and purified by combi-flash (0-30% of EtOAc in PE) to give desired product (72 mg, 24%) as a solid.

$^1$H NMR (400 MHz, $CDCl_3$) δ 5.80-5.75 (m, 1H), 4.93 (s, 1H), 4.73 (s, 1H), 2.43-2.36 (m, 1H), 2.20-2.01 (m, 4H), 1.99-1.86 (m, 1H), 1.80-1.62 (m, 3H), 1.61-1.58 (m, 2H), 1.56-1.46 (m, 1H), 1.45-1.22 (m, 9H), 1.21-1.18 (m, 7H), 1.16-1.05 (m, 8H), 0.99-0.91 (m, 3H), 0.88-0.82 (m, 3H), 0.71 (s, 3H).

Synthesis of 1102

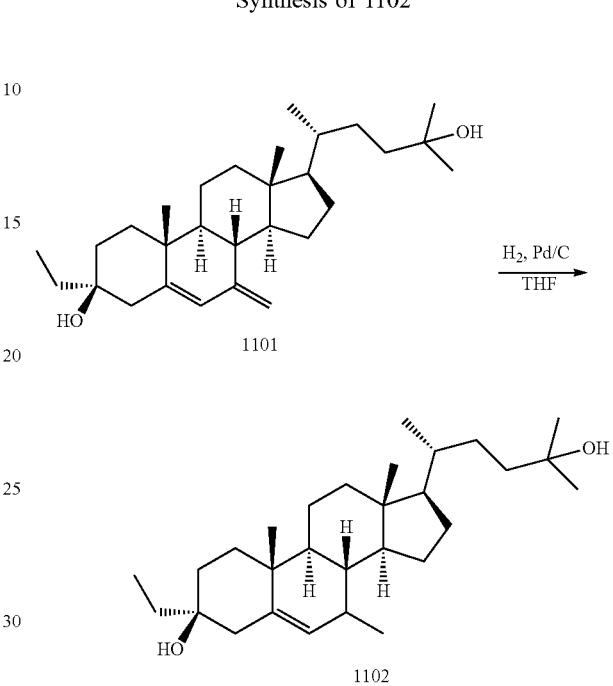

To a solution of 1101 (72 mg, 0.167 mmol) in THF (5 mL) was added Pd/C (wet, 150 mg). The mixture was stirred at 15° C., 15 Psi for 12 hrs. The mixture was filtered, concentrated and purified by combi-flash (0-10% of EtOAc in PE) to give impure 1102 (50 mg, 69%) as a solid.

Synthesis of U6408, U6409

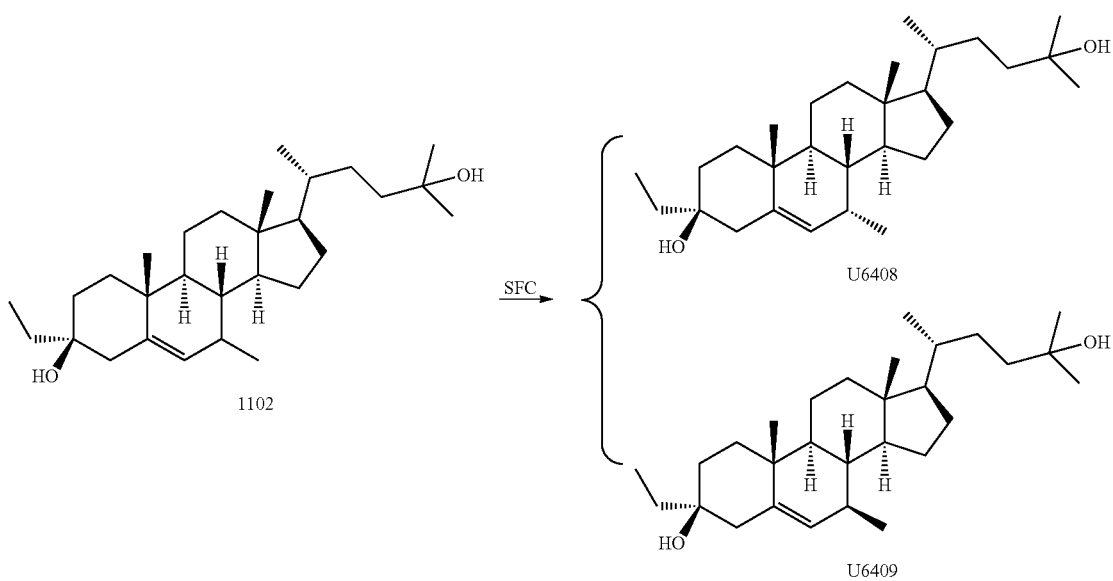

50 mg of impure 1102 was separated by SFC (column: AD (250 mm*30 mm, 10 um), gradient: 30; 30% B (A=0.05% NH$_3$/H$_2$Q, B=MeOH), flow rate: 60 mL/min) to give U6408 (Peak 1, 5 mg, 10%) and U6409 (Peak 2, 7 mg, 14%) as a solid. The stereochemistry at C$_7$ was assigned based on the featured HNMR of compound 82 and compound U6429 as a). 7-alpha-H isomer with H-6 as singlet in high field; b) 7-beta-H isomer with H-6 as doublet in low field.

U6408

$^1$H NMR (400 MHz, CDCl$_3$) δ 5.33-5.28 (m, 1H), 2.43-2.34 (m, 1H), 2.05-1.94 (m, 3H), 1.91-1.80 (m, 1H), 1.77-1.67 (m, 2H), 1.65-1.61 (m, 2H), 1.52-1.42 (m, 6H), 1.38-1.23 (m, 6H), 1.19 (s, 6H), 1.15-1.07 (m, 6H), 1.03 (s, 3H), 0.98-0.91 (m, 4H), 0.87-0.79 (m, 6H), 0.67 (s, 3H).

LCMS Rt=1.245 min in 2.0 min chromatography, 30-90AB_E, purity 100%, MS ESI calcd. for C$_{29}$H$_{47}$ [M+H-2H$_2$O]$^+$ 395, found 395.

SFC Rt=4.245 min in 10 min chromatography, Column: ChiralPak AD-3 150×4.6 mm I.D., 3 um Mobile phase: A: CO$_2$ B: Ethanol (0.05% DEA) Gradient: from 5% to 40% of B in 5.5 min and hold 40% for 3 min, then 5% of B for 1.5 min Flow rate: 2.5 mL/min Column temperature: 40° C., 100% de.

U6409

$^1$H NMR (400 MHz, CDCl$_3$) δ 5.04-4.99 (m, 1H), 2.38-2.28 (m, 1H), 2.07-1.96 (m, 2H), 1.92-1.78 (m, 2H), 1.72-1.62 (m, 4H), 1.53-1.44 (m, 4H), 1.43-1.25 (m, 8H), 1.19 (s, 6H), 1.16-1.05 (m, 6H), 0.99-0.91 (m, 1 OH), 0.88-0.81 (m, 3H), 0.68 (s, 3H).

LCMS Rt=1.253 min in 2.0 min chromatography, 30-90AB_E, purity 100%, MS ESI calcd. for C$_{29}$H$_{47}$ [M+H-2H$_2$O]$^+$ 395, found 395.

SFC Rt=4.967 min in 10 min chromatography, Column: ChiralPak AD-3 150×4.6 mm I.D., 3 um Mobile phase: A: CO$_2$ B: Ethanol (0.05% DEA) Gradient: from 5% to 40% of B in 5.5 min and hold 40% for 3 min, then 5% of B for 1.5 min Flow rate: 2.5 mL/min Column temperature: 40° C., 100% de.

Example 11: Synthesis of U6461, U6429, U6479

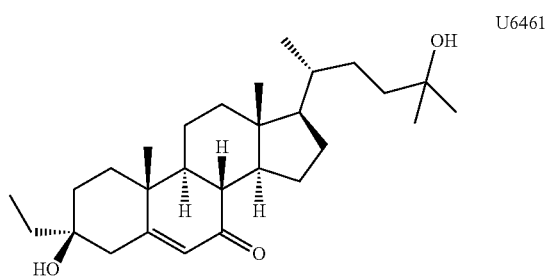

U6461

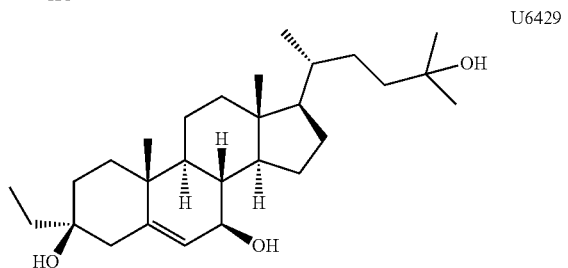

U6429

-continued

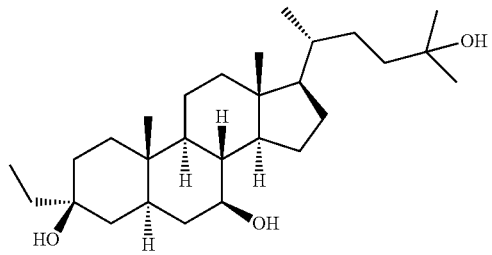

U6479

Overview:

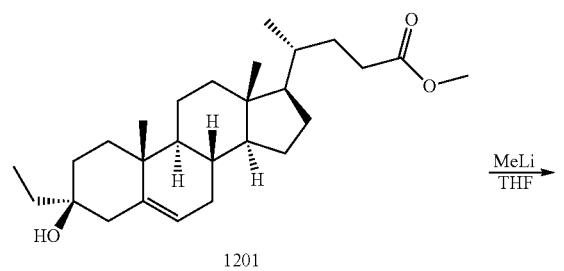

1201

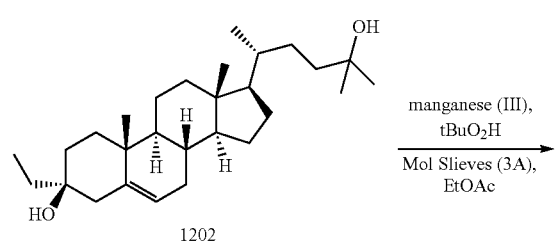

1202

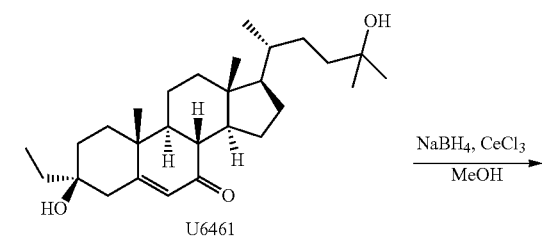

U6461

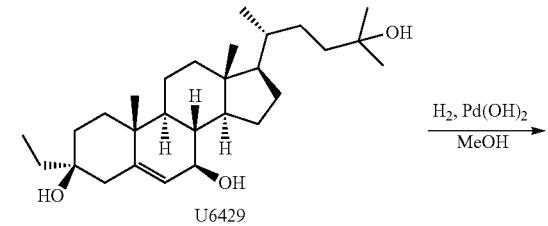

U6429

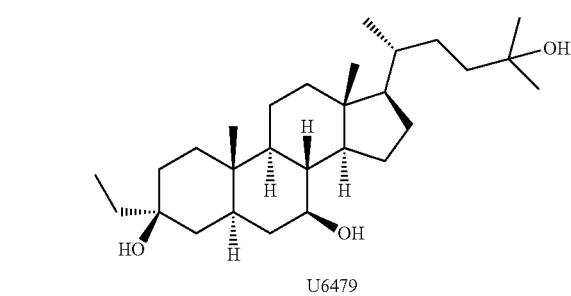

U6479

The synthesis of 1201 can be found in Example 4 herein.

Synthesis of 1202

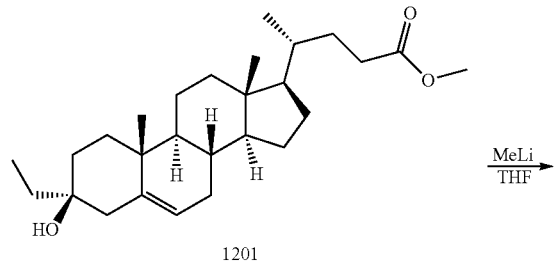

1201

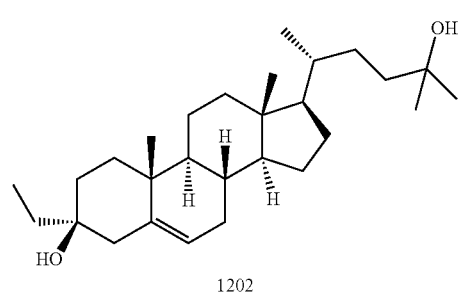

1202

To a solution of impure 1201 (14.9 g, 35.7 mmol) in THF (600 mL) was added dropwise MeLi (111 mL, 178 mmol, 1.6M in ether) at 0° C. After stirring at 15° C. for 30 minutes, the mixture was quenched with sat.NH$_4$Cl (500 mL) and extracted with EtOAc (3×200 mL). The combined organic phase was dried over Na$_2$SO$_4$, filtered and concentrated to give a crude residue, which was triturated with MeCN (300 mL) to give 11 g crude product as a solid. The crude was recrystallized from EtOAc (300 mL) to give 1202 (9 g, 80% purity, 49%) as a solid.

$^1$H NMR 1202 (400 MHz, CDCl$_3$) δ 5.28-5.25 (m, 1H), 2.40-2.32 (m, 1H), 2.05-1.92 (m, 3H), 1.90-1.80 (m, 1H), 1.79-1.58 (m, 3H), 1.56-1.51 (m, 5H), 1.50-1.39 (m, 7H), 1.38-1.28 (m, 2H), 1.27-1.16 (m, 6H), 1.15-1.04 (m, 5H), 1.02 (s, 3H), 1.00-0.96 (m, 1H), 0.95-0.88 (m, 4H), 0.87-0.77 (m, 3H), 0.68 (s, 3H).

Synthesis of U6461

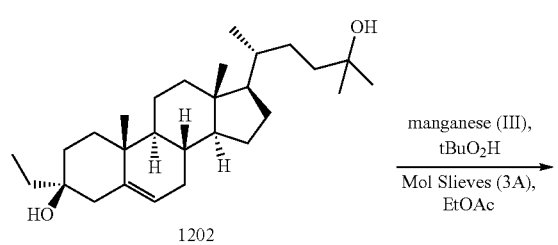

1202

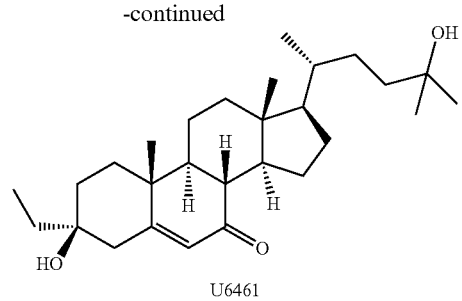

U6461

To a solution of 1202 (5 g, 11.9 mmol) in ethyl acetate (300 mL) was added molecular sieves (10 g) and t-butylhydroperoxide (11.9 mL, 71.4 mmol, 6 M in decane). The suspension was stirred under nitrogen atmosphere for 30 min and manganese(III) acetate dihydrate (956 mg, 3:57 mmol) was then added in one portion. The reaction mixture was stirred at 15° C. for 48 hrs. The solids were filtered off. The filtrate was washed with Na$_2$SO$_3$ (200 mL), brine (200 mL) and dried over Na$_2$SO$_4$, filtered and concentrated in vacuum. The residue was purified by silica gel chromatograph (0-15% of EtOAc in DCM) to afford impure U6461 (2 g, 40%) as a solid, of which 100 mg was recrystallized from MeCN (30 mL) at 90° C. to give pure U6461 (34 mg, 34%) as a solid.

$^1$H NMR (400 MHz, CDCl$_3$) δ 5:67-5.64 (m, 1H), 2.58-2.49 (m, 1H), 2.47-2.36 (m, 1H), 2.31-2.20 (m, 2H), 2.06-1.81 (m, 3H), 1.79-1.68 (m, 2H), 1.55-1.49 (m, 3H), 1.48-1.37 (m, 5H), 1.36-1.24 (m, 5H), 1.23-1.16 (m, 11H), 1.15-1.05 (m, 3H), 0.92-0.92 (m, 3H), 0:90-0.83 (m, 3H), 0.68 (s, 3H).

LCMS Rt=1.059 min in 2.0 min chromatography, 30-90 AB, purity 100%, MS ESI calcd. for C$_{28}$H$_{47}$O$_3$ [M+H]$^+$ 431, found 431.

Synthesis of U6429

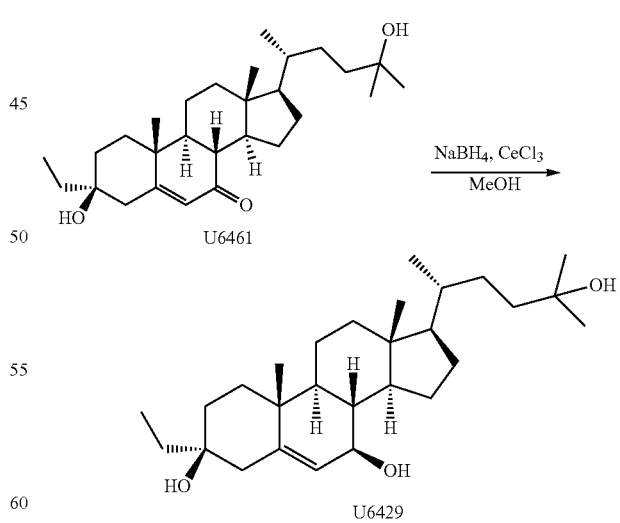

To a solution of U6461 (500 mg, 1.16 mmol) in MeOH (30 mL) was added CeCl$_3$ (857 mg, 3.48 mmol). After stirring at 15° C. for 30 minutes, NaBH$_4$ (197 mg, 5.80 mmol) was added in portions. The reaction mixture was stirred at 15° C. for 30 minutes. The mixture was quenched with sat.NH$_4$Cl (50 mL) and extracted with EtOAc (3×30 mL). The combined organic phase was washed with brine (2×100 mL), dried over Na$_2$SO$_4$, filtered and concentrated to give 470 mg crude product, which was recrystallized from MeCN (100 mL) to give U6429 (370 mg, 74%) as a solid. The stereochemistry at C$_7$ was assigned according to literature (Synthesis, 1987, 1002) compared with compound 82 based on a). 7-alpha-H isomer with H-6 as singlet in high field; b) 7-beta-H isomer with H-6 as doublet in low field.

$^1$H NMR (400 MHz, CDCl$_3$) δ 5.25-5.22 (m, 1H), 3.89-3.82 (m, 1H), 2.43-2.35 (m, 1H), 2.13-1.97 (m, 2H), 1.96-1.77 (m, 2H), 1.76-1.60 (m, 3H), 1.53-1.40 (m, 8H), 1.39-1.28 (m, 5H), 1.24-1.18 (m, 7H), 1.16-0.99 (m, 9H), 0.97-0.91 (m, 3H), 0.88-0.82 (m, 3H), 0.69 (s, 3H).

LCMS Rt=0.999 min in 2.0 min chromatography, 30-90AB_E, purity 100%, MS ESI calcd. for C$_{28}$H$_{45}$O [M+H-2H$_2$O]$^+$ 397, found 397. This compound structure was confirmed by X-ray.

Synthesis of U6479

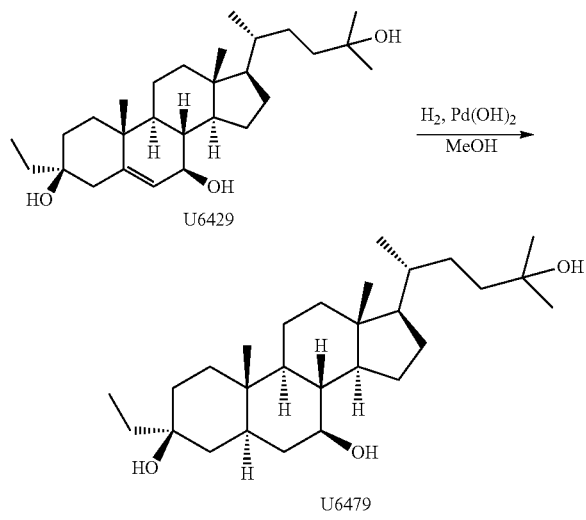

To a solution of U6429 (100 mg, 0.231 mmol) in MeOH (30 mL) was added Pd(OH)$_2$ (200 mg, dry). The mixture was stirred at 50° C. under H$_2$ (50 Psi) for 48 hrs. The mixture was filtered, concentrated and purified by combi-flash (0-50% of EtOAc in PE) to give U6479 (23 mg, 23%) as a solid.

$^1$H NMR (400 MHz, CDCl$_3$) δ 3.44-3.29 (m, 1H), 2.03-1.95 (m, 1H), 1.94-1.76 (m, 2H), 1.67-1.58 (m, 4H), 1.53-1.42 (m, 6H), 1.42-1.33 (m, 5H), 1.32-1.24 (m, 4H), 1.23-1.11 (m, 11H), 1.10-1.04 (m, 2H), 0.97-0.91 (m, 4H), 0.90-0.82 (m, 6H), 0.75-0.63 (m, 4H).

LCMS Rt=1.010 min in 2.0 min chromatography, 30-90AB_E, purity 100%, MS ESI calcd. for C$_{28}$H$_{45}$ [M+H-3H$_2$O]$^+$ 381, found 381.

Example 12: EC$_{50}$ and E$_{Max}$ Data

Automated Patch-Clamp System (OPatch HTX)

In this study, HEK 293 cells stably transfected with glutamate-activated channels of the GRIN1/2A subtype will be used together with submaximal NMDA concentrations (300 µM NMDA, co-application with 8 µM Glycine) to investigate the negative allosteric modulation of the test compounds.

Cell Culture

In general, cells will be passaged at a confluence of about 80% to ~90%. For electrophysiological measurements cells will be harvested at a confluence of about 80% to 90% from sterile culture flasks containing culture complete medium. Cells will be transferred as suspension in PBS to the QPatch 16X or QPatch HTX system to; the centrifuge/washer directly.

Standard Laboratory Conditions; Cells will be incubated at 37° C. in a humidified atmosphere with 5% CO$_2$ (rel. humidity about 95%).

Culture media: The cells will be continuously maintained in and passaged in sterile culture flasks containing a 1:1 mixture of Dulbecco's modified eagle medium and nutrient mixture F-12 (D-MEM/F-12 1×, liquid, with L-Glutamine) supplemented with 10% fetal bovine serum, 1% Penicillin/Streptomycin solution, and 50 µM AP-5 blocker.

Antibiotics: The complete medium as indicated above is supplemented with 100 µg/mL hygromycin, 15 µg/mL blasticidin and 1 µg/mL puromycin.

Induction of Expression-. 2.5 µg/mL tetracycline is added 24 h before start of experiments.

Dose Formulation

Dose levels are in terms of test compounds, as supplied. Vehicle will be added to achieve a stock concentration of 10 mM (storage at −10° C. to −30° C.). A further stock solutions of 1.0 mM will be prepared in DMSO. Details of stock solution usage (thawing, dose formulations) will be documented in the raw data. The time period of stock solution usage will be detailed in the report.

Test Compound Concentrations

Dose levels, are in terms of test compounds, as supplied. Vehicle will be added to achieve a stock concentration of 10 mM (storage at −10° C. to −30° C.). A further stock solutions of 1.0 mM will be prepared in DMSO. Details of stock solution usage (thawing, dose formulations) will be documented in the raw data. The time period of stock solution usage will be detailed in the report.

One test concentration of 1.0 µM will be tested.

All test solutions will be prepared by diluting the stock solutions with either Mg-free bath solution only or Mg-free bath solution containing NMDA (300 µM) and glycine (8.0 µM) shortly prior to the electrophysiological experiments and kept at room temperature (19° C. to 30° C.) when in use. 0.1% DMSO will be used as vehicle.

Frequency of preparation. For each test concentration, fresh solutions of test compounds will be prepared every day.

Stability of dose formulation: All preparation times will be documented in the raw data. Any observations regarding instability of test compounds will be mentioned in the raw data.

Storage of dose formulation: On the day of experimentation dose formulations will be maintained at room temperature (19° C. to 30° C.) when in use, Bath Solutions For preparing the experiments and for formation of the giga-ohm-seal, the following standard bath solution will be used:

Sodium Chloride: 137 mM; Potassium Chloride: 4 mM; Calcium Chloride: 1.8 mM; Magnesium Chloride: 1 mM; HEPES: 10 mM; D-Glucose: 10 mM; Cremophor: 0.02%; pH (NaOH): 7.4

The 1× bath solution will be prepared by diluting 10× bath solution without Glucose and 100× Glucose solution with water at least every 7 days. Both stock solutions have been prepared prior to the experimental start of the present study and stored at 1° C. to 9° C. (10× bath solution) or −10° C. to −30° (100× Glucose solution). The batch number(s) of the bath solution(s) used in the experiments will be documented in the raw data. When muse, the 1× bath solution will be kept at room temperature (19° C. to 30° C.). When not in use, the 1× bath solution will be stored at 1° C. to 9° C.

After the giga-seal was formed the following Mg-free bath solution will be used:

Sodium Chloride: 137 mM; Potassium Chloride: 4 mM; Calcium Chloride; 2:8 mM; HEPES: 10 mM; D-Glucose: 10 mM; Cremophor: 0.02%; pH (NaOH): 7.4

This Mg-free bath solution will be prepared as a 1× solution and stored at 1° C. to 9° C. It will be prepared freshly at least every 10 days.

Intracellular Solution

The 1× intracellular solution will be thawed every day out of a frozen 1× intracellular solution, which has been prepared prior to the experimental start of the present study, aliquoted and stored at −10° C. to −30° C. When in use, the 1× intracellular solution will kept at room temperature (19° C. to 30° C.). Remaining 1× intracellular solution will be stored in the fridge (1° C. to 9° C.). The 1× intracellular solution will include the components outlined below:

Potassium Chloride: 130 mM; Magnesium Chloride: 1 mM; Mg-ATP: 5 mM; HEPES: 10 mM; EGTA: 5 mM; pH (KOH): 7.2

Cell Treatment

For this study, cells will continuously be perfused with NMDA/Glycine, Test Compound or Test Compound/NMDA/Glycin.

In every case, at least 30-second prewash steps with a test compound will be performed in between applications. For details see Table A below.

Each experiment type will be analyzed in at least n=3 isolated cells. The NMDA and Glycine stock solutions will be prepared prior to the experimental start of the present study, stored frozen (−10° C. to −30° C.) until the day of experimentation. Shortly prior to the electrophysiological experiments, frozen stock solutions will be thawed and diluted.

Control: The effect of vehicle (0.1% DMSO) and D-(−)-2-Amino-5-phosphonopentanoic acid (AP-5) (100 μM) will be measured at three cells every second week, in order to assure successful expression of NMDA receptors.

The 50 mM stock solution of AP-5 has been prepared prior to the experimental start of the present study, aliquoted and stored frozen (−10° C. to −30° C.) until the day of experimentation. Shortly prior to the electrophysiological experiments the frozen stock solution will be thawed and then diluted in Mg-free bath solution containing NMDA (300 μM) and glycine (8.0 μM), to give a final perfusion concentration of 100 μM.

Experimental Procedure

Cells are transferred as suspension in serum-free medium to the QPatch HTX system and kept in the cell storage tank/stirrer during experiments. All solutions applied to cells including the intracellular solution will be maintained at room temperature (19° C. to 30° C.).

During the sealing process standard bath solution described above will be used. All solutions applied to cells including the pipette solution will be maintained at room temperature (19° C. to 30° C.). After formation of a Gigaohm seal between the patch electrodes and transfected individual HEK293 cells only Mg-free bath solution will be perfused and the cell membrane will be ruptured to assure electrical access to the cell interior (whole-cell patch-configuration). Inward currents will be measured upon application of 300 μM NMDA (and 8.0 μM Glycine) to patch-clamped cells for 5 sec. During the entire experiment the cells will be voltage-clamped at a holding potential of −80 mV.

For the analysis of test compounds, NMDA receptors will be stimulated by 300 μM NMDA and 8.0 μM Glycine and test compounds described below. Thirty-second prewash steps with a test compound will be performed in between applications.

TABLE A

Application Protocol; use dependence of test compounds

| Appl. # | Duration (s) | Application |
|---|---|---|
| 1 | 4 | NMDA/Glycine |
| 2 | 30 | Bath |
| 3 | 4 | NMDA/Glycine 2 repetitions |
| 4 | 30 | 1 μM Test Compound |
| 5 | 4 | 1 μM Test Compound + NMDA/Glycine 6 repetitions |
| 6 | 30 | Bath |
| 7 | 4 | NMDA/Glycine 2 repetitions |

TABLE B

Application Protocol; control experiments

| Appl. # | Duration (s) | Application |
|---|---|---|
| 1 | 4 | NMDA/Glycine |
| 2 | 30 | Bath |
| 3 | 4 | NMDA/Glycine 2 repetitions |
| 4 | 30 | Bath |
| 5 | 4 | NMDA/Glycine 6 repetitions |
| 6 | 30 | Bath |
| 7 | 4 | NMDA/Glycine + 100 μM AP-5 2 repetitions |

The results are reported in Table 1:

TABLE 1

| Structure | Compound ID | AVG_ $EC_{50}$ 2A nM | AVG_ $E_{MAX}$ 2A % | AVG_ $EC_{50}$ 2B nM | AVG_ $E_{MAX}$ 2B % |
|---|---|---|---|---|---|
| 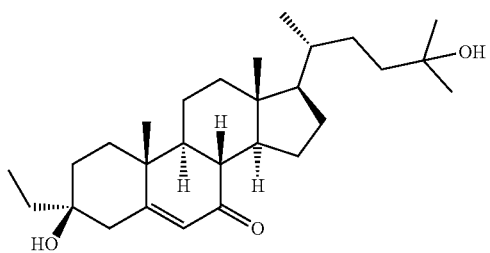 | U6461 | >10000 | 32 | >10000 | 53 |

TABLE 1-continued
| Structure | Compound ID | AVG_ EC$_{50}$ 2A nM | AVG_ E$_{MAX}$ 2A % | AVG_ EC$_{50}$2B nM | AVG_ E$_{MAX}$ 2B % |
|---|---|---|---|---|---|
| 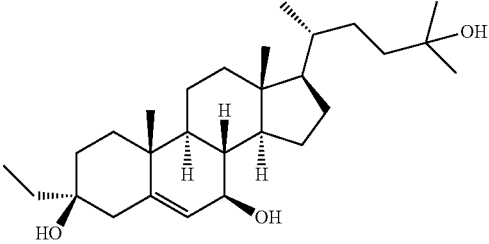 | U6429 | >10000 | 62 | 667 | 109 |
| 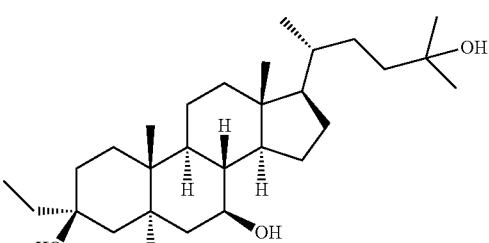 | U6479 | >10000 | 56 | 1425 | 92 |
| 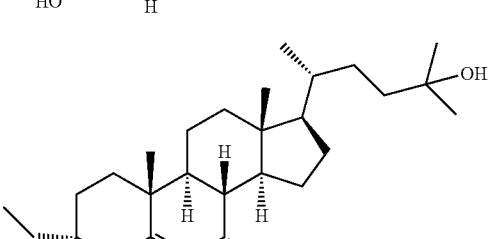 | U6408 | 230 | 343 | 132 | 447 |
| 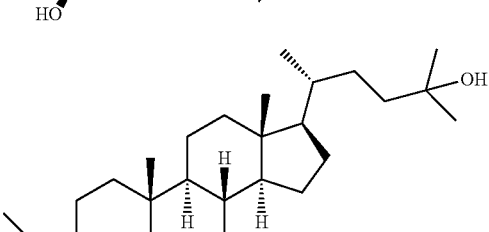 | U6409 | >10000 | 44 | >10000 | 71 |
| 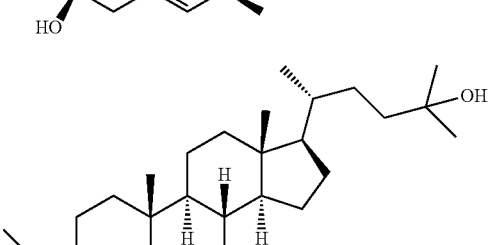 | U6410 | >10000 | 18 | >10000 | 44 |
| 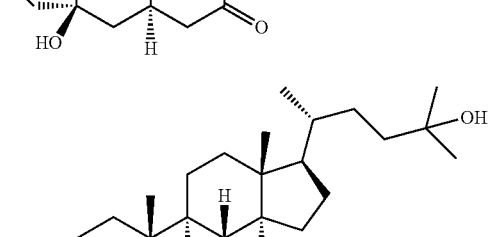 | U6437 | 1625 | 178 | 741 | 213 |

TABLE 1-continued
| Structure | Compound ID | AVG_ EC$_{50}$ 2A nM | AVG_ E$_{MAX}$ 2A % | AVG_ EC$_{50}$2B nM | AVG_ E$_{MAX}$ 2B % |
|---|---|---|---|---|---|
| 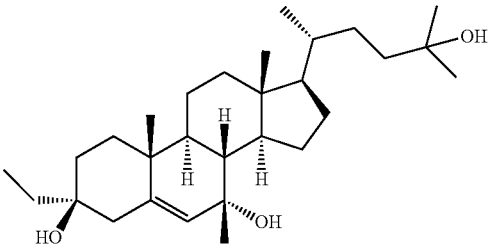 | U6438 | >10000 | 26 | >10000 | 15 |
| 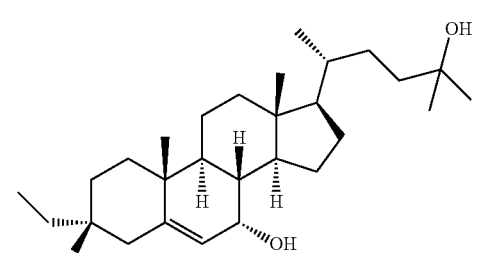 | U6450 | 710 | 98 | 66 | 111 |
| 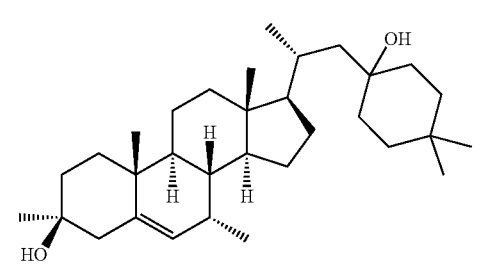 | U6477 | 747 | 160 | 698 | 86 |
| 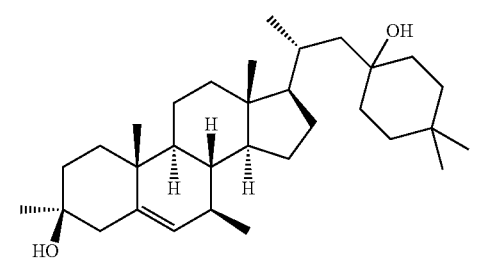 | U6478 | 191 | 170 | 160 | 127 |
| 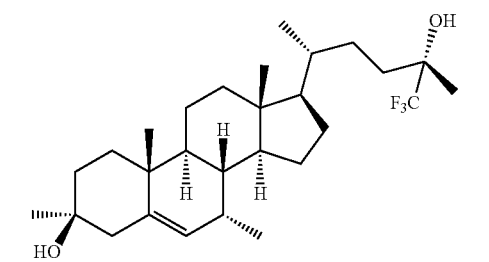 | U6472 | 12.99 | 122 | 22 | 231 |
| 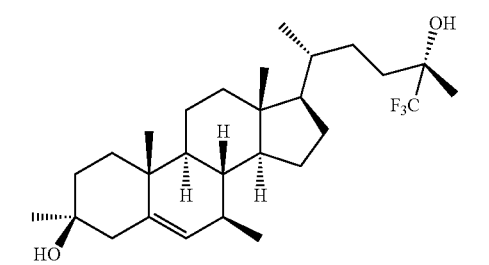 | U6473 | >10000 | 26 | >10000 | 47 |

Abbreviations

PCC: pyridinium chlorochromate; t-BuOK: potassium tert-butoxide; 9-BBN: 9-borabicyclo[3.3.1]nonane; Pd(t-Bu₃P)₂: bis(tri-tert-butylphosphine)palladium(0); AcCl: acetyl chloride; i-PrMgCl: Isopropylmagnesium chloride; TBSCl: tert-Butyl(chloro)dimethylsilane; (i-PrO)₄Ti: titanium tetraisopropoxide; BHT: 2,6-di-t-butyl-4-methylphenoxide; Me: methyl; i-Pr: iso-propyl; t-Bu: tert-butyl; Ph: phenyl; Et: ethyl; Bz: benzoyl; BzCl: benzoyl chloride; CsF: cesium fluoride; DCC: dicyclohexylcarbodiimide; DCM: dichloromethane; DMAP: 4-dimethylaminopyridine; DMP: Dess-Martin periodinane; EtMgBr: ethylmagnesium bromide; EtOAc: ethyl acetate; TEA: triethylamine; AlaOH: alanine; Boc: t-butoxycarbonyl. Py: pyridine; TBAF: tetra-n-butylammonium fluoride; THF: tetrahydrofuran; TBS: t-butyldimethylsilyl; TMS: trimethylsilyl; TMSCF₃: (Trifluoromethyl)trimethylsilane; Ts: p-toluenesulfonyl; Bu: butyl; Ti(OiPr)₄: tetraisopropoxytitanium; LAH: Lithium Aluminium Hydride; LDA: lithium diisopropylamide; LiOH.H₂O: lithium hydroxide hydrates; MAD: methyl aluminum bis(2,6-di-t-butyl-4-methylphenoxide); MeCN: acetonitrile; NBS: N-bromosuccinimide; Na₂SO₄: sodium sulfate; Na₂S₂O₃: sodium thiosulfate; PE: petroleum ether; MeCN: acetonitrile; MeOH: methanol; Boc: t-butoxycarbonyl; MTBE: methyl tert-butyl ether; K-selectride: Potassium tri(s-butyl)borohydride.

OTHER EMBODIMENTS

In the claims articles such as "a," "an," and "the" may mean one or more than one unless indicated to the contrary or otherwise evident from the context. Claims or descriptions that include, "or" between one or more members of a group are considered satisfied if one, more than one, or all of the group members, are present in, employed in, or otherwise, relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain, embodiments of the invention or aspects of the invention consist, or consist essentially of, such elements and/or features. For purposes of simplicity, those embodiments have not been specifically set forth in haec verba herein. It is also noted that the terms, "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of Formula (B):

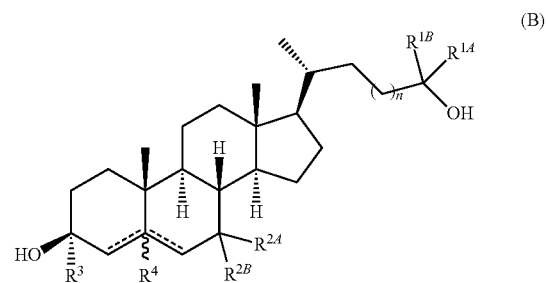

or a pharmaceutically acceptable salt thereof, wherein:
  each of $R^{1A}$ and $R^{1B}$ is independently hydrogen, substituted or unsubstituted alkyl, carbocyclyl, heterocyclyl, aryl, or heteroaryl, or $R^{1A}$ and $R^{1B}$, together with the carbon atom to which they are attached form a 3-8 membered ring;
  n is 1 or 2;
  each of $R^{2A}$ and $R^{2B}$ is independently hydrogen, halo, —$OR^C$, substituted or unsubstituted alkyl, alkenyl, alkynyl, aryl, or heteroaryl, wherein $R^C$ is hydrogen or alkyl, or $R^{2A}$ and $R^{2B}$, together with the carbon atom to which they are attached form an oxo group, wherein $R^{2A}$ and $R^{2B}$ are not both simultaneously hydrogen;
  $R^3$ is substituted or unsubstituted alkyl, alkenyl, or alkynyl, or —$OR^A$, wherein $R^A$ is alkyl;
  $R^4$ is absent or hydrogen; and
  ═ represents a single or double bond, wherein when one of ═ is a double bond, the other ═ is a single bond; when both of ═ are single bonds, then $R^4$ is hydrogen; and when one of the ═ is a double bond, $R^4$ is absent.

2. The compound of claim 1, where n is 1.
3. The compound of claim 1, where n is 2.
4. The compound of claim 1, wherein each of $R^{1A}$ and $R^{1B}$ is independently unsubstituted or substituted alkyl.

5. The compound of claim 4, wherein each of $R^{1A}$ and $R^{1B}$ is independently selected from the group consisting of haloalkyl, alkoxyalkyl, —$CH_3$, —$CH_2CH_3$, —$CH(CH_3)_2$, —$CF_3$ and —$CH_2OCH_3$.

6. The compound of claim 1, wherein $R^{1A}$ and $R^{1B}$, together with the carbon atom to which they are attached form a 3-8 membered ring.

7. The compound of claim 1, wherein $R^{1A}$ is hydrogen and $R^{1B}$ is alkyl, carbocyclyl, heterocyclyl, aryl, or heteroaryl.

8. The compound of claim 1, wherein each of $R^{2A}$ and $R^{2B}$ is independently substituted or unsubstituted alkyl.

9. The compound of claim 1, wherein $R^3$ is substituted or unsubstituted alkyl.

10. A pharmaceutical composition comprising a compound of claim 1, or a pharmaceutically acceptable salt thereof, and a pharmaceutically acceptable carrier.

11. The compound of claim 1, wherein the compounds is selected from the group consisting of

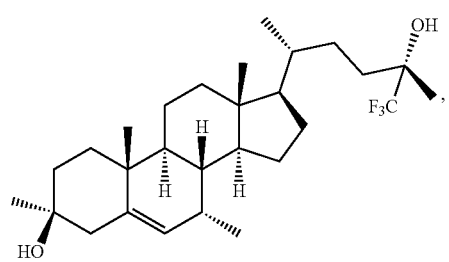

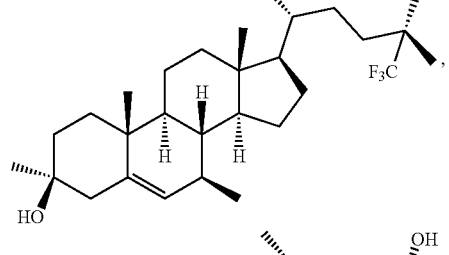

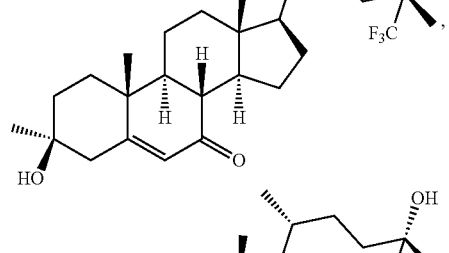

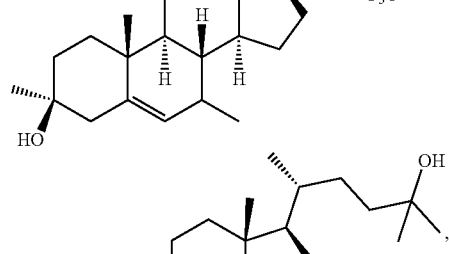

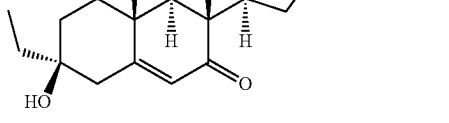

-continued

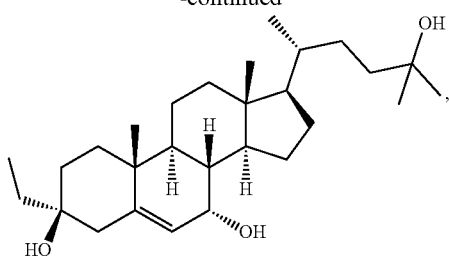

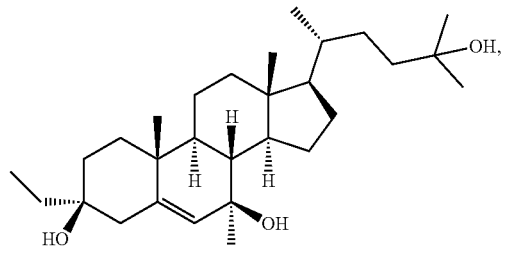

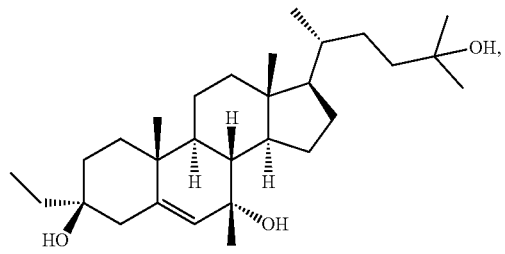

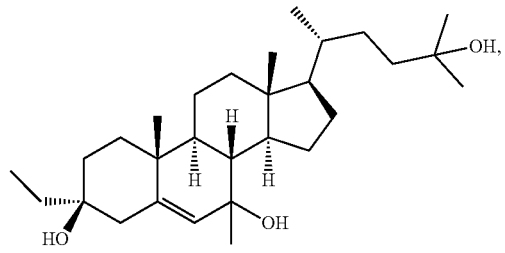

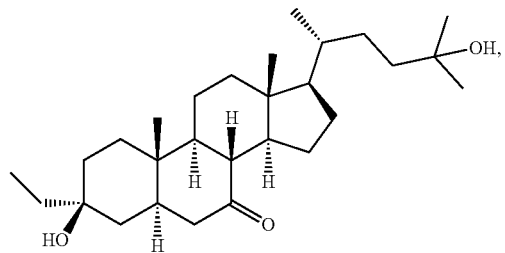

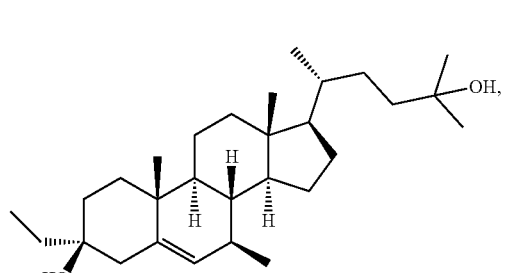

113
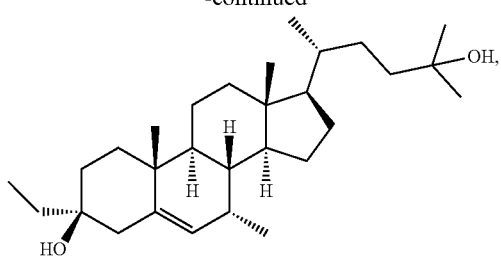
114
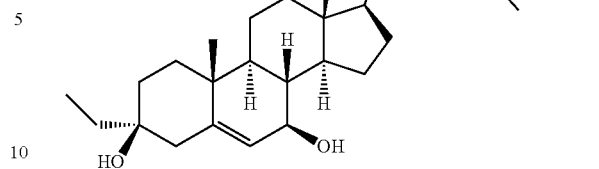
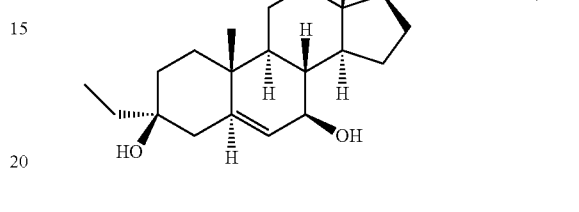
* * * * *